US009695169B2

(12) United States Patent
Ibrahim

(10) Patent No.: US 9,695,169 B2
(45) Date of Patent: *Jul. 4, 2017

(54) SYNTHESIS OF HETEROCYCLIC COMPOUNDS

(71) Applicant: Plexxikon Inc., Berkeley, CA (US)

(72) Inventor: Prabha N. Ibrahim, Mountain View, CA (US)

(73) Assignee: Plexxikon Inc., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/839,668

(22) Filed: Aug. 28, 2015

(65) Prior Publication Data

US 2015/0368243 A1 Dec. 24, 2015

Related U.S. Application Data

(63) Continuation of application No. 13/793,917, filed on Mar. 11, 2013, now Pat. No. 9,150,570.

(60) Provisional application No. 61/653,994, filed on May 31, 2012.

(51) Int. Cl.
*C07D 471/04* (2006.01)

(52) U.S. Cl.
CPC .................................. *C07D 471/04* (2013.01)

(58) Field of Classification Search
CPC .................................................... C07D 471/04
USPC ........................................................ 546/113
See application file for complete search history.

(56) References Cited

U.S. PATENT DOCUMENTS

| | | | |
|---|---|---|---|
| 2,234,705 A | 3/1941 | Duennebier et al. |
| 2,413,258 A | 12/1946 | Soday |
| 4,150,949 A | 4/1979 | Smith |
| 4,301,159 A | 11/1981 | Ogata et al. |
| 4,439,444 A | 3/1984 | Nisato et al. |
| 4,568,649 A | 2/1986 | Bertoglio-Matte |
| 4,595,780 A | 6/1986 | Ogata et al. |
| 4,626,513 A | 12/1986 | Burton et al. |
| 4,634,701 A | 1/1987 | De Vincentiis |
| 4,714,693 A | 12/1987 | Targos |
| 4,727,395 A | 2/1988 | Oda et al. |
| 4,863,945 A | 9/1989 | Friebe et al. |
| 5,120,782 A | 6/1992 | Hubsch et al. |
| 5,143,854 A | 9/1992 | Pirrung et al. |
| 5,338,849 A | 8/1994 | Festal et al. |
| 5,360,882 A | 11/1994 | Dougherty et al. |
| 5,426,039 A | 6/1995 | Wallace et al. |
| 5,432,177 A | 7/1995 | Baker et al. |
| 5,434,049 A | 7/1995 | Okano et al. |
| 5,449,614 A | 9/1995 | Danos et al. |
| 5,474,935 A | 12/1995 | Chatterjee et al. |
| 5,486,525 A | 1/1996 | Summers, Jr. et al. |
| 5,556,752 A | 9/1996 | Lockhart et al. |
| 5,576,319 A | 11/1996 | Baker et al. |
| 5,580,859 A | 12/1996 | Felgner et al. |
| 5,631,236 A | 5/1997 | Woo et al. |
| 5,632,957 A | 5/1997 | Heller et al. |
| 5,658,775 A | 8/1997 | Gilboa |
| 5,681,959 A | 10/1997 | Bishop et al. |
| 5,700,637 A | 12/1997 | Southern |
| 5,700,809 A | 12/1997 | Leeson et al. |
| 5,712,285 A | 1/1998 | Curtis et al. |
| 5,721,118 A | 2/1998 | Scheffler |
| 5,744,305 A | 4/1998 | Fodor et al. |
| 5,747,276 A | 5/1998 | Hoch et al. |
| 5,763,198 A | 6/1998 | Hirth et al. |
| 5,770,456 A | 6/1998 | Holmes |
| 5,800,992 A | 9/1998 | Fodor et al. |
| 5,807,522 A | 9/1998 | Brown et al. |
| 5,830,645 A | 11/1998 | Pinkel et al. |
| 5,840,485 A | 11/1998 | Lebl et al. |
| 5,856,174 A | 1/1999 | Lipshutz et al. |
| 5,858,995 A | 1/1999 | Kawai et al. |
| 5,877,007 A | 3/1999 | Housey |
| 5,908,401 A | 6/1999 | Henley |
| 5,952,362 A | 9/1999 | Cournoyer et al. |
| 5,958,930 A | 9/1999 | Gangjee |
| 5,959,098 A | 9/1999 | Goldberg et al. |
| 5,965,452 A | 10/1999 | Kovacs et al. |
| 6,013,440 A | 1/2000 | Lipshutz et al. |
| 6,022,963 A | 2/2000 | McGall et al. |
| 6,025,155 A | 2/2000 | Hadlaczky et al. |
| 6,045,996 A | 4/2000 | Cronin et al. |
| 6,048,695 A | 4/2000 | Bradley et al. |
| 6,054,270 A | 4/2000 | Southern |
| 6,090,912 A | 7/2000 | Lebl et al. |
| 6,096,718 A | 8/2000 | Weitzman et al. |
| 6,107,478 A | 8/2000 | Pedersen et al. |
| 6,110,456 A | 8/2000 | During et al. |

(Continued)

FOREIGN PATENT DOCUMENTS

| | | |
|---|---|---|
| CA | 2550361 | 4/2014 |
| EP | 0 154 734 | 9/1985 |

(Continued)

OTHER PUBLICATIONS

U.S. Appl. No. 15/147,781, filed May 5, 2016, Bollag et al.
U.S. Appl. No. 15/147,692, filed May 5, 2016, Ibrahim et al.
U.S. Appl. No. 15/147,709, filed May 5, 2016, Ibrahim et al.
U.S. Appl. No. 15/048,851, filed Feb. 19, 2016, Wu et al.
U.S. Appl. No. 15/093,660, filed Apr. 7, 2016, Lin et al.
U.S. Appl. No. 61/054,445, filed May 19, 2008, Ibrahim et al.
U.S. Appl. No. 61/060,418, filed Jun. 10, 2008, Ibrahim et al.
Abou-Khalil, et al., "Delayed bone regeneration is linked to chronic inflammation in murine muscular dystrophy," *J. Bone Miner. Res.*, (2013), DOI 10.1002/jbmr.2038.
Ahmad, K., "BRAF mutation common to 70% of thyroid carcinomas," *The Lancet, Oncology*, (2003), 4:330.
Allegretti, et al., "Palladium-Catalysed Functionalisation at 4- and 6- Position of the 7-Azaindole System," *Synlett*, (2001), 5:609-612.
Al-Obeidi, et al., "Peptide and Peptidomimetic Libraries," *Mol Biotechnol.*, (1998), 9:205-223.

(Continued)

*Primary Examiner* — Noble Jarrell
*Assistant Examiner* — Daniel Carcanague
(74) *Attorney, Agent, or Firm* — Sheppard Mullin Richter & Hampton LLP

(57) ABSTRACT

Provided herein are intermediates and processes useful for facile synthesis of biologically active molecules.

20 Claims, No Drawings

(56) References Cited

U.S. PATENT DOCUMENTS

| | | |
|---|---|---|
| 6,110,458 A | 8/2000 | Freeman et al. |
| 6,113,913 A | 9/2000 | Brough et al. |
| 6,117,681 A | 9/2000 | Salmons et al. |
| 6,161,776 A | 12/2000 | Byles |
| 6,178,384 B1 | 1/2001 | Kolossváry |
| 6,235,769 B1 | 5/2001 | Clary |
| 6,243,980 B1 | 6/2001 | Bronstein et al. |
| 6,258,606 B1 | 7/2001 | Kovacs |
| 6,261,776 B1 | 7/2001 | Pirrung et al. |
| 6,277,489 B1 | 8/2001 | Abbott et al. |
| 6,277,628 B1 | 8/2001 | Johann et al. |
| 6,288,234 B1 | 9/2001 | Griffin |
| 6,294,330 B1 | 9/2001 | Michnick et al. |
| 6,310,074 B1 | 10/2001 | Depreux et al. |
| 6,350,786 B1 | 2/2002 | Albano et al. |
| 6,545,014 B2 | 4/2003 | Verner |
| 6,653,309 B1 | 11/2003 | Saunders et al. |
| 6,858,860 B2 | 2/2005 | Hosono et al. |
| 6,897,207 B2 | 5/2005 | Cox et al. |
| 7,259,165 B2 | 8/2007 | Bernotas et al. |
| 7,271,262 B2 | 9/2007 | La Greca et al. |
| 7,361,763 B2 | 4/2008 | Arnold et al. |
| 7,361,764 B2 | 4/2008 | Arnold et al. |
| 7,452,993 B2 | 11/2008 | Arnold et al. |
| 7,498,342 B2 | 3/2009 | Ibrahim et al. |
| 7,504,509 B2 | 3/2009 | Ibrahim et al. |
| 7,582,637 B2 | 9/2009 | Arnold et al. |
| 7,601,839 B2 | 10/2009 | Arnold et al. |
| 7,626,021 B2 | 12/2009 | Arnold et al. |
| 7,846,941 B2 | 12/2010 | Zhang et al. |
| 7,863,288 B2 | 1/2011 | Ibrahim et al. |
| 7,863,289 B2 | 1/2011 | Spevak et al. |
| 7,893,075 B2 | 2/2011 | Zhang et al. |
| 7,947,708 B2 | 5/2011 | Ibrahim et al. |
| 7,994,185 B2 | 8/2011 | Rheault |
| 8,067,638 B2 | 11/2011 | Kai et al. |
| 8,129,404 B2 | 3/2012 | Ibrahim et al. |
| 8,143,271 B2 | 3/2012 | Ibrahim et al. |
| 8,198,273 B2 | 6/2012 | Ibrahim et al. |
| 8,404,700 B2 | 3/2013 | Ibrahim et al. |
| 8,415,469 B2 | 4/2013 | Ibrahim et al. |
| 8,470,818 B2 | 6/2013 | Ibrahim et al. |
| 2001/0001449 A1 | 5/2001 | Kiliany et al. |
| 2001/0008765 A1 | 7/2001 | Shinoki et al. |
| 2001/0012537 A1 | 8/2001 | Anderson et al. |
| 2001/0014448 A1 | 8/2001 | Chappa et al. |
| 2001/0014449 A1 | 8/2001 | Nerenberg et al. |
| 2001/0016322 A1 | 8/2001 | Caren et al. |
| 2001/0018642 A1 | 8/2001 | Balaban et al. |
| 2001/0019827 A1 | 9/2001 | Dawson et al. |
| 2003/0003004 A1 | 1/2003 | Stones et al. |
| 2003/0219489 A1 | 11/2003 | Curatolo et al. |
| 2004/0002534 A1 | 1/2004 | Lipson et al. |
| 2004/0022534 A1 | 2/2004 | Amano et al. |
| 2004/0073274 A1 | 4/2004 | Cook et al. |
| 2004/0077595 A1 | 4/2004 | Cheng et al. |
| 2004/0142864 A1 | 7/2004 | Bremer et al. |
| 2004/0167030 A1 | 8/2004 | Bernotas et al. |
| 2005/0026792 A1 | 2/2005 | Cartwright |
| 2005/0031692 A1 | 2/2005 | Beyerinck et al. |
| 2005/0085463 A1 | 4/2005 | Weiner et al. |
| 2005/0154014 A1 | 7/2005 | Bloxham et al. |
| 2005/0164300 A1 | 7/2005 | Artis et al. |
| 2005/0170431 A1 | 8/2005 | Ibrahim et al. |
| 2005/0256151 A1 | 11/2005 | Salom et al. |
| 2006/0018726 A1 | 1/2006 | Hall |
| 2006/0024361 A1 | 2/2006 | Odidi et al. |
| 2006/0035898 A1 | 2/2006 | Arnold et al. |
| 2006/0058324 A1 | 3/2006 | Capraro et al. |
| 2006/0058339 A1 | 3/2006 | Ibrahim et al. |
| 2006/0058340 A1 | 3/2006 | Ibrahim et al. |
| 2006/0167403 A1 | 7/2006 | Henley et al. |
| 2007/0032519 A1 | 2/2007 | Zhang et al. |
| 2007/0049615 A1 | 3/2007 | Ibrahim et al. |
| 2007/0054963 A1 | 3/2007 | Lifshitz-Liron et al. |
| 2007/0072862 A1 | 3/2007 | Dimauro et al. |
| 2007/0161666 A1 | 7/2007 | Blumenkopf et al. |
| 2007/0218138 A1 | 9/2007 | Bittorf et al. |
| 2007/0225306 A1 | 9/2007 | Choi et al. |
| 2007/0287711 A1 | 12/2007 | Arnold et al. |
| 2008/0004661 A1 | 1/2008 | Silverstone |
| 2008/0079906 A1 | 4/2008 | Finn |
| 2008/0167338 A1 | 7/2008 | Spevak et al. |
| 2008/0188514 A1 | 8/2008 | Wu et al. |
| 2009/0005356 A1 | 1/2009 | Blaney et al. |
| 2009/0076046 A1 | 3/2009 | Zhang et al. |
| 2009/0143352 A1 | 6/2009 | Arnold et al. |
| 2009/0286783 A1 | 11/2009 | Ibrahim et al. |
| 2009/0306056 A1 | 12/2009 | Arnold et al. |
| 2009/0306086 A1 | 12/2009 | Ibrahim et al. |
| 2009/0306087 A1 | 12/2009 | Ibrahim et al. |
| 2010/0249118 A1 | 9/2010 | Ibrahim et al. |
| 2010/0256365 A1 | 10/2010 | Ibrahim et al. |
| 2010/0286142 A1 | 11/2010 | Ibrahim et al. |
| 2010/0286178 A1 | 11/2010 | Ibrahim et al. |
| 2010/0310659 A1 | 12/2010 | Desai et al. |
| 2011/0028511 A1 | 2/2011 | Hildbrand et al. |
| 2011/0059963 A1 | 3/2011 | Ibrahim et al. |
| 2011/0092538 A1 | 4/2011 | Spevak et al. |
| 2011/0112127 A1 | 5/2011 | Zhang et al. |
| 2011/0112136 A1 | 5/2011 | Diodone et al. |
| 2011/0152258 A1 | 6/2011 | Ibrahim et al. |
| 2011/0183988 A1 | 7/2011 | Ibrahim et al. |
| 2012/0022098 A1 | 1/2012 | Ibrahim et al. |
| 2012/0053177 A1 | 3/2012 | Ibrahim et al. |
| 2012/0122860 A1 | 5/2012 | Visor et al. |
| 2012/0165366 A1 | 6/2012 | Ibrahim et al. |
| 2012/0245174 A1 | 9/2012 | Ibrahim et al. |
| 2013/0172375 A1 | 7/2013 | Albano et al. |
| 2013/0261117 A1 | 10/2013 | Ibrahim et al. |
| 2013/0274259 A1 | 10/2013 | Zhang et al. |
| 2013/0303534 A1 | 11/2013 | Ibrahim et al. |
| 2014/0037617 A1 | 2/2014 | Bollag et al. |
| 2014/0128373 A1 | 5/2014 | Ibrahim et al. |
| 2014/0243365 A1 | 8/2014 | Zhang et al. |
| 2014/0288070 A1 | 9/2014 | Bollag et al. |
| 2014/0357612 A1* | 12/2014 | Zhang .................. C07D 487/04 514/210.2 |
| 2016/0068528 A1 | 3/2016 | Zhang et al. |
| 2016/0075712 A1 | 3/2016 | Shi et al. |

FOREIGN PATENT DOCUMENTS

| | | |
|---|---|---|
| EP | 0 148 725 | 5/1987 |
| EP | 0 344 603 | 10/1991 |
| EP | 0 465 970 | 1/1992 |
| EP | 0 870 768 | 10/1998 |
| EP | 0 596 406 | 12/1998 |
| EP | 1 057 826 | 12/2000 |
| EP | 1 267 111 | 12/2002 |
| EP | 1 388 541 | 2/2004 |
| EP | 0 988 863 | 4/2004 |
| EP | 0 580 860 | 12/2004 |
| EP | 1 368 001 | 10/2005 |
| EP | 1 749 829 | 2/2007 |
| EP | 0 901 786 | 7/2007 |
| EP | 2 036 990 | 4/2014 |
| FR | 2264804 | 10/1975 |
| GB | 1 198 301 A | 7/1970 |
| GB | 145299 | 9/1976 |
| GB | 2 292 143 | 2/1996 |
| GB | 2 292 145 | 2/1996 |
| GB | 2 298 198 | 8/1996 |
| GB | 2 299 581 | 10/1996 |
| JP | 06-135946 | 5/1994 |
| JP | 10-087629 | 4/1998 |
| JP | 10-130269 | 5/1998 |
| JP | 2000-95708 | 4/2000 |
| JP | 2001-278886 | 10/2001 |
| JP | 15-073357 | 3/2003 |
| WO | WO-93/13099 | 7/1993 |
| WO | WO-94/14808 | 7/1994 |
| WO | WO-94/20459 | 9/1994 |
| WO | WO-94/20497 | 9/1994 |

(56) References Cited

FOREIGN PATENT DOCUMENTS

| | | |
|---|---|---|
| WO | WO-95/04742 | 2/1995 |
| WO | WO-95/07910 | 3/1995 |
| WO | WO-95/28387 | 10/1995 |
| WO | WO-96/00226 | 1/1996 |
| WO | WO-96/17958 | 1/1996 |
| WO | WO-96/05200 | 2/1996 |
| WO | WO-96/11929 | 4/1996 |
| WO | WO-96/18738 | 8/1996 |
| WO | WO-96/38131 | 12/1996 |
| WO | WO-97/03967 | 2/1997 |
| WO | WO-97/46313 | 12/1997 |
| WO | WO-97/46558 | 12/1997 |
| WO | WO-97/49703 | 12/1997 |
| WO | WO-98/06433 | 2/1998 |
| WO | WO-98/22457 | 5/1998 |
| WO | WO-98/47899 | 10/1998 |
| WO | WO-99/00386 | 1/1999 |
| WO | WO-99/09217 | 2/1999 |
| WO | WO-99/32106 | 7/1999 |
| WO | WO-99/32433 | 7/1999 |
| WO | WO-99/51231 | 10/1999 |
| WO | WO-99/51232 | 10/1999 |
| WO | WO-99/51233 | 10/1999 |
| WO | WO-99/51234 | 10/1999 |
| WO | WO-99/51595 | 10/1999 |
| WO | WO-99/51596 | 10/1999 |
| WO | WO-99/51773 | 10/1999 |
| WO | WO-00/09162 | 2/2000 |
| WO | WO-00/12514 | 3/2000 |
| WO | WO-00/17202 | 3/2000 |
| WO | WO-00/29411 | 5/2000 |
| WO | WO-00/12074 | 8/2000 |
| WO | WO-00/53582 | 9/2000 |
| WO | WO-00/55153 | 9/2000 |
| WO | WO-00/64898 | 11/2000 |
| WO | WO-00/71506 | 11/2000 |
| WO | WO-00/71537 | 11/2000 |
| WO | WO-00/75139 | 12/2000 |
| WO | WO-01/09121 | 2/2001 |
| WO | WO-01/24236 | 4/2001 |
| WO | WO-01/29036 | 4/2001 |
| WO | WO-01/46196 | 6/2001 |
| WO | WO-01/62255 | 8/2001 |
| WO | WO-01/60822 | 9/2001 |
| WO | WO-01/74786 | 10/2001 |
| WO | WO-01/98299 | 12/2001 |
| WO | WO-02/18346 | 3/2002 |
| WO | WO-02/00657 | 6/2002 |
| WO | WO-02/078780 | 10/2002 |
| WO | WO-02/083175 | 10/2002 |
| WO | WO-02/085896 | 10/2002 |
| WO | WO-02/102783 | 12/2002 |
| WO | WO-03/000258 | 1/2003 |
| WO | WO-03/000267 | 1/2003 |
| WO | WO-03/003004 | 1/2003 |
| WO | WO-03/004472 | 1/2003 |
| WO | WO-03/006459 | 1/2003 |
| WO | WO-03/008422 | 1/2003 |
| WO | WO-03/011868 | 2/2003 |
| WO | WO-03/020698 | 3/2003 |
| WO | WO-03/028724 | 4/2003 |
| WO | WO-03/037862 | 5/2003 |
| WO | WO-03/064413 | 8/2003 |
| WO | WO-03/068221 | 8/2003 |
| WO | WO-03/051838 | 9/2003 |
| WO | WO-03/082289 | 10/2003 |
| WO | WO-03/082868 | 10/2003 |
| WO | WO-03/082869 | 10/2003 |
| WO | WO-03/062236 | 12/2003 |
| WO | WO-03/087087 | 12/2003 |
| WO | WO-03/101990 | 12/2003 |
| WO | WO-2004/005283 | 1/2004 |
| WO | WO-2004/009600 | 1/2004 |
| WO | WO-2004/009601 | 1/2004 |
| WO | WO-2004/014369 | 2/2004 |
| WO | WO-2004/016609 | 2/2004 |
| WO | WO-2004/016610 | 2/2004 |
| WO | WO-2004/024895 | 3/2004 |
| WO | WO-2004/052880 | 6/2004 |
| WO | WO-2004/054581 | 7/2004 |
| WO | WO-2004/056830 | 7/2004 |
| WO | WO-2004/065393 | 8/2004 |
| WO | WO-2004/065394 | 8/2004 |
| WO | WO-2004/069138 | 8/2004 |
| WO | WO-2004/054974 | 9/2004 |
| WO | WO-2004/074278 | 9/2004 |
| WO | WO-2004/074286 | 9/2004 |
| WO | WO-2004/078756 | 9/2004 |
| WO | WO-2004/078923 | 9/2004 |
| WO | WO-2004/101565 | 11/2004 |
| WO | WO-2005/005426 | 1/2005 |
| WO | WO-2005/028475 | 3/2005 |
| WO | WO-2005/028624 | 3/2005 |
| WO | WO-2005/030128 | 4/2005 |
| WO | WO-2005/030709 | 4/2005 |
| WO | WO-2005/034869 | 4/2005 |
| WO | WO-2005/044181 | 5/2005 |
| WO | WO-2005/058891 | 6/2005 |
| WO | WO-2005/062795 | 7/2005 |
| WO | WO-2005/063746 | 7/2005 |
| WO | WO-2005/063747 | 7/2005 |
| WO | WO-2005/066347 | 7/2005 |
| WO | WO-2005/082367 | 9/2005 |
| WO | WO-2005/085244 | 9/2005 |
| WO | WO-2005/086904 | 9/2005 |
| WO | WO-2005/092896 | 10/2005 |
| WO | WO-2005/095400 | 10/2005 |
| WO | WO-2005/103050 | 11/2005 |
| WO | WO-2005/115363 | 12/2005 |
| WO | WO-2005/115374 | 12/2005 |
| WO | WO-2005/116035 | 12/2005 |
| WO | WO-2006/004984 | 1/2006 |
| WO | WO-2006/009755 | 1/2006 |
| WO | WO-2006/009797 | 1/2006 |
| WO | WO-2006/010637 | 2/2006 |
| WO | WO-2006/015123 | 2/2006 |
| WO | WO-2006/015124 | 2/2006 |
| WO | WO-2006/063167 | 6/2006 |
| WO | WO-2006/114180 | 11/2006 |
| WO | WO-2006/114520 | 11/2006 |
| WO | WO-2006/127587 | 11/2006 |
| WO | WO-2006/137376 | 12/2006 |
| WO | WO 2007/002325 | 1/2007 |
| WO | WO 2007/002433 | 1/2007 |
| WO | WO-2007/009799 | 1/2007 |
| WO | WO-2007/013896 | 2/2007 |
| WO | WO-2007/022380 | 2/2007 |
| WO | WO-2007/106236 | 9/2007 |
| WO | WO-2008/058341 | 5/2008 |
| WO | WO-2008/065417 | 6/2008 |
| WO | WO-2008/063888 | 7/2008 |
| WO | WO-2008/079906 | 7/2008 |
| WO | WO-2008/079909 | 7/2008 |
| WO | WO-2008/064255 | 8/2008 |
| WO | WO-2008/076779 | 8/2008 |
| WO | WO-2008/064265 | 11/2008 |
| WO | WO-2008/138755 | 11/2008 |
| WO | WO-2009/012283 | 1/2009 |
| WO | WO-2009/012791 | 1/2009 |
| WO | WO-2009/111277 | 9/2009 |
| WO | WO-2009/111278 | 9/2009 |
| WO | WO-2009/111279 | 9/2009 |
| WO | WO-2009/111280 | 9/2009 |
| WO | WO-2009/115084 | 9/2009 |
| WO | WO-2009/143024 | 11/2009 |
| WO | WO-2010/020905 | 2/2010 |
| WO | WO-2010/059658 | 5/2010 |
| WO | WO-2010/104945 | 9/2010 |
| WO | WO-2010/104973 | 9/2010 |
| WO | WO-2010/114928 | 10/2010 |
| WO | WO 2010/129567 | 11/2010 |
| WO | WO-2011/015522 | 2/2011 |
| WO | WO 2011/060216 | 5/2011 |
| WO | WO-2011/063159 | 5/2011 |

(56) References Cited

FOREIGN PATENT DOCUMENTS

| WO | WO 2011/079133 | 6/2011 |
|---|---|---|
| WO | WO-2011/079133 | 6/2011 |
| WO | WO-2011/133637 | 10/2011 |
| WO | WO 2012/032236 | 3/2012 |
| WO | WO-2012/037060 | 5/2012 |
| WO | WO-2012/138809 | 10/2012 |
| WO | WO-2012/158957 | 11/2012 |
| WO | WO-2012/161776 | 11/2012 |

OTHER PUBLICATIONS

Arbiser, "Why targeted therapy hasn't worked in advanced cancer," *The Journal of Clinical Investigation*, (2007), 117(10):2762-2765.
Alvarez, et al., "Synthesis of 3-Aryl- and 3-Heteroaryl-7-Azaindoles," *Synthesis*, (1999), 4:615-620.
Amersdorfer, et al., "Phage Libraries for Generation of Anti-Botulinum scFv Antibodies," *Methods in Molecular Biology*, (2000), 145:219-240.
Amiel, et al., "Hirschsprung disease, associated syndromes and genetics: a review," *J Med Genet.*, (2008), 45:1-14.
Anderson, et al., "Cooperative Catalyst Effects in Palladium-Mediated Cyanation Reactions of Aryl Halides and Triflates," *J. Org. Chem.*, (1998), 63:8224-8228.
Antonini, et al., "Synthesis of 4-Amino-1-β-D-Ribofuranosyl-1H-pyrrolo[2,3-b]pyridine (1-Deazatubercidin) as a Potential Antitumor Agent," *J. Med. Chem.*, (1982), 25:1258-1261.
Arthan et al., "Leukemia inhibitory factor can mediate Ras/Raf/MEK/ERK-induced growth inhibitory signaling in medullary thyroid cancer cells," *Cancer Letters* (2010), 297:31-41.
Ashman, et al., "The biology of stem cell factor and its receptor C-kit," *The International Journal of Biochemistry & Cell Biology*, (1999), 31:1037-1051.
Baghestanian, et al., "A Case of Malignant Mastocytosis with Circulating Mast Cell Precursors: Biologic and Phenotypic Characterization of the Malignant Clone," *Leuk.*, (1996), 10:159-166.
Bagshaw et al., "Measurement of Ligand Binding to Proteins," *Spectrophotometry and Spectrofluorimetry: A Practical Approach*, (1987), 4:91-113.
Bagshawe, K., "Antibody-Directed Enzyme Prodrug Therapy: A Review," *Drug Dev. Res.*, (1995), 34:220-230.
Balak, et. al., "Novel D761Y and Common Secondary T790M Mutations in Epidermal Growth Factor Receptor 13 Mutant Lung Adenocarcinomas with Acquired Resistance to Kinase Inhibitors," *Clin Cancer Res.*, (2006), 12:6494-501.
Bancalari, et al., "Blood Markers of Early and Late Airway Responses to Allergen in Asthmatic Subjects. Relationship with Functional Findings," *Allergy*, (1997), 52:32-40.
Banker, G.S. et al, "Modern Pharmaceutics, 3ed.", *Marcel Dekker*, New York, (1996), p. 596.
Bartlett, et al., "CAVEAT: A Program to Facilitate the Structure-Derived Design of Biologically Active Molecules," *Royal Society of Chemistry*, (1989), 78:I80-I96.
Barton, et al., "The chemistry of pentavalent organobismuth reagents. Part X. Studies on the phenylation and oxidation of phenols," *Tetrahedron*, (1987), 43(2):323-332.
Bashford, et al., "Measurement of Ligand Binding to Proteins," *Spectrophotometry and Spectrofluorimetry: A Practical Approach*, (1987), 4:91-113.
Basta, et al., "High-dose Intravenous Immunoglobulin Exerts Its Beneficial Effect in Patients with Dermatomyositis by Blocking Endomysial Deposition of Activated Complement Fragments," *J Clin Invest.*, (1994), 94:1729-1735.
Basto, et al., "Mutation analysis of B-RAF gene in human gliomas," *Acta Neuropathol.*, (2005), 109:207-210.
Bayindir et al., "Cellular mesoblastic nephroma (infantile renal fibrosarcoma): institutional review of clinical, diagnostic imaging, and pathologic features of a distinctive neoplasm of infancy," *Pediatr. Radiol.*, (2009), 39(10):1066-74.
Beaucage et al., "Advances in Synthesis of Oligonucleotides by the Phosphoramidite Approach," *Tetrahedron*, (1992), 48:2223-2311.

Bedi, et al., "BCR-ABL-Mediated Inhibition of Apoptosis With Delay of G2/M Transition After DNA Damage: A Mechanism of Resistance to Multiple Anticancer Agents," *Blood*, (1995), 86:1148-1158.
Bell, J.E., "Fluorescence: Solution Studies" *Spectroscopy in Biochemistry*, vol. I, (1981),(4):155-194.
Bellone, et al., "Growth Stimulation of Colorectal Carcinoma Cells Via the c-Kit Receptor is Inhibited by TGF-β1," *J. Cell Physiol.*, (1997), 172:1-11.
Berdel, et al., "Recombinant Human Stem Cell Factor Stimulates Growth of a Human Glioblastoma Cell Line Expressing c-kit Protooncogene," *Canc. Res.*, (1992), 52:3498-3502.
Bertolini, et al., "A New Rational Hypothesis for the Pharmacophore of the Active Metabolite of Leflunomide, a Potent Immunosuppressive Drug," *J. Med. Chem.*, (1997), 40:2011-2016.
Bjorntrop, "Neuroendocrine Pertuirbations as a Cause of Insulin Resistance," *Diabetes Metab. Res. Rev.*, (1999), 15:427-441.
Bloom, et al., "The Preparation of 2-Alkylaminobenzimidazoles," *J. Org. Chem.*, (1939), 14-19.
Blundell, et al., "Knowledge-Based Protein Modelling and Design," *Eur. J. Biochem.*, (1988), 172:513-520.
Bode, et al., "Mutations in the tyrosine kinase domain of the EGFR gene are rare in synovial sarcoma," *Modern Pathology*, (2006), 19:541-547.
Bohm, H.-J., "On the Use of LUDI to Search the Fine Chemicals Directory for Ligands of Proteins of Known Three-Dimensional Structure," *J. Comp. Aided Molec. Design*, (1994), 8:623-632.
Bokenmeyer, et al., "Expression of Stem-Cell Factor and Its Receptor c-kit Protein in Normal Testicular Tissue and Malignant Germ-Cell Tumours," *J. Cancer Res. Clin. Oncol.*, (1996), 122:301-306.
Bolger, et al., "Computer Modeling of Combining Site Structure of Anti-Hapten Monoclonal Antibodies," *Methods Enz.*, (1991), 203:21-45.
Bongarzone, et al., "High Frequency of Activation of Tyrosine Kinase Oncogenes in Human Papillary Thyroid Carcinoma," *Oncogene*, (1989), 4(12):1457-1462.
Bothwell, M., "Keeping Track of Neurotrophin Receptors," *Cell*, (1991), 65:915-918.
Bouzakri, et al., "MAP4K4 Gene silencing in Human Skeletal Muscle Prevents Tumor Necrosis Factor-a-induced Insulin Resistance," *J. Biol. Chem.*, (2007), 282:7783-7789.
Bouzas-Rodriguez et al., Neurotrophin-3 production promotes human neuroblastoma cell survival by inhibiting TrkC-induced apoptosis, *J. Clin. Invest.*, 120(3):850-8 (2010).
Bundgaard, "Design of produdrugs: Bioreversible derivatives for various functional groups and chemical entitites," *Design of Produgs*,(1985), p. 1.
Bowtell, D., "Options Available From Start to Finish for Obtaining Expression Data by Microarray," *Nature Genetics Supp.*, (1999), 21:25-32.
Breindl, "No Melanocyte is an Island: In Melanoma, Interfeon, Roles Need Rethinking," *BioWorld Today*, (2011), 22(17): 1;5.
Brenner, et al., "Encoded Combinatorial Chemistry," *Proc. Natl. Acad. Sci. USA*, (1992), 89:5381-5383.
Broudy, V., "Stem Cell Factor and Hematopoiesis," *Blood*, (1997), 90:1345-1364.
Brunger, A. T., "Free R Value: a Novel Statistical Quantity for Assessing the Accuracy of Crystal Structures," *Nature*, (1992), 355:472-475.
Burns et al., "c-FMS Inhibitars: A Patent Review," *Expert Opinion Ther. Patents*, (2011), 21(2):147-165.
Calabresi, et al., "Section IX: Chemotherapy of neoplastic diseases," *Goodman & Gilman's The Pharmacological Basis of Therapeutics, Tenth Edition, McGraw-Hill Medical Publishing Division*, (2001), pp. 1381, 1383-1385 and 1388.
Capon, et al., "Designing CD4 Immunoadhesins for AIDS Therapy," *Nature*, (1989), 337:525-531.
Carell, et al., "New Promise in Combinatorial Chemistry: Synthesis, Characterization, and Screening of Small-Molecule Libraries in Solution," *Chem. Biol.*, (1995), 2:171-183.
Carpino, et al., "p62dok: A Constitutively Tyrosine-Phosphorylated, GAP-Associated Protein in Chronic Myelogenous Leukemia Progenitor Cells," *Cell*, (1997), 88:197-204.

(56) References Cited

OTHER PUBLICATIONS

Castelle, et al., "The Presence of Membrane-Bound Stem Cell Factor on Highly Immature Nonmetachromatic Mast Cells in the Peripheral Blood of a Patient with Aggressive Systemic Mastocytosis," *J. Aller. Clin. Immunol.*, (1996), 98:831-840.

Castellone, et al., "A novel de novo germ-line V292M mutation in the extracellular region of RET in a patient with phaeochromocytoma and medullary thyroid carcinoma: functional characterization," *Clinical Endocrinology*, (2010), 73:529-534.

Chabala, J., "Solid-Phase Combinatorial Chemistry and Novel Tagging Methods for Identifying Leads," *Curr Opin Biotechnol.*, (1995), 6:632-639.

Chappell et al., "Ras/Raf/MEK/ERK and PI3K/PTEN/Akt/Mtor Inhibitors: Rationale and Importance to Inhibiting These Pathways in Human Health," *Oncotarget*, (2011), 2(3):135-164.

Chayer, et al., "Synthesis of Carboranylpyrroles," *Tetrahedron Lett.*, (2001), 42(44):7759-7761.

Checovich, et al., "Fluorescence Polarization—a New Tool for Cell and Molecular Biology," *Nature*, (1995), 375:254-256.

Chou, et al., "Chemotherapeutic Synergism, Potentiation and Antagonism," *Encyclopedia of Human Biology, Academic Press*, (1991), 2:371-379.

Chou, et al., "Computerized Quantitation of Synergism and Antagonism of Taxol, Topotecan, and Cisplatin Against Human Teratocarcinoma Cell Growth: a Rational Approach to Clinical Protocol Design," *J. Natl. Cancer Inst.*, (1994), 86:1517-1524.

Chou, et al., "Quantitative analysis of Dose-Effect Relationships: The Combined Effects of Multiple Drugs or Enzyme Inhibitors," *Adv. Enzyme Regul.*, (1984), 22:27-55.

Chou, et al., "Synergism and Antagonism in Chemotherapy," *Academic Press*, (1991), Chapter 2:61-102.

Clark, et al., "Pro_Ligand: An Approach to De Novo Molecular Design. 1. Application to the Design of Organic Molecules," *J. Comp. Aided Molec. Design*, (1995), 9:13-32.

Clohisy, et al., "Review of Cellular Mechanisms of Tumor Osteolysis," *Clin. Orthop.*, (2000), 373:104-114.

Coe, et al., "Solution-Phase Combinatorial Chemistry," *Mol Divers.*, (1999), 4:31-38.

Coelho, et al., "Studies of RET gene expression and acetylcholinesterase activity in a series of sporadic Hirschsprung's disease," *Pediatr Surg Int*, (2008), 24:1017-1021.

Cohen, et al., "Expression of Stem Cell Factor and C-Kit in Human Neuroblastoma," *Blood*, (1994), 84:3465-3472.

Collins, et al., "A small interfereing RNA screen for modulators of tumor cell motility identifies MAP4K4 as a prommigratory kinase," *Proc. Natl. Acad. Sci. USA*, (2006), 103:3775-3780.

Collioud, et al., "Oriented and Covalent Immobilization of Target Molecules to Solid Supports: Synthesis and Application of a Light-Activatable and Thiol-Reactive Cross-Linking Reagent," *Bioconjugate Chem.*, (1993), 4:528-536.

Colman, P.M., "Structure-Based Drug Design," *Current Opinion in Struc. Biol.*, (1994), 4:868-874.

Columbo, et al., "The Human Recombinant c-kit Receptor Ligand, rhSCF, Induces Mediator Release From Human Cutaneous Mast Cells and Enhances IgE-Dependent Mediator Release From Both Skin Mast Cells and Peripheral Blood Basophils," *J. Immunol.*, (1992), 149:599-608.

Coniglio, et al., "Microglial stimulation of glioblastoma invasion involves epidermal growth factor receptor (EGFR) and colony stimulating factor 1 receptor (CSF-1R) signaling," *Mol. Med.*, (2012), 18: 519-527.

Costa, et al., "The Cells of the Allergic Response," *JAMA*, (1997), 278:1815-1822.

Coste, et al., "Coupling N-Methylated Amino Acids Using PyBroP1 and PyCloP Halogenophosphonium Salts: Mechanism and Fields of Application," *Journal of Organic Chemistry*, (1994), 59:2437-2446.

Coulie, et al., "Recombinant Human Neurotropic Factors Accelerate Colonic Transit and Relieve Constipation in Humans," *Gastroenterology*, (2000), 119:41-50.

Crouch, et al., "The use of ATP bioluminescence as a measure of cell proliferation and cytotoxicity," *Journal of Immunological Methods*, (1993), 160:81-88.

Crump, M., "Inhibition of Raf Kinase in the Treatment of Acute Myeloid Leukemia," *Curr. Pharm. Design*, (2002), 8(25):2243-2248.

Curtin, et al., "Discovery and Evaluation of a Series of 3-Acylindole Imidazopyridine Platelet-Activating Factor Antagonists," *J. Med. Chem.*, (1998), 41:74-95.

Curtin, et al., "Somatic activation of KIT in distinct subtypes of melanoma," *J. of Clinical Oncology*, (2006), 24(26): 4340-4345.

Cwirla, et al., "Peptides on Phage: A Vast Library of Peptides for Identifying Ligands," *Biochemistry*, (1990), 87:6378-6382.

Dai, et al., "Targeted disruption of the mouse colony-stimulating factor 1 receptor gene results in osteopetrosis, mononuclear phagocyte deficiency, increased primitive progenitor cell frequencies, and reproductive defects," *Blood*, (2002), 99:111-120.

Damasio, "Alzheimer's Disease and Related Dementias," Cecil Textbook of Medicine, 20$^{th}$ Edition, (1996), 2:1992-1996.

Dandliker, et al., "Equilibrium and Kinetic Inhibition Assays Based Upon Fluorescence Polarization," *Methods in Enzymology*, (1981), 74:3-28.

Das-Gupta et al., "Acridine Derivatives, Part VI," *J. Indian Chem. Society*, (1941), 18:25-28.

Dastych, et al., "Stem Cell Factor Induces Mast Cell Adhesion to Fibronectin," *J. Immunol.*, (1994), 152:213-219.

Davies, et al., "Mutations of the BRAF gene in human cancer," *Nature*, (2002), 417:949-954.

Demetri, G.D., "Targeting c-kit mutations in solid tumors: Scientific rationale and novel therapeutic options," *Seminars in Oncology*, (2001), 28(5), Supp. 17:19-26.

Denardo, et al., "Leukocyte complexity predicts breast cancer survival and functionally regulates response to chemotherapy," *Cancer Discovery*, (2011), 54-67.

Dewar, et al., "Inhibition of c-fms by Imatinib Expanding the Spectrum of Treatment," *Cell Cycle*, (2005), 4(7):851-853.

Dolle, et al., "Comprehensive Survey of Combinatorial Library Synthesis: 1998," *J. Comb. Chem.*, (1999), 1:235-282.

Dong, et al., "BRAF Oncogenic Mutations Correlate with Progression rather than Initiation of Human Melanoma," *Cancer Research*, (2003), 63:3883-3885.

Donis-Keller, et al., "Mutations in the RET Proto-Oncogene are Associated with MEN 2A and FMTC," *Hum Mol Genet.*, (1993), 2(7):851-856.

Dorwald, "Side Reactions in Organic Synthesis: A Guide to Successful Synthesis Design," *Wiley-VCH*, (2005), Preface p. IX.

Douma, et al., "Suppression of anoikis and induction of metastasis by the neurotropic receptor TrkB," *Nature*, (2004), 430:1034-1039.

Doyle, eta al., "Alkyl Nitrite-metal halide Deamination Reactions. 6. Direct Synthesis of Arenediazonium Tetrafluoroborate Salts from Aromatic Amines, tert-Butyl Nitrite, and Boron Trifluoride Etherate in Anhydrous Media," *J. Org. Chem.*, (1979), 44:1572.

Dube, et al., "Reductive N-Alkylation of Amides, Carbamates and Ureas," *Tetrahedron Lett.*, (1999), 40:2295-2298.

Dumas, "Protein kinase inhibitors: emerging pharmacophores 1997-2000," *Exp. Opin. Ther. Patents*, (2001), 11 (3): 405-429.

Durbec, et al., "GDNF Signalling Through the Ret Receptor Tyrosine Kinase," *Nature*, (1996), 381:789-793.

Dutcher et al., "Studies of the C11H8N2OS Degradation Product of Gliotoxin," *J. Am. Chem. Soc.*, (1951), 73:4139-4141.

Dyson, et al., "The Human Papilloma Virus 13 16 E7 Oncoprotein is Able to Bind to the Retinoblastoma Gene Product," *Science*, (1989), 243:934-937.

Eklund, et al., "Treatment of rheumatoid arthritis with imatinib mesylate: clinical improvements in three refractory cases," *Annals of Medicine*, (2003), 35:362-367.

Eliseev, et al., "Dynamic Combinatorial Chemistry: Evolutionary Formation and Screening of Molecular Libraries," *Current Topics in Microbiology & Immunology*, (1999), 243:159-172.

Engelman et al., "Effective use of PI3K and MEK inhibitors to treat mutant Kras G12D and PIK3CA H1047R murine lung cancers," *Nature Medicine*, (2008), 14(12):1351-1356.

(56) References Cited

OTHER PUBLICATIONS

Enjalbal, et al., "Mass Spectrometry in Combinatorial Chemistry," *Mass Spectrometry Reviews*, (2000), 19:139-161.
Ertl et al., "Fast calculation of molecular polar surface area as a sum of fragment-based contributions I I and its application to the prediction of drug transport properties" *J Med Chem*, (2000), 43:3714-3717.
Escribano, et al.,""Expression of the c-kit (CD117) Molecule in Normal and Malignant Hematopoiesis"" *Leuk. Lymph.*, (1998), 30:459-466.
Felder, E.R., ""The Challenge of Preparing and Testing Combinatorial Compound Libraries in the Fast Lane, at the Front End of Drug Development"" *Chimia.*, (1994), 48:531-541.
Feng, et al.,""Stable in Vivo Gene Transduction Via a Novel Adenoviral/Retroviral Chimeric Vector"" *Nature Biotechnology*, (1997), 15:866-870.
Finotto, et al.,""Glucocorticoids Disease Tissue Mast Cell Number by Reducing the Production of the c-kit Ligand, Stem Cell Factor, by Resident Cells"" *J. Clin. Invest.*, (1997), 99:1721-1728.
Fischer et al.,""Targeting receptor tyrosine kinaseandomizeg in small cell lung cancer (SCLC): What have we learned so far?"" *Cancer Treatment Reviews*, (2007), 33:391-406.
Flanagan et al.,""Macrophages and the arious isoforms of macrophage colony-stimulating factor"" *Curr Opin Hematol.*, (1998), 5:181-5.
Franz, et al.,""Sulfuranes. X. A Reagent for the Facile Cleavage of Secondary Amides""0 *JACS*, (1973), 95(6):2017-2019.
Friesen et al.,""Hydroxypropyl Methylcellulose Acetate Succinate-Based Spray-Dried Dispersions: An Overview"" *Molecular Pharmaceutics*, (2008), 5(6):1003-1019.
Furitsu, et al.,""Identification of Mutations in the Coding Sequence of the Proto-oncogene c-kit in a Human Mast Cell Leukemia Cell Line Causing Ligand-independent Activation of the c-kit Product"" *J. Clin. Invest.*, (1993), 92:1736-1744.
Furuta, et al.,""Stem Cell Factor Influences Mast Cell Mediator Release in Response to Eosinophil-Derived Granule Major Basic Protein"" *Blood*, (1998), 92:1055-1061.
Gallego et al.,""Increased opioid dependence in a mouse model of panic disorder"" *Front Behav. Neurosci.*, (2010), 3:60.
Gallop, et al.,""Applications of Combinatorial Technologies to Drug Discovery. 1. Background and Peptide Combinatorial Libraries"" *J. Med. Chem.*, (1994), 37:1233-1251.
Galofre, et al.,""Evaluation and Treatment of Thyroid Nodules: A Clinical Guide"" *Mt Sinai J Med.*, (2008), 75:299-311.
Garzya et al.,""Indium(III)-catalysed aryl sulfonylation reactions"" *Tetrahedron Letters*, (2004), 45:1499-1501.
Gassman, et al.,""Specific Ortho Substitution of Aromatic Heterocyclic Amines"" *J Am Chem Society*, (1973), 95(13):4453-4455.
Ghebre-Sellassie, Isaac; Martin, Charles.,""Pharmaceuticast Extrusion Technology"" *Marcer Dekker, Inc., New York. Basel. CRC Press*, (2003), p. 238.
Gimbel, et al.,""Braf mutations are associated with increased mortality in colorectal cancer"" *Journal of the American College of Surgeons*, (2004), 199:S91-S92.
Girgis, et.al.,""The Synthesis of 5-Azaindoles by Substitution-Rearrangement of 7-Azaindoles upon Treatment with Certain Primary Amines"" *J. Heterocyclic. Chem.*, (1989), 26:317-325.
Golkar, et al.,""Mastocytosis"" *Lancet*, (1997), 349:1379-1385.
Golub, et al.,""Molecular Classifcation of Cancer: Class Discovery and Class Prediction by Gene Expression Monitoring"" *Science*, (1999), 286:531-537.
Goodford, P.J.,""A Computational Procedure for Determining Energetically Favorable Binding Sites on Biologically Important Macromolecules"" *J. Med. Chem.*, (1985), 28:849-857.
Goodsell, et al.,""Automated Docking of Substrates to Proteins by Simulated Annealing"" *Proteins: Structure, Function, and Genetics*, (1990), 8:195-202.
Gordon et al.,""Detection of Peroxides and Their Removal"" *The Chemis"s Companion: A Handbook of Practical Data, Techniques, and References*, (1972), p. 437.

Gordon, et al.,""Applications of Combinatorial Technologies to Drug Discovery. 2. Combinatorial Organic Synthesis, Library Screening Strategies, and Future Directions"" *J. Med. Chem.*, (1994), 37:1385-1401.
Gram, H.,""Phage Display in Proteolysis and Signal Transduction"" *Combinatorial Chemistry & High Throughput Screening*, (1999), 2:19-28.
Gravert, et al.,""Synthesis on Soluble Polymers: New Reactions and the Construction of Small Molecules"" *Curr Opin Chem Biol.*, (1997), 1:107-113.
Greer, J.,""Model Structure for the Inflammatory Protein C5a"" *Science*, (1985), 228:1055-1060.
Grieco, et al.,""PTC is a Novel Rearranged Form of the ret Proto-Oncogene and is Frequently Detected in Vivo in Human Thyroid Papillary Carcinomas"" *Cell*, (1990), 60(4):557-563.
Guida, W.,""Software for Structure-Based Drug Design"" *Current Opinion in Struc. Biol.*, (1994), 4:777-781.
Gura,""Systems for identifying New Drugs Are Often Faulty, Cancer Models"" *Science*, (1997), 278(5340):1041-1042.
Hafner, et al.,""Isothermal Amplification and Multimerization of DNA by Bst DNA Polymerase"" *Biotechniques*, (2001), 30(4):852-867.
Hallek, et al.,""Interaction of the Receptor Tyrosine Kinase p145c-kit with the p210bcr/abl Kinase in Myeloid Cells"" *Brit. J Haem.*, (1996), 94:5-16.
Halvorson, et al.,""A Blocking Antibody to Nerve Growth Factor Attenuates Skeletal Pain Induced by Prostate Tumor Cells Growing in Bone"" *Cancer Res.*, (2005), 65:9426-9435.
Hamel, et al.,""The Road Less Traveled: c-kit and Stem Cell Factor"" *J. Neuro-Onc.*, (1997), 35:327-333.
Hancock et al.,""Characteristics and Significance of the Amorphous State in Pharmaceutical Systems"" *Journal of Pharmaceutical Sciences*, (1997), 86(1):1-12.
Hands, et al.,""A convenient Method for the Preparation of 5-, 6- and 7-Azaindoles and Their Derivatives"" *Synthesis*, (1996), 877-882.
Hanselman, et al.,""A CdnA-Dependant Scintillation Proximity Assay for Quantifying Apolipoprotein A1"" *J. Lipid Res.*, (1997), 38:2365-2373.
Hasegawa et al.,""Visualizing Mechanosensory Endings ofTrkC-Expressing Neurons in HS3ST-2-HplaP Mice"" *J Comp. Neurol.*, (2008), 511(4):543-556.
Hassan, et al.,""Expression of Protooncogene c-kit and Its Ligand Stem Cell Factor (SCF) in Gastric Carcinoma Cell Lines"" *Digest. Dis. Science*, (1998), 43:8-14.
Hassan, et al.,""Stem Cell Factor as a Survival and Growth Factor in Human Normal and Malignant Hematopoiesis"" *Acta. Hem.*, (1996), 95:257-262.
Hayashi, et al.,""Dichloro[1,1 19-bis(diphenylophosphino)ferrocene]palladium-(II), An Effective Catalyst for Cross-Coupling of Secondary and Primary Alkyl Grignard and Alkylzinc Reagents with Organic Halides"" *J. Am. Chem. Soc.*, (1984), 106:158-163.
Haydock et al.,""Analogues of clofibrate and clobuzarit containing fluorine in the side chains"" *Eur. J. Med. Chem.*, (1984), 19(3):205-214.
He et al. "c-Fms Signaling Mediates Neurofibromatosis Type-1 Osteoclast Gain-In-Functions," *PLoS ONE*, (2012), 7(11): 1-9.
He, et al.,""Gamma-secretase activating protein, a therapeutic target for Alzheime"s disease"" *Nature*, (2010), 467(7311):95-98.
Heacock, et al.,""Orientation and Relative Reaction rate Factors in aromatic Substitution by the Benzensulfonimido Radical"" *J. Am. Chem. Soc.*, (1960), 82:3460-3463.
Heim, et al.,""Engineering Green Fluorescent Protein for Improved Brightness, Longer Wavelengths and Fluorescence Resonance Energy Transfer"" *Curr. Biol.*, (1996), 6:178-182.
Heinrich, et al.,""PDGFRA Activating Mutations in Gastrointestinal Stromal Tumors"" *Science*, (2003), 299:708-710.
Heinrich, M. C. et al., "Inhibition of KIT Tyrosine Kinase Activity: A Novel Molecular Approach to the Treatment of KIT-Positive Malignancies," *J. Clin. Oncol.*, (2002), 20(6):1692-1703.
Hentschel et al.,""BCR-ABL-and Ras-independent activation of Raf as a novel mechanism of Imatinib resistance in CML"" (2012), http://www.ncbi.nlm.nih.gov/pubmed/2163917.

(56) References Cited

OTHER PUBLICATIONS

Herbst, et al.,""Differential Effects of W Mutations on p145c-kit Tyrosine Kinase Activity and Substrate Interaction"" *J. Biol. Chem.*, (1992), 267:13210-13216.
Hibi, et al.,""Coexpression of the stem cell factor and the c-kit genes in small-cell lung cancer"" *Oncogene*, (1991), 6:2291-2296.
Hirota, et al.,""Gain-of-function Mutations of c-kit in Human Gastrointestinal Stromal Tumors"" *Science*, (1998), 279:577-580.
Hoffmann,""m-Trifluoromethylbenzenesulfonyl Chloride"" *Organic Syntheses*, (1981), 60:121-126.
Hogaboam, et al.,""Novel Role of Transmembrane SCF for Mast Cell Activation and Eotaxin Production in Mast Cell-Fibroblast Interactions"" *J. Immunol.*, (1998), 160:6166-6171.
Holmes, et al.,""Long-term effects of Aβ42 immunisation in Alzheime"s disease: follow-up of aandomizedd, placebo-controlled phase I trail"" *Lancet* (2008) 372:216-233.
Hood, et al.,""Tumor Regression by Targeted Gene Delivery to the Neovasculature"" *Science*, (2002), 296: 2404-2407.
Houghten, et al.,""Generation and Use of Synthetic Peptide Combinatorial Libraries for Basic Research and Drug Discovery"" *Nature*, (1991), 354:84-86.
Houghten, R.,""Parallel Array and Mixture-Based Synthetic Combinatorial Chemistry: Tools for the Next Millennium"" *Annu Rev Pharmacol Toxicol.*, (2000), 40:273-282.
Houghten, R.,""Peptide Libraries: Criteria and Trends"" *Trends Genet.*, (1993), 9:235-239.
Hudson, et al.,""A Simple Method for the Determination of Serum Acid Phosphatase"" *J. Urology*, (1947), 58:89-92.
Hughes-Jones, et al.,""Synthesis of Rh Fv Phage-Antibodies Using VH and VL Germline Genes"" *British Journal of Haematology*, (1999), 105:811-816.
Ibrahim et al.,""Pyrrolo[2,3-b]pyridine derivatives as protein kinase inhibitors and their preparation, pharmaceutical compositions and use in the treatment of diseases"" *Caplus*, (2007) 11300.
Iemura, et al.,""The c-kit Ligand, Stem Cell Factor, Promotes Mast Cell Survival by Suppressing Apoptosis"" *Amer. J. Pathol.*, (1994), 144:321-328.
Inoue, et al.,""Coexpression of the c-kit Receptor and the Stem Cell Factor in Gynecological Tumors"" *Cancer Res.*, (1994), 54:3049-3053.
International Search Report and Written Opinion for PCT/US2013/03400 dated Jul. 22, 2013.
International Search Report and Written Opinion dated Mar. 31, 2012 for PCT Patent Application No. PCT/US2012/025965.
International Search Report and Written Opinion dated May 7, 2013 for PCT Patent Application No. PCT/US2013/032835.
International Search Report and Written Opinion dated Jul. 22, 2013 for PCT Patent Application No. PCT/US2013/0043400.
Isbel, et al., "Local macrophage proliferation correlates with increased renal M-CSF expression in human glomerulonephritis," *Nephrol Dial Transplant*, (2001), 16:1638-1647.
Ishizaka, et al., "Human ret Proto-Oncogene Mapped to Chromsome 10q11.2," *Oncogene*, (1989), 4(12):1519-1521.
Isozaki, et al., "Deficiency of c-kit cells in patients with a myopathic form of chronic idiopathic intestinal pseudo-obstruction," *Amer. J. of Gast.*, (1997), 9:332-334.
Ivanisevic et al., "Uses of X-Ray Powder Diffraction in the Pharmaceutical Industry," *Pharm Sci Encyc:DDDM*, (2010), pp. 1-42.
Mane, et al., "Myosin Subfragment-1 is Fully Equipped with Factors Essential for Motor Function," *Biochem. and Biophys. Res. Comm.*, (1997), 230:76-80.
Izquierdo, et al., "Differential Expression of the c-kit Proto-Oncogene in Germ Cel Tumours," *J. Pathol.*, (1995), 177:253-258.
Jaiswal et al., Combined Targeting of BRAF and CRAF or BRAF and PI3K Effector Pathways is Required for Efficacy in NRAS Mutant Tumors, *PLoS One*, (2009), 4(5):e5717.
Jensen, et al., "Pharmacological targeting of the KIT growth factor receptor: a therapeutic consideration for mast cell disorders," *Brit J Pharmacology*, (2008), 154:1572-1582.

Jing, et al., "GDNF-Induced Activation of the Ret Protein Tyrosine Kinase is Mediated by GDNFR-a, a Novel Receptor for GDNF," *Cell*, (1996), 85:1113-1124.
Johnson et al., Relationships between drug activity in NCI preclinical in vitro and in vivo models and early clinical trials, *British Journal of Cancer*, (2001), 64(10): 1424-1431.
Johnston, M., "Gene Chips: Array of hope for understanding gene regulation," *Curr. Biol.*, (1998), 8:R171-R174.
Jones, et al., "Antiestrogens. 2. Structure-Activity Studies in a Series of 3-Aroyl-2-arylbenzo[b]thiophene Derivatives Leading to [6-Hydroxy-2-(4-hydroxyphenyl)benzo(b)thien-3-yl](4-[2-(1-piperidinyl)ethoxy]-phenyl]methanone Hydrochloride (LY156758), a Remarkably Effective Estrogen Antagonist with Only Minimal Intrinsic Estrogenicity," *J. Med. Chem.*, (1984), 27(8):1057-1066.
Jones, R., "Biology and Treatment of Chronic Myeloid Leukemia," *Curr. Opin. Onc.*, (1997), 9:3-7.
Jones, T., "Interactive Computer Graphics: FRODO," *Methods in Enzymology*, (1985), 115:157-171.
Jongh et al. "The Role of Interleukin-6 in Nociception and Pain," *Anesth Analg*, (2003), (96):1096-103.
Jose, et al., "Blockade or Macrophage colony-Stimulating Factor Reduces Macrophage Proliferation and Accumulation in Renal Allograft Rejection," *Am J Transplant*, (2003), 3(3):294-300.
Joseph-McCarthy, D., "Computational Approaches to Structure-Based Ligand Design," *Pharmacology & Therapeutics*, (1999), 84:179-191.
Joule et al., "Indole and its Derivatives," *Science of Synthesis*, (2001), 10:618-652.
Kahl, et al., "A Multiple-Approach Scintillation Proximity Assay to Measure the Association Between Ras and Raf," *Anal. Biochem.*, (1996), 243:282-283.
Kassel, et al., "Local increase in the number of mast cells and expression of nerve growth factor in the bronchus of asthmatic patients after repeated inhalation of allergen low-dose," *Clin. Exp. Allergy*, (2001), 31:1432-1440.
Katritzky, et al., "Regiospecific C-Acylation of Pyrroles and Indoles Using N-Acylbenzotriazoles," *J. Org. Chem.*, (2003), 68:5720-5723.
Kay, et al., "Eosinophils and Eosinophil-Associated Cytokines in Allergic Inflammation," *Int. Arch. Aller. Immunol.*, (1997), 113:196-199.
Kern, et al., "Direct Hybridization of Large-Insert Genomic Clones on High-Density Gridded cDNA Filter Arrays," *Biotechniques*, (1997), 23:120-124.
Khazak et al., "Selective Raf Inhibition in Cancer Therapy," (2012), http://www.ncbu.nlm.nih.gov/pms/articles/PMC2720036.
Kim, et al., "A Merger of Rational Drug Design and Combinatorial Chemistry: Development and Application of Peptide Secondary Structure Mimetics," *Combinatorial Chemistry & High Throughput Screening*, (2000), 3:167-183.
Kim, et al., Database CAS on STN Preparation of 2-anilino-4-indolyl pyrimidines as tyrosine kinase inhibitors, abstract, 2002) (Columbus, OH, USA) No. 138:55974.
Kinashi, et al., "Steel Factor and c-kit Cell-Matrix Adhesion," *Blood*, (1994), 83:1033-1038.
Kirkpatrick, et al., "Structure-Based Drug Design: Combinatorial Chemistry and Molecular Modeling," *Combinatorial Chemistry & High Throughput Screening*, (1999), 2:211-221.
Kitamura, et al., "Synthesis of Quinolines and 2H-Dihydropyrroles by Nucleophilic Substitution at the Nitrogen Atom of Oxime Derivatives," *Synthesis*, (2003), 15:2415-2426.
Kline, et al., "Studies by 1H Nuclear Magnetic Resonance and Distance Geometry of the Solution Conformation of the x-Amylase Inhibitor Tendamistat," *J. Mol. Biol.*, (1986), 189:377-382.
Knighton, et al., "Structural Basis of the Intrasteric Regulation of Myosin Light Chain Kinases," *Science*, (1992), 258:130-135.
Kodama, et al., "Congenital Osteoclast Deficiency in Osteopetrotic (op/op) Mice Is Cured by Injections of Macrophage colony-stimulating Factor," *J. Exp,. Med.*,(1991), 173:269-272.
Kolaskar, et al., "A Semi-Empirical Method for Prediction of Antigenic Determinants on Protein Antigens," *FEBS Lett.*, (1990), 276:172-174.

(56) References Cited

OTHER PUBLICATIONS

Komoyira, et al., "Design, synthesis and biological activity of amidinobicyclic compounds (derivatives of DX-9065a) as a factor Xa inhibitors: SAR study of S1 and aryl binding sites," *Bioorg. Med. Chem.*, (2004), 12: 2099-2114.
Kondoh, et al., "An in vivo model for receptor tyrosine kinase autocrine/paracrine activation: auto-stimulated Kit receptor acts as a tumor promoting factor in papillomavirus-induced tumorigenesis," *Oncogene*, (1995), 10:341-347.
Kondoh, et al., "Establishment and Further Characterization of a Line of Transgenic Mice Showing Testicular Tumorigenesis at 100% Incidence," *J. Urol.*, (1994), 152:2151-2154.
Kondoh, et al., "Very High Incidence of Germ Cell tumorigenesis (Seminomagenesis) in Human Papillomavirus Type 16 Transgenic Mice," *J. Virol.*, (1991), 65:3335-3339.
Konishi, et al., "Overexpression of leucocyte common antigen (LAR) P-subunit in thyroid carcinomas," *Brit J Cancer*, (2003), 88:1223-1228.
Konno et al., "Influence of Different Polymers on the Crystallization Tendency of Molecularly Dispersed Amorphous Felodipine," *Journal of Pharmaceutical Sciences*, (2006), 95(12):2692-2705.
Kubo et al., "Resequencing Analysis of the Human Tyrosine Kinase Gene Family in Pancreatic Cancer," *Pancreas*, (2009), 38(7):e200-e206.
Kubo et al., "Resequencing and copy number analysis of the human tyrosine kinase gene family in poorly differentiated gastric cancer," *Carcinogenesis*, (2009), 30(11 ): 1857-1864.
Kundu, et al., "Combinatorial Chemistry: Polymer Supported Synthesis of Peptide and Non-Peptide Libraries," *Progress in Drug Research*, (1999), 53:89-156.
Kunisada, et al., "Murine Cutaneous Mastocytosis and Epidermal Melanocytosis Induced by Keratinocyte Expression of Transgenic Stem Cell Factor," *J. Exp. Med.*, (1998), 187:1565-1573.
Kunkel, T., "Rapid and Efficient Site-Specific Mutagenesis Without Phenotypic Selection" *Proc. Natl. Acad. Sci. USA*, (1985), 82: 488-492.
Kunnimalaiyaan, et al., "The Raf-1 pathway: a molecular target for treatment of select neuroendocrine tumors?" *Anticancer Drugs*, (2006), 17(2):139-42.
Kuntz, et al., "A Geometric Approach to Macromolecule-Ligand Interactions," *J. Mol. Biol.*, (1982), 161:269-288.
Kuntz, et al., "Structure-Based Molecular Design," *Acc. Chem. Res.*, (1994), 27:117-123.
Lahm, et al., "Interleukin 4 Down-Regulates Expression of c-kit and Autocrine Stem Cell Factor in Human Colorectal Carcinoma Cells," *Cell Growth & Differ.*, (1995), 6:1111-1118.
Lala, et al., "Role of nitric oxide in tumor progression: Lessons from experimental tumors," *Cancer and Metastasis Reviews*, (1998), 17:91-106.
Lam, et al., "A new type of synthetic peptide library for identifying ligand-binding activity," *Nature*, (1991), 354: 82-84.
Lambros et al., "Genomic profile of a secretory breast cancer with an ETV6-NTRK3 duplication," *J. Clin. Pathol.*, (2009), 62(7):604-12.
Langham et al., "Metalation and Halogen-Metal Interconversion Reactions of Some Halogenated Phenyl Ethers," *J. of the Am. Chem. Society*, (1941), 63:545-549.
Lawicki, et al., "The pretreratment plasma level and disgnostic utility of M-CSF in benign breast tumor and breast cancer patients," *Clinica Chimica Acta.*, (2006), 371:112-116.
Layzer, "Degenerative Diseases of the Nervous System," *Cecil Textbook of Medicine, 20th Edition*, (1996), 2:2050-2057.
Le Meur, M., "Macrophage accumulation at a site of renal inflammation is dependent on the M-CSF/c-fms pathway," *J Leukocyte Biology*, (2002), 72:530-537.
Lee et al., "FMS-like tyrosine kinase 3 inhibitors: a patent review," *Expert Opinion Ther. Patents*, (2011), 21(4):483-503.
Lee, et al., "HLA-DR-Triggered Inhibition of Hemopoiesis Involves Fas/Fas Ligand Interactions and is Prevented by c-kit Ligand," *J. Immunol.*, (1997), 159:3211-3219.
Lee, et al., "Mast Cells: A Cellular Link Between Autoantibodies and Inflammatory Arthritis," *Science*, (2002), 297:1689-1692.
Leuner, et al., "Improving drug solubility for oral delivery using solid dispersions," *European Journal of Pharma. and Biopharma.*, (2000), 50(1):47-60.
Levin, et al., "Neoplasms of the Central Nervous System," *Cancer Principles & Practice of Oncology*, (1997), 2:2022-2082.
Levis et al., "A FLT3 tyrosine kinase inhibitor is selectively cytotoxic to acute myeloid leukemia blasts harboring FL T3 internal tandem duplication mutations," *Blood*, (2001), 98:885-887.
Li, et al., "Abrogation of c-kit/Steel Factor-Dependent Tumorigenesis by Kinase Defective Mutants of the c-kit Receptor: c-kit Kinase Defective Mutants as Candidate Tools for Cancer Gene Therapy," *Canc. Res.*, (1996), 56:4343-4346.
Libby, P., "Inflammation in atherosclerosis," *Nature*, (2002), 420:868-874.
Lipinski, et al., "Experimental and Computational Approaches to Estimate Solubility and Permeability in Drug Discovery and Development Settings," *Advanced Drug Delivery Reviews*, (1997), 23:3-25.
Liu, et al., "CD68 Expression is Markedly Different in Crohn's Disease and the Colitis Associated with Chronic Granulomatous Disease," *Inflamm. Bowel Dis.*, (2009), 15(8): 1213-1217.
London, et al., "Expression of Stem Cell Factor Receptor (c-kit) by the Malignant Mast Cells from Spontaneous Canine Mast Cell Tumors," *J. Compar. Pathol.*, (1996), 115:399-414.
Longley, et al., "Altered Metabolism of Mast-cell Growth Factor (c-kit Ligand) in Cutaneous Mastocytosis," *New Engl. J. Med.*, (1993), 328:1302-1307.
Longley, et al., "Chymase Cleavage of Stem Cell Factor Yields a Bioactive Soluble Product," *Proc. Natl. Acad. Sci.*, (1997), 94:9017-9021.
Longley, et al., "Somatic c-KIT Activating Mutation in Urticaria Pigmentosa and Aggressive Mastocytosis: Establishment of Clonality in a Human Mast Cell Neoplasm," *Nat. Gen.*, (1996), 12:312-314.
Louvet et al., "Tyrosine kinase inhibitors reverse type 1 diabetes in nonobese diabetic mice," *Proc. Nat. Acad. Sci.*, (2008), 105(48): 18895-18900.
Loveland, et al., "Stem Cell Factor and c-kit in the Mammalian Testis: Lessons Originating from Mother Nature 19s Gene Knockouts," *J. Endocrinol.*, (1997), 153:337-344.
Lu, et al., "Oriented Immobilization of Fab 19 Fragments on Silica Surfaces," *Anal. Chem.*, (1995), 67:83-87.
Lukacs, et al., "Stem Cell Factor (c-kit Ligand) Influences Eosinophil Recruitment and Histamine Levels in Allergic Airway Inflammation," *J. Immunol.*, (1996), 156:3945-3951.
Luo, et al., "Close Linkage with the RET Proto-Oncogene and Boundaries of Deletion Mutations in Autosomal Dominant Hirschsprung Disease," *Hum Mol Genet.*, (1993), 2(11):1803-1808.
Lyman, et al., "c-kit Ligand and Flt3 Ligand: Stem/Progenitor Cell Factors With Overlapping Yet Distinct Activities," *Blood*, (1998), 91:1101-1134.
Ma, et al., "Indolinone Derivatives Inhibit Constitutively Activated KIT Mutants and Kill Neoplastic Mast Cells," *J Invest Dermatol.*, (2000), 114:392-394.
Ma, et al., "The c-KIT Mutation Causing Human Mastocytosis is Resistant to ST1571 and Other KIT Kinase Inhibitors; Kinases with Enzymatic Site Mutations Show Different Inhibitor Sensitivity Profiles Than Wild-type Kinases and Those With Regulatory-Type Mutations," *Blood*, (2002), 99:1741-1744.
Machens, et al., "Modification of multiple endocrine neoplasia 2A phenotype by cell membrane proximity of RET mutations in exon 10," *Endocrine-Related Cancer*, (2009), 16:171-177.
Machida, et al., "Mitogen-activated Protein Kinase Kinase Kinase Kinase 4 as a Putative Effector of Rap2 to Activate the c-Jun N-terminal Kinase," *J. Biol. Chem.*, (2004), 279:15711-15714.
Mack, et al., "Functional identification of kinases essential for T-cell activation through a genetic suppression screen," *Immunol. Lett.*, (2005), 96:129-145.
Madden, et al., "Synthetic Combinatorial Libraries: Views on Techniques and Their Application," *Perspectives in Drug Discovery and Design*, (1994), 2:269-285.

(56) References Cited

OTHER PUBLICATIONS

Madhusdan et al., "Tyrosine kinase inhibitors in cancer therapy," *Clinical Biochemistry*, (2004), 37:618-635.
Marchetti et al., "Frequent Mutations in the Neurotrophic Tyrosine Receptor Kinase Gene Family in Large Cell Neuroendocrine Carcinoma of the Lung," *Hum. Mutat.*, (2008), 29(5):609-16.
Marshall, et al., "Blockade of colony stimulating Factor-1 (CSF-1) Leads to inhibition of DSS-induced colitis," *Inflamm. Bowel Dis.*, (2007), 13(2): 219-224.
Martin, Y., "Computer-Assisted Rational Drug Design," *Methods Enz.*, (1991), 203:587-613.
Matayoshi, et al., "Actions of brain-derived neurotrophic factor on spinal nociceptive transmission during inflammation in the rat," *J Physiol.*, (2005), 569:685-695.
Matsumoto, et al., "Physical properties of solid molecular dispersions of indomethacin with poly(vinylpyrrolindone) and poly(vinylpyrrolidone-co-vinyl-acetate) in relation to indomethacin crystallization," *Pharmaceutical Research*, (1999), 16(11):1722-1728.
Mazeas, et. al., "Synthesis of new melatoninergic ligands including azaindole moiety," *Heterocycles*, (1999), 50:1065-1080.
McCall, et al., "Characterization of Anti-Mouse FcγRll Single-Chain Fv Fragments Derived from Human Phage Display Libraries," *Immunotechnology*, (1998), 4:71-87.
McDermott et al., "Identification of genotype-correlated sensitivity to selective kinase inhibitors by using high throughput tumor cell line profiling," *PNAS*,(2007), 104(50): 19936-19941.
McPherson, A., "Current Approaches to Macromolecule Crystallization," *Eur. J. Biochem.*, (1990), 189:1-23.
Mettey et al., "Aloisines, a New family of CDK.GSK-3 Inhibitors. SAR Study, Crystal Structure in Complex with CDK2, Enzyme Selectivity, and Cellular Effects," *J. Med. Chem.*, (2003), 46:222-236.
Mekori, et al., "The Role of c-Kit and Its Ligand, Stem Cell Factor, in Mast Cell Apoptosis," *Int. Arch. Allergy Immunol.*, (1995), 107:136-138.
Mekori, et al., "Transforming Growth Factor-β Prevents Stem Cell Factor-Mediated Rescue of Mast Cells from Apoptosis After IL-3 Deprivation," *J. Immunol.*, (1994), 153:2194-2203.
Meltzer, E. O., "The pharmacological basis for the treatment of perennial allergic rhinitis and non-allergic rhinitis with topical corticosteroids," *Aller.*, (1997), 52:33-40.
Meng, et al., "Automated Docking with Grid-Based Energy Evaluation," *J. Compt. Chem.*, (1992), 13:505-524.
Menke et al., "Sunlight triggers cutaneous lupus through a CSF-1-dependent mechanism in MRL-Fas$^{lpr}$ mice," *Journal of Immunology*, (2008), 181: 7367-7379.
Merour, et al., "Synthesis and Reactivity of 7-Azaidoles (1H-Pyrrolo[2,3-b]pyridine)," *Curr. Org. Chem.*, (2001), 5:471-506.
Merritt, A., "Solution Phase Combinatorial Chemistry," *Comb Chem High Throughput Screen*, (1998), 1:57-72.
Metcalf, D., "Lineage Commitment in the Progeny of Murine Hematopoietic Preprogenitor Cells: Influence of Thrombopoietin and Interleukin 5," *Proc. Natl. Acad. Sci.*, (1998), 95:6408-6412.
Metcalfe, D. "Classification and Diagnosis of Mastocytosis: Current Status," *J. Invest. Derm.*, (1991), 93:2S-4S.
Metcalfe, et al., "Mast Cells," *Physiol. Rev.*, (1997), 77:1033-1079.
Muela Pomeda, et al., "Efecto De Codisolventes Y Dispersiones Solida De Polivinilpirrolidona K-30 En La Solubilidad Tel Tiabendazol," *Departamento de Farmacia y Tecnologia Farmaceutica. Facultad de Farmacia. Universidad de Alcala*, (2002), pp. 85-87, (No English Translation Available).
Miller et al., "FLOG: A System to Select Quasi-Flexible Ligands Complementary to a Receptor of Known Three-Dimensional Structure," *J. Comp. Aided Molec. Design*, (1994), 8:153-174.
Minakata, et al., "Functionalization of 1H-Pyrrolo[2,3-b]pyridine," *Bulletin of the Chemical Society of Japan*, (1992), 65(11):2992-2997.
Minakata, et al., "Regioselective Funtionalization of 1H-Pyrrolo[2,3-b]pyridine Via its N-Oxide," *Synthesis*, (1992), 661-663.

Miranker, at al., "Functionality Maps of Binding Sites: A Multiple Copy Simultaneous Search Method," *Proteins: Structure, Function, and Genetics*, (1991), 11:29-34.
Mitra, et al., "Fluorescence Resonance Energy Transfer Between Blue-Emitting and Red-Shifted Excitation Derivatives of the Green Fluorescent Protein," *Gene*, (1996), 173:13-17.
Mokhtari, et al., "Potential utility of small tyrosine kinase inhibitors in the treatment of diabetes," *Clinical Science*, (2010), 118(4):241-247.
Mol, et al., "Structural Basis for the Autoinhibition and STI-571 Inhibition of c-Kit Tyrosine Kinase," *J. Biol. Chem.*, (2004), 279:31655-31663.
Mol, et al., "Structure of a c-Kit Product Complex Reveals the Basis for Kinase Transactivation," *J. Biol. Chem.*, (2003), 278:31461-31464.
Morgan, et al., "Isolation and Characterization of a Cloned Growth Factor Dependent Macrophage Cell Line, BAC1.2F5," *J. of Cell. Physiology*, (1987), 130:420-427.
Motoyoshi, K., "Biological activities and clinical application of M-CSF," *Int J Hematol.* (1998), 67:109-122.
Murphy, et al., "Expression of macrophage colony-stimulating factor receptor is increased in the AβPP$^{V717F}$ transgenic mouse model of Alzheimer's disease," *Am. J. of Pathology*, (2000), 157⊗3) 895-904.
Murty, et al.""A Genetic Perspective of Male Germ Cell Tumor"," *Sem. Oncol.*, (1998), 25:133-144.
Naclerio, et al.""Rhinitis and Inhalant Allergen"," *Jama*, (1997), 278:1842-1848.
Nagafuji, et al.""A General Synthesis of Pyrroles and Fused Pyrrole Systems from Ketones and Amino Acid"," *J. Org. Chem.*, (1996), 61:4999-5003.
Nagata, et al.""Elevated Expression of the Proto-Oncogene c-kit in Patients with Mastocytosi"," *Leukemia*, (1998), 12:175-181.
Nahm et al.""N-Methoxy-N-Methylamides as Effective Acylating Agent"," *Tetrahedron Lett.*, (1981), 22(39):3815-3818.
Nakagawara, et al.""Expression and Function of TRK-B an BDNF in Human Neuroblastoma"," *Mol. Cell Biol.*, (1994), 14:759-767.
Nakai et al.""New Potent Antagonists of Leukotrienes C4 and D4. 01. Synthesis and Structure-Activity Relationship"," *J. Med. Chem.*, (1988), 31:(1):84-91.
Nassentein, et al.""The Neurotrophins Nerve Growth Factor, Brain-derived Neurotrophic Factor, Neurotrophin-3, and Neurotrophin-4 Are Survival and Activation Factors for Eosinophils in Patients with Allergic Bronchial Asthm"," *J. Exp. Med.*, (2003), 198:455-467.
Natali, et al.""Breast cancer is associated with loss of the c-kit oncogene produc"," *Int. J. Cancer*, (1992) 52:713-717.
Navaza, J.""AMoRe: an Automated Package for Molecular Replacemen"," *Acta Cryst.*, (1994), A50:157-163.
Neidle, et al.""Molecular Modeling to Study DNA Intercalation by Anti-Tumor Drug"," *Methods Enz.*, (1991), 203:433-458.
Ng, et al.""Engineering Protein-Lipid Interactions: Targeting of Histidine-Tagged Proteins to Metal-Chelating Lipid Monolayer"," *Langmuir*, (1995), 11:4048-4055.
Nicholls, et al.""Protein Folding and Association: Insights From the Interfacial and Thermodynamic Properties of Hydrocarbon"," *Proteins*, (1991), 11:281-296.
Nichols, et al.""Development of a Scintillation Proximity Assay for Peroxisome Proliferator-Activated Receptor γ Ligand Binding Domai"," *Anal. Biochem.*, (1998), 257:112-119.
Niihori, et al.""Germline KRAS and BRAF mutations in cardio-facio-cutaneous syndrom"," *Nature Genet.*, (2006), 38(3):294-296.
Ochs, et al.""A phase I/II trial of recombinant methionyl human brain derived neurotrophic factor administered by intrathecal infusion to patients with amyotrophic lateral sclerosi"," *Amyotroph Lateral Scler Other Motor Neuron Disord.*, (2000), 1:201-206.
Odegaard et al. "Macrophage-specific PPARg controls alternative activation and improves insulin resistance," *Nature*, (2007), 447: 1116-1121.
Ohno, et al. "A c-fms tyrosine kinase inhibitor, KI202227, suppresses osteoclast differentiation and osteolytic bone destruction in a bone metastasis model," *Mol. Cancer Ther.*, (2006), 5(11):2634-2643. 2634-43.

(56) References Cited

OTHER PUBLICATIONS

Ohno, et al., "The orally-active and selective c_FMS tyrosine kinase inhibitor Ki20227 inhibits disease progression in a collagen-induced arthritis mouse model," *Eur. J Immunol.*, (2008), 38: 1-9.

Okayama, et al., "Activation of Eosinophils with Cytokines Produced by Lung Mast Cells," *Int. Arch. Aller. Immunol.*, (1997), 114(suppl. 1):75-77.

Okayama, et al., "Human Lung Mast Cells are Enriched in the Capacity to Produce Granulocyte-Macrophage Colony-Stimulating Factor in Response to IgE-Dependent Stimulation," *Eur. J. Immunol.*, (1998), 28:708-715.

Olah, et al., "Synthetic Methods and Reactions: Part 209. Improved Preparation of Aldehydes and Ketones from N,N-Dimethylamides and Grignard Reagents," *Synthesis*, (1984), 228-230.

Ottoni, et al., "Efficient and Simple Methods for the Introduction of the Sulfonyl, Acyl and Alkyl Protecting Groups on the Nitrogen of Indole and its Derivatives," *Tetrahedron*, (1998), 54:13915-13928.

Otwinowski, Z., "Maximum Likelihood Refinement of Heavy Atom Parameters," *Dept. of Molecular Biophysics and Biochemistry*, (1991), 80-86.

Owicki, et al., "Application of Fluorescence Polarization Assays in High-Throughput Screening," Genetic Engineering News, (1997), 17:27.

Panitumumab, (2011),"In Combination with Cisplatin/Gemcitabine", http://clinicaltrials.gov/ct2/show/NCT0132054.

Parker, et al., "Development of High Throughput Screening Assays Using Fluorescence Polarization: Nuclear Receptor-Ligand-Binding and Kinase/Phosphatase Assays," *J Biomol Screen*, (2000), 5:77-88.

Patani et al, "Bioisosterism: a rational approach in drug design," *Chem Rev*, (1996), 96:3147-3176.

Pearce et al., "Failure modes in anticancer drug discovery and development," *Cancer Drug Design and Discovery* Edited by Stephen Neidle, (2008), Chapter 18: 424-435.

Perrin, D., "Nucleic Acids for Recognition and Catalysis: Landmarks, Limitations, and Looking to the Future," *Combinatorial Chemistry & High Throughput Screening*, (2000), 3:243-269.

Petty, et al., "The effect of systemically administered recombinant human nerve growth factor in healthy human subjects," *Ann Neurol.*, (1994), 36:244-246.

Pflugrath, et al., "Crystal Structure Determination, Refinement and the Molecular Model of the x-Amylase Inhibitor Hoe-467A," *J. Mol. Biol.*, (1986), 189:383-386.

Pierce, et al., "Local anesthetics. I. beta-Monoaklylaminoethyl Esters of Alkoxybenzoic Acids," *J. Am. Chem. Soc.*, (1942), 64:1691-1694.

Pignon, J.M., "C-kit mutations and mast cell disorders a model of activating mutations of growth factor receptors," *Hermatol Cell Ther.*, (1997), 39:114-116.

Plunkett, et al., "A Silicon-Based Linker for Traceless Solid-Phase Synthesis," *J. Org. Chem.*, (1995), 60:6006-6007.

Poul, et al., "Selection of Tumor-Specific Internalizing Human Antibodies from Phage Libraries," *J. Mol. Biol.*, (2000), 301:1149-1161.

Prada et al., "Neurofibroma-associated Macrophages Play Roles in Tumor Growth and Response to Pharmacological Inhibition," *Acta Neuropathol*, (2013), 125: 159-168.

Pratilas et al., "Marker gene showing changes in levels of expression in response to antineoplastic drug therapy and their use of chemotherapy", *Hcalplus*, (2008) 670875.

Prien, "Target-family-oriented focused libraries for kinases—Conceptual design aspects and commercial availability," *ChemBioChem*, (2005), 6:500-505.

Qiao, et. al., "Role of Macrophage Colony-Stimulating Factor in Atherosclerosis," *Am. J. Path.*, (1997), 150:1687-1699.

Rajavashisth, et. al., "Heterozygous Osteopetrotic (op) Mutation Reduces Atherosclerosis in LDL Receptor-deficient Mice," *J. Clin. Invest.*, (1998), 101:2702-2710.

Rajpert-De Meyts, et al., "Expression of the c-kit Protein Product in Carcinoma-in-situ and Invasive Testicular Germ Cell Tumours," *Int. J. Androl.*, (1994), 17:85-92.

Rapp, et al., "Raf kinases in lung tumor development," *Advan. Enzyme Regul.*, (2003) 43:183-195.

Remington: *The Science and Practice of Pharmacy*, vol. II, (1995), pp. 1454-1460.

Ricotti, et al., "c-kit Is Expressed in Soft Tissue Sarcoma of Neuroectodermic Origin and Its Ligand Prevents Apoptosis of Neoplastic Cells," *Blood*, (1998), 91:2397-2405.

Ridge, et al., "FMS mutations in myelodysplastic, leukemic, and normal subjects," *Proc. Nat. Acad. Sci.*, (1990), 87:1377-1380.

Ritz, et al., "Elevated blood levels of inflammatory monocytes ($CD14^+CD16^+$) in patients with complex regional pain syndrome," *Clin. Exper. Immunology*, (2011), 1-10.

Roberts et al., "Targeting the Raf-MEK-ERK mitogen-activated protein kinase cascade for the treatment of cancer," *Oncogene* (2007) 26:3291-3310.

Robinson, et al., "Stimulation of Bone Marrow Colony Growth In Vitro by Human Urine," *Blood*, (1969), 33:396-399.

Robison, et al., "7-Azaindole. I. Synthesis and Conversion to 7-Azatryptophan and Other Derivatives," *J. Am. Chem. Soc.*, (1955), 77:457-460.

Rodan, et al., "Therapeutic Approaches to Bone Diseases," *Science*, (2000), 289:1508-1514.

Rodriguez-Viciana, et al., "Germline Mutations in Genes Within the MAPK Pathway Cause Cardio-facio-cutaneous Syndrome," *Science*, (2006), 311:1287-1290.

Rosenfeld, M.A., "Human artificial chromosomes get real," *Nat. Genet.*, (1997), 15:333-335.

Rosnet et al., "Isolation and Chromosomal Localization of a Novel FMS-like Tyrosine Kinase Gene," *Genomics*, (1991), 9: 380-385.

Ryan, et al., "Role for the Stem Cell Factor/KIT Complex in Schwann Cell Neoplasia and Mast Cell Proliferation Associated with Neurofibromatosis," *J. Neuro. Res.*, (1994), 37:415-432.

Saify, et al., "Synthesis of some 7-azaindole derivatives: Their cytotoxicity and antibacterial activity," *Pakistan Journal of Scientific and Industrial Research*, (1994), 37(10):439-441.

Saiki, R.K., "Amplification of Genomic DNA," *PCR Protocols, A Guide to Methods and Applications*, (1990), pp. 13-20.

Sandlow, et al., "Expression of c-Kit and its Ligand, Stem Cell Factor, in Normal and Subfertile Human Testicular Tissue," *J. Androl.*, (1996), 17:403-408.

Santoro, et al., "The ret Proto-Oncogene is Consistently Expressed in Human Pheochromocytomas and Thyroid Medullary Carcinomas," *Oncogene*, (1990), 5(10):1595-1598.

Sathornsumetee, et al., "AAL881, a Novel Small Molecule Inhibitor of RAF and Vascular Endothelial Growth Factor Receptor Activities, Blocks the Growth of Malignant Glioma," *Cancer Res.*, (2006), 66:8722-8730.

Sawada, et al., "4-(Benzoylindolizinyl)butyric acids; Novel nonsteroidal inhibitors of steroid 5;1-reductase. III," *Chemical and Pharmaceutical Bulletin*, (2001), 49(7):799-813.

Sawada, et al., "Role of Cytokines in Leukemic type Growth of Myelodysplastic CD34+ Cells," *Blood*, (1996), 88:319-327.

Sawai, et al., "Aberrant growth of granulocyte-macrophage progenitors in juvenile chronic myelogenous leukemia in serum-free culture," *Exp. Hem.*, (1996), 2:116-122.

Scheffner, et al., "The E6 Oncoprotein Encoded by Human Papillomavirus Types 16 and 18 Promotes the Degredation of p53," *Cell*, (1990), 63:1129-1136.

Schiemann, et al., "p-Fluorobenzoic Acid," *Org. Syn. Coll.*, (1943), 2:299-301.

Sclabas et al., "Overexpression of Tropomysin-Related Kinase Bin Metastatic Human Pancreatic Cancer Cells," *Clin. Cancer. Res*,(2005), VII: 440-449.

Schneider, et al., "Functional Purification of a Bacterial ATP-Binding Cassette Transporter Protein (MaIK) from the Cytoplasmic Fraction of an Overproducing Strain," *Protein Expr. Purif.*, (1995), 6:10-14.

(56) References Cited

OTHER PUBLICATIONS

Schneller, et. al., "Synthesis of 4-Amino-1 H-pyrrolo[2,3-b]pyridine {1,7-Dideazaadenine) and 1H-Pyrrolo[2,3-b]pyridine-4-ol (1,7-Dideazahypoxanthine)," *J. Org. Chem.*, (1980), 45:4045-4048.

Schuhmann, et al., "Immobilization of Enzymes on Langmuir-Blodgett Films via a Membrane-Bound Receptor. Possible Applications for Amperometric Biosensors," *Adv. Mater.*, (1991), 3:388-391.

Schummer, et al., "Inexpensive Handheld Device for the Construction of High-Density Nucleic Acid Arrays," *Biotechniques*, (1997), 23:1087-1092.

Schweizer, et al., "Combinatorial Synthesis of Carbohydrates," *Curr Opin Chem Biol*, (1999), 3(3):291-298.

Serajuddin, A. T. M., "Solid Dispersion of Poorly Water-Soluble Drugs: Early Promises, Subsequent Problems, and Recent Breakthroughs," *J. Pharm. Sci.*, (1999), 8(10), 1058-1066.

Secor, et al., "Mast cells are essential for early onset and severe disease in a murine model of multiple sclerosis," *J. Exp. Med.*, (2000), 5:813-821.

Selvin, P., "Fluorescence Resonance Energy Transfer," *Meth. Enzymol.*, (1995), 246:300-345.

Shah et al., "Development of Novel Microprecipitated Bulk Power(MBP) Technology for Manufacturing Stable Amorphous Formulations of Poorly Soluble Drugs", *International Journal of Pharmaceutics*, (2012), 438: pp. 53-60.

Shah et al., "Improved Human Bioavailability of Vemurafenib, A Practically Insoluble Drug, Using an Amorphous Polymer-Stabilized Solid Dispersion Prepared by a Solvent-Controlled Coprecipitation Process," *Journal of Pharmceutical Sciences*, (2012), pp. 1-15.

Shan, et al., "Prodrug strategies based on intramolecular cyclization reactions," *Journal of Pharmaceutical Sciences*, (1997), 86(7):765-767.

Sheets, et al., "Efficient Construction of a Large Nonimmune Phage Antibody Library: The Production of High-Affinity Human Single-Chain Antibodies to Protein Antigens," *Proc Natl Acad Sci USA.*, (1998), 95:6157-6162.

Shibata, et al., "Alveolar macrophage deficiency in osteopetrotic mice deficient in macrophage colony-stimulating factor is spontaneously corrected with age and associated with matrix metalloproteinase expression and emphysema," *Blood*, (2001), 98:2845-2852.

Siegel, et al., "Mass Spectral Analysis of a Protein Complex Using Single-Chain Antibodies Selected on a Peptide Target: Applications to Functional Genomics," *Journal of Molecular Biology*, (2000), 302:285-293.

Sigal, et al., "A Self-Assembled Monolayer for the Binding and Study of histidine-Tagged Proteins by Surface Plasmon Resonance," *Anal. Chem.*, (1996), 68:490-497.

Silverman, Prodrugs and Drug Delivery Systems, *The Organic Chemistry of Drug Design and Drug Action, Academic Press, Inc.* (1992), pp. 352-399.

Simone, "Oncology: Introduction," *Cecil Textbook of Medicine, 20th Edition*, (1996), 1:1004-1010.

Small et al., "STK-I, the human homolog ofFlk-2/Flt-3, is selectively expressed in CD34+ human bone marrow cells and is involved in the proliferation of early progenitor/stem cells," *Proc. Nat. Acad. Sci.*, (1994), 91: 459-463.

Smalley, et al., "c-Kit signaling as the driving oncogenic event in sub-groups of melanomas," *Histol Histopathol*, (2009), 24:643-650.

Smith, et al., "The Role of kinase inhibitors in the treatment of patients with acute myeloid leukemia," (2013), *Am Soc Clin Oncol Educ Book*, (2013), pp. 313-318.

Solinas-Toldo, et al., "Matrix-Based Comparative Genomic Hybridization Biochips to Screen for Genomic Imbalances," *Genes, Chromosomes & Cancer*, (1997), 20:399-407.

Song, et al., "Isomerism of Bis(7-azaindolyl)methane," *Organic Letters*, (2002), 4(23):4049-4052, Table of content pp. 1-16 and Supporting information pp. 1-15.

Soreafenib, (2012), http://www.cancer.gov/cancertopics/druginfo/sorafenibtosylate.

Sperling, et al., "Expression of the Stem Cell Factor Receptor C-Kit (CD117) in Acute Leukemias," *Haemat.*, (1997), 82:617-621.

Specchia et al., "Constitutive expression ofiL-Iβ, M-CSF and c-fms during the myeloid blastic phase of chronic myelogenous leukaemia," *Br J Haematol.*, (1992), 80(3):310-316.

Stanulla, et al., "Coexpression of Stem Cell Factor and Its Receptor c-Kit in Human Malignant Glioma Cell Lines," *Act Neuropath.*, (1995), 89:158-165.

Steinman, L., "Multiple sclerosis: A coordinated immunological attack against myelin in the central nervous system," *Cell*, (1996), 85:299-302.

Strohmeyer, et al., "Expression of the C-kit Proto-Oncogene and its Ligand Stem Cell Factor (SCF) in Normal and Malignant Human Testicular Tissue," *J. Urol.*, (2005), 153:511-515.

Strohmeyer, et al., "Expression of the hst-1 and c-kit Protooncogenes in Human Testicular Germ Cell Tumors," *Canc. Res.*, (1991), 51:1811-1816.

Su et al., "Synthesis of bromo-substituted Idoxyl Esters for Cytochemical Demonstration of Enzyme Activity," *J. Am. Chem. Soc.*, (1960), 82:1187-1189.

Sun, C., "Recent Advances in Liquid-Phase Combinatorial Chemistry," *Comb. Chem. & High Throughput Screening*, (1999), 2:299-318.

Sun, et al., "Design, Synthesis, and Evaluations of Substituted 3-[(3- or 4-Carboxyethylpyrrol-2-yl) Methylidenyl]indolin-2-Ones as Inhibitors of VEGF, PGF, and PDGF Receptor Tyrosine Kinases," *J. Med. Chem.*, (1999), 42:5120-5130.

Tada, et al., "Analysis of Cytokine Receptor Messenger RNA Expression in Human Glioblastoma Cells and Normal Astrocytes by Reverse-Transcription Polymerase Chain Reaction," *J. Neuro.*, (1994), 80:1063-1073.

Takahashi, et al., "Activation of a Novel Human Transforming Gene, ret, by DNA Rearrangement," *Cell*, (1985), 42(2):581-588.

Takahashi, et al., "Cloning and Expression of the ret Proto-Oncogene Encoding a Tyrosine Kinase with Two Potential Transmembrane Domains," *Oncogene*, (1988), 3(5):571-578.

Takahashi, et al., "ret Transforming Gene Encodes a Fusion Protein Homologous to Tyrosine Kinases," *Mol Cell Biol.*, (1987), 7:1378-1385.

Tang, et al., "An RNA interference-based screen identifies MAP4K4/NIK as a negative regulator of PPARγ, adipogenesis, and insulin-responsive hexose transport," *Proc. Natl. Acad. Sci.*, (2006), 103:2087-2092.

Tanno et al., "Evaluation of Hypromellose Acetate Succinate (HPMCAS) as a Carrier in Solid Dispersions," *Drug Development and Industrial Pharmacy*, (2004), 30(1):9-17.

Teitelbaum, S.L., "Bone Resorption by Osteoclasts," *Science*, (2000), 289:1504-1508.

Thibault, et. al., "Concise and Efficient Synthesis of 4-fluoro-1H-pyrrolo[2,3-b] pyridine," *Org. Lett.*, (2003), 5:5023-5025.

Thomas, et al., "The Eosinophil and its Role in Asthma," *Gen. Pharmac.*, (1996), 27:593-597.

Thomas, et. al., "Light-Emitting Carbazole Derivatives: Potential Electroluminescent Materials," *J. Am. Chem. Soc.*, (2001), 123:9404-9411.

Toste, et al., "A Versatile Procedure for the Preparation of Aryl Thiocyanates Using N-Thiocyanatosuccinimide (NTS)," *Synth. Comm.*, (1995), 25(8):1277-1286.

Toy et al., "Enhanced ovarian cancer tumorigenesis and metastasis by the mecrophage colony-stimulating factor," *Neoplasia*, (2009), 11:(2) 136-144.

Toyota, et al., "Expression of c-kit and kit Ligand in Human Colon Carcinoma Cells," *Turn Biol.*, (1993), 14:295-302.

Trupp, et al., "Functional Receptor for GDNF Encoded by the c-ret Proto-Oncogene," *Nature.*, (1996), 381:785-789.

Tsuda, et al., "Microglia and Intractable Chronic Pain," *GLIA*, (2012), pp. 1-7.

Tsujimura, et al., "Ligand-Independent Activation of c-kit Receptor Tyrosine Kinase in a Murine Mastocytoma Cell Line P-815 Generated by a Point Mutation," *Blood*, (1994), 9:2619-2626.

(56) References Cited

OTHER PUBLICATIONS

Tsujimura, et al., "Substitution of an Aspartic Acid Results in Constitutive Activation of c-kit Receptor Tyrosine Kinase in a Rat Tumor Mast Cell Line RBL-2H3," *Int. Arch. Aller. Immunol.*, (1995), 106:377-385.
Tsujimura, T., "Role of c-kit Receptor Tyrosine Kinase in the Development, Survival and Neoplastic Transformation of Mast Cells," *Pathol Int.*, (1996), 46:933-938.
Turner, et al., "Nonhematopoeietic Tumor Cell Lines Express Stem Cell Factor and Display c-kit Receptors," *Blood*, (1992), 80:374-381.
Udenfriend, et al., "Scintillation Proximity Assay: A Sensitive and Continuous Isotopic Method for Monitoring Ligand/Receptor and Antigen/Antibody Interactions," *Anal. Biochem*, (1987), 161:494-500.
Uemura et al., "The Selective M-CSF Receptor Tyrosine Kinase Inhibitor Ki20227 Suppresses Experimental Autoimmune Encephalomyelitis," *J. Neuroimmunology*, (2008), 195: 73-80.
Uritskaya, et al., STN Accession No. 1974-27133; Document No. 08:27133; Abstract of Khimiya Geterotsiklicheskikh Soedinenii (1973), 10:1370-1373.
Vachon, et al., "The influence of microencapsulation using Eudragit RS100 on the hydrolysis kinetics of acetylsalicylic acid," *J. Microencapsulation*, (1997), 14(3):281-301.
Valent, P., "Biology, Classification and Treatment of Human Mastocytosis," *Wein/Klin Wochenschr.*, (1996), 108:385-397.
Van Heyningen, V., "One Gene—Four Syndromes," *Nature*, (1994), 367:319-320.
Vandelli, et al., "Analysis of release data in the evaluation of the physical state of progesterone in matrix systems," *J. Microencapsulation*, (1993), 10(1):55-65.
Verfaillie, C.M., "Chronic myelogenous leukemia: too much or too little growth, or both?" *Leukemia*, (1998), 12:136-138.
Viskochil, D., "It Takes Two to Tango: Mast Cell and Schwann Cell Interactions in Neurofibromas," *J Clin Invest.*, (2003), 112:1791-1793.
Vliagoftis, et al., "The protooncogene c-kit and c-kit ligand in human disease," *Journ. Clin. Immunol*, (1997), 100:435-440.
Wakefield, Basil "Fluorinated Pharmaceuticals" Innovations in Pharmaceutical Technology, (2003), 74:76-78. Online "http://web.archive/org/web/20030905122408/http://www.iptonline.com/articles/public/IPTFOUR74NP.pdf." (accessed via Wayback machine Nov. 20, 2009 showing web availability as of Sep. 2003).
Waldo et al., "Heterogeneity of human macrophages in culture and in atherosclerotic plaques," *Am. J. of Pathology*, 172(4): 1112-1126 (2008).
Weber, P., "Physical Principles of Protein Crystallization," *Adv. Protein Chem.*, (1991), 41:1-36.
Wells, et al., "Targeting the RET Pathway in Thyroid Cancer," *Clin Cancer Res.*, (2009), 15(23):7119-7123.
Wendt, et al., "Identification of novel binding interactions in the development of potent, selective 2-naphthamidine inhibitors of urokinase, synthesis, structural analysis, and SAR of y-Phenyl amide 6-substitution," *J. Med. Chem.*, (2004), 47(2):303-324.
Wentworth et al., "Pro-Inflammatory CD11C$^+$CD206$^+$ Adipose Tissue Macrophages Are Associated With Insulin Resistance in Human Obesity," *Diabetes*, (2010), 59:1648-1656.
Werness, et al., "Association of Human Papillomavirus Types 16 and 18 E6 Proteins with p53," *Science*, (1990), 248:76-79.
Wessjohann, L., "Synthesis of Natural-Product-Based Compound Libraries," *Curr Opin Chem Biol.*, (2000), 4:303-309.
Wharam, et al., "Specific Detection of DNA and RNA Targets Using a Novel Isothermal Nucleic Acid Amplification Assay Based on the Formation of a Three-Way Junction Structure," *Nucleic Acids Res.*, (2001), 29:1-8.
Wild, et al., "Antibodies to Nerve Growth Factor Reverse Established Tactile Allodynia in Rodent Models of Neuropathic Pain without Tolerance," *J. Pharmacol. Exp. Ther.*, (2007), 322:282-287.

Willmore-Payne, C., et al. "Human malignant melanoma. detection of BRAF- and c-kit-activating mutations by high-resolution amplicon melting analysis," *Humon Pathology*, (2005), 36: pp. 486-493.
Wolff, Manfred E. "Burger's Medicinal Chemistry, 5ed, Part 1", *John Wiley & Sons*, (1995), pp. 975-977.
Woon, et al., "Construction and Characterization of a 10-Fold Genome Equivalent Rat P1-Derived Artificial Chromosome Library," *Genomics*, (1998), 50:306-316.
Wright, et al., "The STE20 Kinase KGK is Broadly Expressed in Human tumor Cells and Can Modulate Cellular Transformation, Invasion, and Adhesion," *Mol. Cell. Biol.*, (2003), 23:2068-2082.
Wuthrich, K., "Chapter 10: Three-Dimensional Protein Structures by NMR," *NMR of Proteins and Nucleic Acids*, (1986), 10:176-199.
Wyckoff, et al., "Direct visualization of macrophage-assisted tumor cell intravasation in mammary tumors," *Cancer Research*, (2007), 67(6):2649-2656.
Xing, et al., "BRAF Mutation Predicts a Poorer Clinical Prognosis for Papillary Thyroid Cancer," *J. Clin. Endocrinol. Metab.*, (2005), 90(12):6373-6379.
Xing, M., "BRAF mutation in thyroid cancer," *Endocrine-Related Cancer*, (2005), 12:245-262.
Xu et al., "CSF1R signaling blockade stanches tumor-infiltrating myeloid cells and improves the efficacy of radiotherapy in prostate cancer," *Cancer Res.*, (2013), 73(9): 2782-94.
Xu, et al., "Modulation of Endothelial Cell function by Normal Polyspecific Human Intraveneous immunoglobulins," *Am. J. Path.*, (1998), 153:1257-1266.
Yakhontov, et al., "Derivatives of 7-azaindole. XV. Electrophilic substitution of 4-methyl-7-azaindole and its derivatives," *Zhumal Obshchei Khimii*, (1965), 1(11):2032-2040 (English abstract only).
Yamaguchi, et al., "Calcium Restriction Allows cAMP Activation of the B-Raf/ERK Pathway, Switching Cells to a cAMP-dependent Growth-stimulated Phenotype*," *The Journal of Biological Chemistry*, (2004), 279:40419-40430.
Yamaguchi, et al., "Cyclic AMP activates B-Raf and ERK in cyst epithelial cells from autosomal-dominant polycystic kidneys," *Kidney International*, (2003), 63:1983-1994.
Yang, et al., "Identification of Brain-Derived Neurotrophic Factor as a Novel Functional Protein in Hepatocellular Carcinoma," *Cancer Res.*, (2005), 65:219-225.
Yang, et al., "Neurofibromin-Deficient Schwann Cells Secrete a Potent Migratory Stimulus for NF1+/− Mast Cells," *J Clin Invest.*, (2003), 112:1851-1861.
Yang, et al., "Nf1-Dependent tumors require a microenvironment containing Nf1+/− -and c-kit-Dependent bone marrow," *Cell*, (2008), 135:437-448.
Yang, et al., "Synthesis of some 5-substituted indoles," *Heterocycles*, (1992), 34:1169-1175.
Yao, et al., "A Novel Human STE20-related Protein Kinase, HGK, That Specifically Activates the c-Jun N-terminal Kinase Signaling Pathway," *J. Biol. Chem.*, (1999), 274:2118-2125.
Yee, et al., "Role of kit-Ligand in Proliferation and Suppression of Apoptosis in Mast Cells: Basis for Radiosensitivity of White Spotting and Steel Mutant Mice," *J. Exp. Med.*, (1994), 179:1777-1787.
Yeung, et al., "Friedel-Crafts acylation of indoles in acidic imidazolium chloroaluminate ionic liquid at room temperature," *Tetrahedron Letters*, (2002), 43(33), 5793-5795.
Yoshida et al., "Studies on anti-helicobacter pylori agents, Part 1: Benzyloxyisoquinoline derivatives," *Bioorganic & Medicinal Chemistry, Elsevier Science Ltd*,(1999), 7(11):2647-2666.
Yuan, et al., "Human Peripheral Blood Eosinophils Express a Functional c-kit Receptor for Stem Cell Factor that Stimulates Very Late Antigen 4 (VLA-4)-Mediated Cell Adhesion to Fibronectin and Vascular Cell Adhesion Molecule 1 (VCAM-1)," *J. Exp. Med.*, (1997), 186:313-323.
Zaidi et al., "Interferon-γ links ultraviolet radiation to melanomagenesis in mice." *Nature*, (2011), 469: 548-553.
Zanon, et. al., "Copper-Catalyzed Domino Halide Exchange-Cyanation of Aryl Bromides," *J. Am. Chem. Soc.*, (2003), 125:2890-2891.

(56) References Cited

OTHER PUBLICATIONS

Zhang, et al., "An effective procedure for the acylation of azaindoles at C-3," *Journal of Organic Chemistry*, (2002), 67(17):6226-6227.
Zhang, et al., "Design and pharmacology of a highly specific dual FMS and KIT kinase inhibitor," *Proc. Natl. Acad. Sci.*, (2013), 110:(14) 5689-5694.
Notice of Allowance for U.S. Appl. No. 11/016,350 dated Dec. 26, 2007.
Office Action in U.S. Appl. No. 11/016,350 dated Aug. 2, 2007.
Office Action in U.S. Appl. No. 11/016,350 dated Jun. 6, 2007.
Office Action in U.S. Appl. No. 11/016,350 dated Oct. 26, 2007.
International Search Report and Written Opinion dated Nov. 25, 2005 for PCT Patent Application No. PCT/US2004/042470.
Supplementary Search Report for European Application No. 04814626.0 dated Aug. 4, 2009.
Communication Pursuant to Article 94(3) EPC for European Application No. 04814626.0 dated Jun. 6, 2011.
Office Action in U.S. Appl. No. 11/487,134 dated May 15, 2008.
Office Action in U.S. Appl. No. 11/487,134 dated Aug. 22, 2007.
Notice of Allowance for U.S. Appl. No. 12/082,665 dated Jul. 26, 2011.
Office Action in U.S. Appl. No. 12/082,665 dated Nov. 8, 2010.
Notice of Allowance for U.S. Appl. No. 11/154,988 dated Jun. 6, 2008.
Notice of Allowance for U.S. Appl. No. 11/154,988 dated Jul. 23, 2008.
Notice of Allowance for U.S. Appl. No. 11/154,988 dated Sep. 8, 2008.
Office Action in U.S. Appl. No. 11/154,988 dated Jan. 4, 2008.
Office Action in U.S. Appl. No. 11/154,988 dated Oct. 19, 2007.
International Search Report and Written Opinion dated Apr. 20, 2006 for PCT Patent Application No. PCT/US2005/021231.
Communication Pursuant to Article 94(3) EPC for European Application No. 05789913.0 dated Feb. 15, 2010.
Notice of Allowance for U.S. Appl. No. 12/244,730 dated Jan. 6, 2011.
Notice of Allowance for U.S. Appl. No. 12/244,730 dated Jul. 27, 2010.
Office Action in U.S. Appl. No. 12/244,730 dated Jul. 22, 2010.
Examination Report dated Jun. 27, 2008 for GCC Patent Application No. GCC/P/2005/4795.
Examination Report for Guatemala Patent Application No. PI-2005-00164 dated Jul. 2, 2008.
Search Report for Taiwan Patent Application No. 094120055 dated Aug. 25, 2011.
Notice of Allowance for U.S. Appl. No. 11/435,381 dated May 27, 2010.
Notice of Allowance for U.S. Appl. No. 11/435,381 dated Jul. 27, 2010.
Office Action in U.S. Appl. No. 11/435,381 dated Feb. 19, 2010.
Office Action in U.S. Appl. No. 11/435,381 dated Mar. 4, 2009.
Office Action in U.S. Appl. No. 11/435,381 dated Jun. 1, 2009.
International Search Report and Written Opinion dated Apr. 4, 2007 for PCT Patent Application No. PCT/US2006/018726.
Office Action in U.S. Appl. No. 12/958,376 dated Apr. 18, 2012.
Notice of Allowance for U.S. Appl. No. 11/473,347 dated Jun. 18, 2010.
Notice of Allowance for U.S. Appl. No. 11/473,347 dated Sep. 8, 2010.
Office Action in U.S. Appl. No. 11/473,347 dated Dec. 18, 2009.
International Search Report and Written Opinion dated Oct. 24, 2006 for PCT Patent Application No. PCT/US2006/024524.
Notice of Allowance for U.S. Appl. No. 12/616,079 dated Oct. 25, 2012.
Office Action in U.S. Appl. No. 12/616,079 dated Feb. 9, 2012.
Office Action in U.S. Appl. No. 12/616,079 dated Jun. 29, 2012.
Office Action in U.S. Appl. No. 12/906,980 dated Feb. 29, 2012.
Office Action in U.S. Appl. No. 12/906,980 dated Oct. 17, 2012.
Notice of Allowance for U.S. Appl. No. 13/216,200 dated Dec. 8, 2011.
Office Action in U.S. Appl. No. 13/243,748 dated Jun. 27, 2013.
Office Action in U.S. Appl. No. 13/786,219 dated Jul. 21, 2014.
Office Action in U.S. Appl. No. 13/786,219 dated Nov. 8, 2013.
Office Action in U.S. Appl. No. 13/866,469 dated Oct. 31, 2013.
Office Action in Taiwan Application No. 102123382 dated Nov. 16, 2013.
International Search Report and Written Opinion dated Oct. 24, 2006 for PCT Patent Application No. PCT/US2006/024361.
Examination Report dated Sep. 18, 2009 for Gulf Cooperation Council Application No. GCC/P/2006/6469.
Novelty Search Report dated Sep. 24, 2009 for Gulf Cooperation Council Application No. GCC/P/2006/6469.
Examination Report for Pakistan Patent Application No. 0679/2006.
Office Action in Taiwan Application No. 095122373 dated Dec. 9, 2011.
Office Action in Australian Application No. 2006261993 dated Aug. 15, 2011.
Office Action in Colombian Application No. 08-005.567 dated Sep. 9, 2011.
Exam Report in Egyptian Application No. 1439/2007 dated Nov. 3, 2014.
Communication Pursuant to Article 94(3) EPC for European Application No. 06773861.7 dated Apr. 22, 2010.
Communication Pursuant to Article 94(3) EPC for European Application No. 06773861.7 dated Jul. 9, 2009.
Communication Pursuant to Article 94(3) EPC for European Application No. 06773861.7 dated Dec. 21, 2009.
Office Action in Japanese Application No. 2008-518402 dated Nov. 29, 2011.
Office Action in Norwegian Application No. 20076659 dated Aug. 15, 2012.
Office Action in Ukrainian Application No. a2008-00780 dated Mar. 3, 2012.
Notification on the Result of Substantive Examination dated Oct. 17, 2014 for Vietnamese Application No. 1-2010-02238.
Communication Pursuant to Article 94(3) EPC for European Appln. No. 11173701.1 dated Jan. 4, 2013.
Search Report for European Application No. 11173701.1 dated Mar. 6, 2012.
Search Report for European Application No. 11173701.1 dated Oct. 26, 2011.
Substative Communication for European Application No. 11173701.1 dated Jan. 13, 2014.
Office Action in Malaysian Applictaion No. PI2011004969 dated Apr. 30, 2014.
Notice of Allowance for U.S. Appl. No. 11/962,044 dated Aug. 13, 2010.
Office Action in U.S. Appl. No. 11/962,044 dated Feb. 17, 2010.
Office Action in U.S. Appl. No. 11/962,044 dated Sep. 23, 2009.
International Search Report and Written Opinion dated Jul. 25, 2008 for PCT Patent Application No. PCT/US2007/088443.
International Search Report and Written Opinion dated Nov. 17, 2008 for PCT Patent Application No. PCT/US2007/088412.
Notice of Allowance for U.S. Appl. No. 11/961,901 dated May 17, 2012.
Office Action in U.S. Appl. No. 11/961,901 dated Jan. 23, 2012.
Office Action in U.S. Appl. No. 11/961,901 dated Aug. 4, 2011.
International Search Report and Written Opinion dated Jul. 3, 2008 for PCT Patent Application No. PCT/US2007/088243.
Notice of Allowance for U.S. Appl. No. 11/960,590 dated Aug. 11, 2010.
International Search Report and Written Opinion dated Jun. 4, 2008 for PCT Patent Application No. PCT/US2007/088231.
Office Action in U.S. Appl. No. 12/981,427 dated Mar. 5, 2013.
International Search Report and Written Opinion dated Jun. 4, 2008 for PCT Patent Application No. PCT/US2007/088237.
Office Action in Peruvian Application No. 1796-2007 dated Sep. 15, 2011.
Notification Prior to Examination (English translation) dated May 4, 2010 for Israeli Application No. 199194.
Malaysian Examination Report dated Aug. 15, 2012 in related Malaysian Application Serial No. PI20092547.

(56) References Cited

OTHER PUBLICATIONS

Office Action in New Zealand Application No. 577612 dated Mar. 21, 2012.
Office Action in Philippine Application No. 1-2009-501241 dated Jul. 27, 2012.
Office Action in Russian Application No. 2009122436 dated Dec. 2, 2011.
Communication Pursuant to Article 94(3) EPC for European Application No. 06813186.1 dated Sep. 15, 2009.
International Search Report and Written Opinion dated Jun. 5, 2008 for PCT Patent Application No. PCT/US2007/083910.
International Search Report and Written Opinion dated Jun. 5, 2008 for PCT Patent Application No. PCT/US2007/085289.
Office Action in Peruvian Application No. 1602-2007 dated Sep. 2, 2011.
Office Action in Chinese Application No. 200780050245.3 dated Jul. 20, 2011.
Office Action in Israeli Application No. 198624 dated Apr. 18, 2012.
Malaysian Substantive Examination Report dated Aug. 15, 2012 in related Malaysian Application Serial No. PI20092040.
Examination Report dated Mar. 14, 2012 in related New Zealand Patent Application Serial No. 577011.
Office Action in Philippines Application No. 12009501009 dated Jul. 27, 2012.
Office Action in Phillipines Application No. 12009501009 dated Nov. 24, 2011.
Office Action in Russian Application No. 2009117475 dated Jul. 26, 2011.
Examination Report in Australian Patent Application Serial No. 2007323644 dated Mar. 13, 2012.
Office Action in Japanese Application No. 2009-538496 dated Jan. 29, 2013.
Office Action in Japanese Application No. 2009-538496 dated Aug. 20, 2013.
Communication Pursuant to Article 94(3) EPC for European Appln. No. 07864681.7 dated Oct. 8, 2012.
Communication Pursuant to Article 94(3) EPC for European Application No. 07864681.7 dated Dec. 2, 2009.
International Search Report and Written Opinion dated Jul. 28, 2008 for PCT Patent Application No. PCT/US2007/085299.
Notice of Allowance for U.S. Appl. No. 11/986,667 dated Aug. 6, 2010.
Office Action in U.S. Appl. No. 11/986,667 dated Feb. 26, 2010.
Office Action in U.S. Appl. No. 11/986,667 dated Sep. 22, 2009.
Office Action in U.S. Appl. No. 12/958,379 dated Jul. 17, 2012.
Office Action in U.S. Appl. No. 12/958,379 dated Nov. 14, 2012.
Notice of Allowance for U.S. Appl. No. 13/546,923 dated Nov. 19, 2012.
Office Action in U.S. Appl. No. 13/546,923 dated Sep. 18, 2012.
Office Action in U.S. Appl. No. 12/467,194 dated Feb. 3, 2011.
Notice of Allowance for U.S. Appl. No. 12/467,194 dated Dec. 5, 2011.
Office Action in U.S. Appl. No. 12/467,194 dated Jun. 24, 2011.
International Search Report and Written Opinion dated Feb. 18, 2010 for PCT Patent Application No. PCT/US2009/044151.
International Search Report and Written Opinion dated Sep. 22, 2009 for PCT Patent Application No. PCT/US2009/046598.
Office Action in U.S. Appl. No. 12/733,798 dated Jan. 20, 2011.
Office Action in U.S. Appl. No. 12/773,798 dated Jul. 25, 2011.
Notice of Allowance for U.S. Appl. No. 12/773,798 dated Feb. 9, 2012.
International Search Report dated Sep. 13, 2010 in related application PCT/US2010/033571.
International Preliminary Report on Patentability dated Nov. 9, 2011 in related application PCT/US2010/033576.
International Search Report with Written Opinion dated Jun. 30, 2010 in related application PCT/US2010/033576.
International Search Report and Written Opinion dated Sep. 23, 2011 for PCT Patent Application No. PCT/US2010/061601.

Extended European Search Report for EP Application 100840075.5 dated May 13, 2013.
Office Action in Japanese Application No. 2012-546158 dated Dec. 2, 2014.
International Search Report and Written Opinion dated Jan. 14, 2011 for PCT Patent Application No. PCT/US2010/055519.
Office Action in Israeli Application No. 219418 dated Oct. 6, 2014.
Office Action and Search Report for Taiwanese Application No. 100113512 dated Dec. 15, 2014.
International Search Report dated Dec. 19, 2011 in related application PCT/US2011/033192.
Supplementary European Search Report for EP Application No. 11772612, dated Oct. 21, 2013.
International Search Report and Written Opinion dated Jan. 25, 2011for PCT Patent Application No. PCT/US2010/057293.
Extended European Search Report for EP Application 10832209.0 dated Apr. 17, 2013.
Office Action in Russian Application No. 2012125070 dated Dec. 5, 2014.
International Search Report and Written Opinion dated Jun. 11, 2010 for PCT Patent Application No. PCT/US2010/026816.
Office Action in U.S. Appl. No. 12/721,500 dated May 13, 2011.
Notice of Allowance for U.S. Appl. No. 12/721,500 dated Nov. 2, 2011.
International Search Report and Written Opinion dated Jun. 11, 2010 for PCT Patent Application No. US2010/026856.
Office Action in U.S. Appl. No. 12/752,035 dated Jun. 18, 2013.
Office Action in U.S. Appl. No. 12/752,035 dated Oct. 3, 2012.
International Search Report and Written Opinion dated Oct. 5, 2010 for PCT Patent Application No. PCT/US2010/029489.
Office Action in Taiwan Application No. 099110011 dated Jun. 26, 2012.
Office Action in Canadian Application No. 2,738,573 dated Jan. 10, 2012.
Examiners Report in Australian Application No. 2010232670 dated Jun. 6, 2014.
Office Action in Chinese Application No. 201080012888.0 dated Mar. 10, 2014.
Office Action in Chinese Application No. 20108001288.0 dated Oct. 21, 2014.
Office Action in Dominican Republic Application No. P2011-0291 dated Apr. 23, 2012.
Office Action in Eurasion Application No. 20119098 dated Jun. 16, 2014.
Office Action in Eurasian Application No. 201190098 dated Jan. 13, 2014.
Office Action in Indonesian Application No. W-00 2011-02778 dated Nov. 7, 2014.
Office Action in Israeli Application No. 214328 dated Jul. 31, 2013.
Office Action, in related Japense Patent Application No. 2012-503676 dated May 21, 2013.
Office Action in Mexican Application No. MX/a/2011/008303 dated Sep. 11, 2014.
Office Action in New Zealand Application No. 594398 dated Aug. 16, 2012.
Office Action in Peru Applicantion No. 1471-2011 dated Mar. 23, 2014.
Office Action in Ukraine Application No. a 2011 09548 dated Jun. 4, 2014.
Office Action in European Application 10722860.3 dated Aug. 21, 2014.
Supplementary European Search Report for European Patent Application No. EP1278 9648 dated Jul. 7, 2014.
Communication Pursuant to Article 94(3) EPC for European Application No. 10722860.3 dated Mar. 27, 2013.
International Search Report and Written Opinion dated May 31, 2012 for PCT Patent Application No. PCT/US2012/023543.
Office Action for Australian Application No. 2012214762 dated Mar. 23, 2014.
Office Action dated Jul. 8, 2014 for Chinese Application No. 2012800170177.
Search Report for European Application No. 12745360.3 dated Jul. 23, 2014.

(56) References Cited

OTHER PUBLICATIONS

Office Action in Japanese Application No. 2013-552610 dated Nov. 4, 2014.
Examination Report in New Zealand Application No. 613786 dated May 5, 2014.
Office Action for Thai Application No. 1301004352 dated Sep. 29, 2014.
International Search Report dated Aug. 10, 2012 for PCT/US2012/038417.
Office Action in New Zealand Application No. 617526 dated Aug. 14, 2014.
Exam Report in Australian Application No. 2012200933 dated Jul. 3, 2013.
Office Action in U.S. Appl. No. 12/669,450 dated Dec. 27, 2012.
Greene et al., "Protective Groups in Organic Synthesis," 1999, p. 603-615.

* cited by examiner

SYNTHESIS OF HETEROCYCLIC COMPOUNDS

CROSS REFERENCE TO RELATED APPLICATIONS

This application is a continuation of U.S. application Ser. No. 13/793,917, filed Mar. 11, 2013, which claims the benefit under 35 U.S.C. §119(e) of U.S. Provisional Application No. 61/653,994, filed on May 31, 2012, which is incorporated by reference in its entirety.

FIELD OF THE INVENTION

The present invention relates to heterocyclic compounds, methods for the preparation thereof, and compounds prepared employing same.

BACKGROUND OF THE INVENTION

N-[3-[5-(4-chlorophenyl)-1H-pyrrolo[2,3-b]pyridine-3-carbonyl]-2,4-difluoro-phenyl]propane-1-sulfonamide or propane-1-sulfonic acid {3-[5-(4-chloro-phenyl)-1H-pyrrolo[2,3-b]pyridine-3-carbonyl]-2,4-difluorophenyl}-amide (Vemurafenib; Zelboraf™) is effective for the treatment of various B-raf mediated diseases and conditions, including, but not limited to, metastatic melanoma, thyroid cancers and colorectal cancers (*Nature*, 2010, 467, 596-599; *New England Journal of Medicine*, 2010, 363, 80). The compound and its synthesis have been described in PCT Patent Publication Nos. WO 2007/002433 and WO 2007/002325. There remains interest in developing other versatile and facile processes for the efficient preparation of this and other biologically active molecules, especially, on an industrial scale.

SUMMARY OF THE INVENTION

In one aspect, the present invention provides a compound of formula (I):

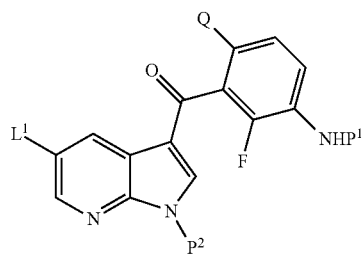

(I)

The compound can be used as an intermediate for the synthesis of various biologically active molecules. In formula (I):
Q is F or H;
$P^1$ is hydrogen or a labile protecting group;
$P^2$ is an amino protecting group or hydrogen; and
$L^1$ is Br, Cl, I, $R^1$—$SO_2O$— or $R^2C(O)O$; wherein $R^1$ and $R^2$ are each independently optionally substituted aryl or optionally substituted $C_{1-6}$alkyl.
In one embodiment, $P^1$ is H. In another embodiment, Q is F; $P^1$ is H; and $L^1$ is Br.

In another aspect, the present invention provides a method for preparing a compound of formula (I). The method comprises contacting a compound of formula (II):

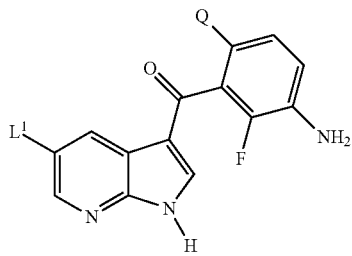

(II)

with an agent having the formula: $P^2$—$X^1$ under conditions sufficient to form the compound of formula (Ia):

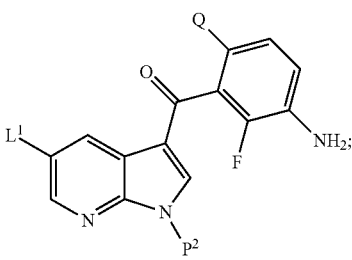

(Ia)

and contacting a compound of formula (Ia) with an agent of formula: $P^1$—$X^3$ under conditions sufficient to form the compound of formula (I), wherein:
$X^1$ is selected from Br, Cl, I, tosyl-O—, mesyl-O—, trifluoromethanesulfonyl-O—, $CF_3C(O)O$— or $CH_3C(O)O$—;
$X^3$ is a leaving group;
$P^1$ is hydrogen or a labile protecting group;
$P^2$ is an amino protecting group;
Q is H or F; and
$L^1$ is Br, Cl, I, $R^1$—$SO_2O$— or $R^2C(O)O$; wherein $R^1$ and $R^2$ are each independently optionally substituted aryl or optionally substituted $C_{1-6}$alkyl.

In yet another aspect, the present invention provides a method for preparing a compound of formula (III):

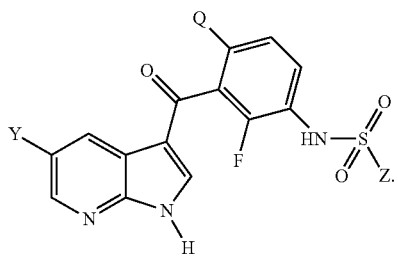

(III)

The method comprises
(i) contacting a compound of formula (I) with an agent having the formula: Y—$B(OR^5)_2$ (i.e., formula IVb) or the formula: Y—$Sn(Bu)_3$ (i.e., formula IVc) and a palladium or a nickel complex under conditions sufficient to form a compound of formula (IV):

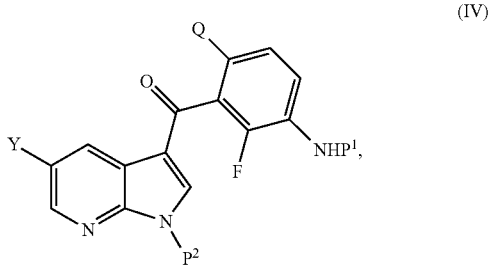

(IV)

(ii) reacting a compound of formula (IV) with an agent of the formula: $A^1$-S(O)$_2$—Z (i.e., formula IVa) under conditions sufficient to form a compound of formula (IX);

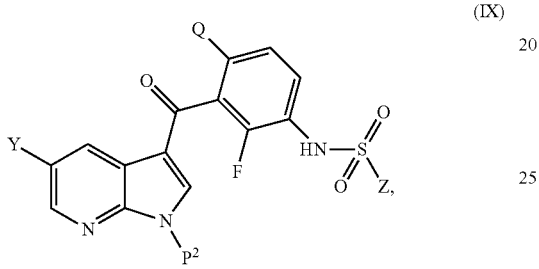

(IX)

and (iii) removing the protecting group $P^2$ under conditions sufficient to form the compound of formula (III), wherein:

Q is H or F;

$R^5$ is OH, $C_{1-6}$alkyl or two —OR$^5$ substituents together with the boron atom to which they are attached form an optionally substituted 5 or 6-membered ring;

$A^1$ is a leaving group;

Y is optionally substituted aryl or optionally substituted heteroaryl; and

Z is —N(R$^6$)(R$^7$) or —C(R$^8$)(R$^9$)(R$^{10}$); wherein:

R$^6$ and R$^7$ are each independently selected from the group consisting of H, optionally substituted $C_{1-6}$alkyl, optionally substituted $C_{3-8}$cycloalkyl, optionally substituted $C_{3-8}$cycloalkylalkyl, optionally substituted heterocycloalkyl, optionally substituted heterocycloalkylalkyl, optionally substituted aryl, optionally substituted arylalkyl, optionally substituted heteroaryl and optionally substituted heteroarylalkyl; or R$^6$ and R$^7$ taken together with the nitrogen atom to which they are attached form a four to eight-membered ring having from 0-2 additional heteroatoms as ring members selected from N, O or S, wherein the four to eight-membered ring is optionally substituted; and R$^8$, R$^9$ and R$^{10}$ are each independently H, optionally substituted $C_{1-6}$alkyl, optionally substituted, $C_{1-6}$haloalkyl, optionally substituted $C_{1-6}$haloalkoxy, optionally substituted $C_{3-8}$cycloalkyl, optionally substituted $C_{3-8}$cycloalkylalkyl, optionally substituted aryl, optionally substituted arylalkyl, optionally substituted heterocycloalkyl, optionally substituted heterocycloalkylalkyl, optionally substituted heteroaryl, optionally substituted heteroarylalkyl or —X$^2$R$^{11}$, wherein X$^2$ is —NR$^{12}$, O or S; R$^{12}$ is H, $C_{1-6}$alkyl or aryl; and R$^{11}$ is H, $C_{1-6}$alkyl, $C_{1-6}$haloalkyl, $C_{1-6}$haloalkoxy, $C_{3-8}$cycloalkyl, $C_{3-8}$cycloalkylalkyl, aryl, arylalkyl, heteroaryl or heteroarylalkyl, wherein R$^{11}$ is optionally substituted with from 1 to 3 R$^e$ substituents selected from halogen, —CN, —CH═CH$_2$, —OH, —NH$_2$, —NO$_2$, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^f$, —SR$^f$, —OC(O)R$^f$, —OC(S)R$^f$, —C(O)R$^f$, —C(S) R$^f$, —C(O)OR$^f$, —C(S)OR$^f$, —S(O)R$^f$, —S(O)$_2$R$^f$, —C(O)NHR$^f$, —C(S)NHR$^f$, —C(O)NR$^f$R$^f$, —C(S) NR$^f$R$^f$, —S(O)$_2$NHR$^f$, —S(O)$_2$NR$^f$R$^f$, —C(NH) NHR$^f$, —C(NH)NR$^f$R$^f$, —NHC(O)R$^f$, —NHC(S)R$^f$, —NR$^f$C(O)R$^f$, —NR$^f$C(S)R$^f$, —NHS(O)$_2$R$^f$, —NR$^f$S(O)$_2$R$^f$, —NHC(O)NHR$^f$, —NHC(S)NHR$^f$, —NR$^f$C(O)NH$_2$, —NR$^f$C(S)NH$_2$, —NR$^f$C(O)NHR$^f$, —NR$^f$C(S)NHR$^f$, —NHC(O)NR$^f$R$^f$, —NHC(S) NR$^f$R$^f$, —NR$^f$C(O)NR$^f$R$^f$, —NR$^f$C(S)NR$^f$R$^f$, —NHS(O)$_2$NHR$^f$, —NR$^f$S(O)$_2$NH$_2$, —NR$^f$S(O)$_2$NHR$^f$, —NHS(O)$_2$NR$^f$R$^f$, —NR$^f$S(O)$_2$NR$^f$R$^f$, —NHR$^f$, —NR$^f$R$^f$ and R$^f$, wherein R$^f$ is $C_{1-6}$alkyl, $C_{3-6}$cycloalkyl, heterocycloalkyl, heteroaryl or aryl, wherein R$^f$ is optionally substituted with from 1-3 R$^g$ substituents selected from —CN, —CH═CH$_2$, —OH, —NH$_2$, —NO$_2$, —C(O)OH, —C(S)OH, —C(O)NH$_2$, —C(S)NH$_2$, —S(O)$_2$NH$_2$, —NHC(O) NH$_2$, —NHC(S)NH$_2$, —NHS(O)$_2$NH$_2$, —C(NH) NH$_2$, —OR$^h$, —SR$^h$, —OC(O)R$^h$, —OC(S)R$^h$, —C(O)R$^h$, —C(S)R$^h$, —C(O)OR$^h$, —C(S)OR$^h$, —S(O)R$^h$, —S(O)$_2$R$^h$, —C(O)NHR$^h$ or R$^h$, wherein R$^h$ is $C_{1-6}$alkyl; or any two of the R$^8$, R$^9$ and R$^{10}$ groups taken together with the carbon atom to which they are attached form a 3 to 8-membered optionally substituted non-aromatic ring having from 0 to 2 heteroatoms selected from N, O or S.

DETAILED DESCRIPTION OF THE INVENTION

The present invention is related to novel synthetic intermediates and processes for the large-scale preparation of compounds that have the following core structure (aa):

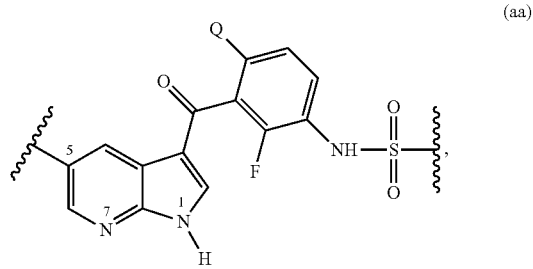

(aa)

namely, [2,6-difluoro-3-(sulfonylamino)phenyl]-(1H-pyrrolo[2,3-b]pyridin-3-yl)methanone core or [2-fluoro-3-(sulfonylamino)phenyl]-(1H-pyrrolo[2,3-b]pyridin-3-yl)methanone core. The wavy lines indicate the points of attachment to the remainder of the structure. In some embodiments, the 5-position of the 7-azaindole ring in the core structure (aa) is occupied with the substituent Y and the sulfonyl group is linked to the substituent Z. The variables Q, Y and Z are as defined in the Summary of the Invention and any of the embodiments as described herein. For example, the present invention provides synthetic methods and intermediates useful for the large scale preparation of N-[3-[5-(4-chloro-phenyl)-1H-pyrrolo[2,3-b]pyridine-3-carbonyl]-2,4-difluoro-phenyl]propane-1-sulfonamides or propane-1-sulfonic acid {3-[5-(4-chloro-phenyl)-1H-pyrrolo[2,3-b]pyridine-3-carbonyl]-2,4-difluorophenyl}-amides.

Advantageously, the present invention provides synthetic intermediates and versatile processes, which allow for high efficiency, low cost and large-scale facile synthesis of biologically active molecules including vemurafenib with high purity. The intermediates of the present invention can be readily adapted to the facile preparation of various compounds having core structure (aa).

DEFINITIONS

It is noted here that as used in this specification and the appended claims, the singular forms "a," "an," and "the" include plural reference unless the context clearly dictates otherwise.

"Halogen" or "halo" refers to all halogens, that is, chloro (Cl), fluoro (F), bromo (Br), or iodo (I).

"Hydroxyl" or "hydroxy" refers to the group —OH.

"Thiol" refers to the group —SH.

The term "alkyl", by itself or as part of another substituent, means, unless otherwise stated, a straight or branched chain hydrocarbon, having the number of carbon atoms designated (i.e. $C_{1-6}$ means one to six carbons). Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms. Examples of alkyl groups include methyl, ethyl, n-propyl, isopropyl, n-butyl, t-butyl, isobutyl, sec-butyl, n-pentyl, n-hexyl, n-heptyl, n-octyl, and the like. For each of the definitions herein (e.g., alkyl, alkoxy, alkylamino, alkylthio, alkylene, haloalkyl, arylalkyl, cycloalkylalkyl, heterocycloalkylalkyl, heteroarylalkyl), when a prefix is not included to indicate the number of carbon atoms in an alkyl portion, the alkyl moiety or portion thereof will have 12 or fewer main chain carbon atoms or 8 or fewer main chain carbon atoms or 6 or fewer main chain carbon atoms. For example, $C_{1-8}$ alkyl refers to a straight or branched hydrocarbon having 1, 2, 3, 4, 5 or 6 carbon atoms and includes, but are not limited to, $C_{1-2}$ alkyl, $C_{1-4}$ alkyl, $C_{2-6}$ alkyl, $C_{2-4}$ alkyl, $C_{1-6}$ alkyl, $C_{2-8}$ alkyl, $C_{1-7}$ alkyl, $C_{2-7}$ alkyl and $C_{3-6}$ alkyl. "Fluoro substituted alkyl" denotes an alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. While it is understood that substitutions are attached at any available atom to produce a stable compound, when optionally substituted alkyl is an R group of a moiety such as —OR (e.g. alkoxy), —SR (e.g. thioalkyl), —NHR (e.g. alkylamino), —C(O)NHR, and the like, substitution of the alkyl R group is such that substitution of the alkyl carbon bound to any O, S, or N of the moiety (except where N is a heteroaryl ring atom) excludes substituents that would result in any O, S, or N of the substituent (except where N is a heteroaryl ring atom) being bound to the alkyl carbon bound to any O, S, or N of the moiety.

The term "alkylene" by itself or as part of another substituent means a linear or branched saturated divalent hydrocarbon moiety derived from an alkane having the number of carbon atoms indicated in the prefix. For example, (i.e. $C_{1-6}$ means one to six carbons; $C_{1-6}$ alkylene is meant to include methylene, ethylene, propylene, 2-methylpropylene, pentylene, hexylene and the like). $C_{1-4}$ alkylene includes methylene —CH$_2$—, ethylene —CH$_2$CH$_2$—, propylene —CH$_2$CH$_2$CH$_2$—, and isopropylene —CH(CH$_3$)CH$_2$—, —CH$_2$CH(CH$_3$)—, —CH$_2$—(CH$_2$)$_2$CH$_2$—, —CH$_2$—CH(CH$_3$)CH$_2$—, —CH$_2$—C(CH$_3$)$_2$—, —CH$_2$—CH$_2$CH(CH$_3$)—. Typically, an alkyl (or alkylene) group will have from 1 to 24 carbon atoms, with those groups having 10 or fewer, 8 or fewer, or 6 or fewer carbon atoms being preferred in the present invention. When a prefix is not included to indicate the number of carbon atoms in an alkylene portion, the alkylene moiety or portion thereof will have 12 or fewer main chain carbon atoms or 8 or fewer main chain carbon atoms, 6 or fewer main chain carbon atoms or 4 or fewer main chain carbon atoms.

"Cycloalkylalkyl" refers to an -(alkylene)-cycloalkyl group where alkylene as defined herein has the indicated number of carbon atoms or if unspecified having six or fewer, preferably four or fewer main chain carbon atoms; and cycloalkyl is as defined herein has the indicated number of carbon atoms. $C_{3-8}$cycloalkyl-$C_{1-2}$alkyl means $C_{3-8}$cycloalkyl-$C_{1-2}$alkylene, wherein the cycloalkyl has 3 to 8 ring carbon atoms and the alkylene has 1 or 2 carbon atoms. Exemplary cycloalkylalkyl include, e.g., cyclopropylmethylene, cyclobutylethylene, cyclobutylmethylene, and the like.

"Cycloalkyl" by itself or as part of another substituent, refers to saturated or unsaturated, non-aromatic monocyclic, bicyclic or tricyclic carbon ring systems of 3-10, also 3-8, more preferably 3-6, ring members per ring, such as cyclopropyl, cyclopentyl, cyclohexyl, 1-cyclohexenyl, adamantyl, and the like. Cycloalkyl refers to hydrocarbon rings having the indicated number of ring atoms (e.g., $C_{3-8}$ cycloalkyl means three to eight ring carbon atoms).

"Haloalkyl," is meant to include alkyl substituted by one to seven halogen atoms. Haloalkyl includes monohaloalkyl and polyhaloalkyl. For example, the term "$C_{1-6}$ haloalkyl" is meant to include trifluoromethyl, difluoromethyl, 2,2,2-trifluoroethyl, 4-chlorobutyl, 3-bromopropyl, and the like.

"Haloalkoxy" refers to a —O-haloalkyl group, where haloalkyl is as defined herein, e. g., trifluoromethoxy, 2,2,2-trifluoroethoxy, difluoromethoxy, and the like.

"Alkoxy" refers to a —O-alkyl group, where alkyl is as defined herein. "Cycloalkoxy" refers to a —O-cycloalkyl group, where cycloalkyl is as defined herein. "Fluoro substituted alkoxy" denotes alkoxy in which the alkyl is substituted with one or more fluoro atoms, where preferably the alkoxy is substituted with 1, 2, 3, 4 or 5 fluoro atoms, also 1, 2, or 3 fluoro atoms. While it is understood that substitutions on alkoxy are attached at any available atom to produce a stable compound, substitution of alkoxy is such that O, S, or N (except where N is a heteroaryl ring atom), are not bound to the alkyl carbon bound to the alkoxy O. Further, where alkoxy is described as a substituent of another moiety, the alkoxy oxygen is not bound to a carbon atom that is bound to an O, S, or N of the other moiety (except where N is a heteroaryl ring atom), or to an alkene or alkyne carbon of the other moiety.

"Amino" or "amine" denotes the group —NH$_2$.

"Alkylamino" refers to a NH-alkyl group, where alkyl is as defined herein. Exemplary alkylamino groups include CH$_3$NH—, ethylamino, and the like.

"Dialkylamino" refers to a —N(alkyl)(alkyl) group, where each alkyl is independently as defined herein. Exemplary dialkylamino groups include dimethylamino, diethylamino, ethylmethylamino, and the like.

"Cycloalkylamino" denotes the group —NR$^{dd}$R$^{ee}$, where R$^{dd}$ and R$^{ee}$ combine with the nitrogen to form a 5-7 membered heterocycloalkyl ring, where the heterocycloalkyl may contain an additional heteroatom within the ring, such as O, N, or S, and may also be further substituted with alkyl, haloalkyl, haloalkoxy, alkoxy, aryl, heteroaryl, arylalkyl, heteroarylalkyl, cycloalkyl, cycloalkylalkyl or R' as defined herein. Alternatively, "cycloalkylamino" refers to a —NH-cycloalkyl group, where cycloalkyl is as defined herein.

"Arylamino" refers to a —NH-aryl group, where aryl is as defined herein. Exemplary arylamino groups include PhNH—, naphthylamino, and the like.

"Heteroarylamino" refers to a NH-heteroaryl group, where heteroaryl is as defined herein. Exemplary heteroarylamino groups include pyridinyl-NH—, pyrimidinyl-amino, and the like.

"Aryl" by itself or as part of another substituent refers to a monocyclic, bicyclic or polycyclic polyunsaturated aromatic hydrocarbon moiety containing 6 to 14 ring carbon atoms. Non-limiting examples of unsubstituted aryl groups include phenyl, 1-naphthyl, 2-naphthyl and 4-biphenyl. Exemplary aryl group, such as phenyl or naphthyl, which may be optionally fused with a cycloalkyl of preferably 5-7, more preferably 5-6, ring members.

"Arylalkyl" refers to -(alkylene)-aryl, where the alkylene group is as defined herein and has the indicated number of carbon atoms, or if unspecified having six or fewer main chain carbon atoms or four or fewer main chain carbon atoms; and aryl is as defined herein. For example, aryl-$C_{1-2}$alkyl means aryl-alkylene-, where the alkylene has 1 or 2 carbon atoms. Examples of arylalkyl include benzyl, phenethyl, and the like.

"Heteroaryl" by itself or as part of another substituent refers to a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridinyl, pyridazinyl, pyrazinyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, indolyl, triazinyl, quinoxalinyl, cinnolinyl, phthalaziniyl, benzotriazinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzothienyl, quinolyl, isoquinolyl, indazolyl, pteridinyl and thiadiazolyl. "Nitrogen containing heteroaryl" refers to heteroaryl wherein any heteroatoms are N.

"Heteroarylalkyl" refers to -(alkylene)-heteroaryl, where the alkylene group is as defined herein and has the indicated number of carbon atoms, or if unspecified having six or fewer main chain carbon atoms or four or fewer main chain carbon atoms; and heteroaryl is as defined herein. For example, heteroaryl-$C_{1-2}$alkyl means heteroaryl-alkylene-, where the alkylene has 1 or 2 carbon atoms. Examples of heteroarylalkyl include 2-pyridylmethyl, 2-thiazolylethyl, and the like.

"Heterocycloalkyl" refers to a saturated or unsaturated non-aromatic cycloalkyl group that contains from one to five heteroatoms selected from N, O, and S, wherein the nitrogen and sulfur atoms are optionally oxidized, and the nitrogen atom(s) are optionally quaternized, the remaining ring atoms being C, where one or two C atoms may optionally be replaced by a carbonyl. The heterocycloalkyl may be a monocyclic, a bicyclic or a polycylic ring system of 3 to 12, preferably 4 to 10 ring atoms, more preferably 5 to 8 ring atoms, even more preferably 4-6 ring atoms in which one to five ring atoms are heteroatoms selected from —N=, —N—, —O—, —S—, —S(O)—, or $S(O)_2$— and further wherein one or two ring atoms are optionally replaced by a —C(O)— group. The heterocycloalkyl can also be a heterocyclic alkyl ring fused with a cycloalkyl, an aryl or a heteroaryl ring. Non limiting examples of heterocycloalkyl groups include pyrrolidinyl, piperidinyl, imidazolidinyl, pyrazolidinyl, butyrolactam moiety, valerolactam moiety, imidazolidinone moiety, hydantoin, dioxolane moiety, phthalimide moiety, piperidine, 1,4-dioxane moiety, morpholinyl, thiomorpholinyl, thiomorpholinyl-S-oxide, thiomorpholinyl-S,S-oxide, piperazinyl, pyranyl, pyridine moiety, 3-pyrrolinyl, thiopyranyl, pyrone moiety, tetrahydrofuranyl, tetrahydrothiophenyl, quinuclidinyl, and the like. A heterocycloalkyl group can be attached to the remainder of the molecule through a ring carbon or a heteroatom.

"Heterocycloalkylalkyl" refers to -(alkylene)-heterocycloalkyl, where the alkylene group is as defined herein and has the indicated number of carbon atoms, or if unspecified having six or fewer main chain carbon atoms or four or fewer main chain carbon atoms; and heterocycloalkyl is as defined herein. Examples of heterocycloalkylalkyl include 2-pyridylmethyl, 2-thiazolylethyl, and the like.

The substituents for alkyl, alkoxy, haloalkyl, haloalkoxy, cycloalkyl, cycloalkylalkyl, alkylene, vinyl include, but are not limited to, R', halogen, —OH, $—NH_2$, $—NO_2$, —CN, —C(O)OH, —C(S)OH, $—C(O)NH_2$, $—C(S)NH_2$, $—S(O)_2NH_2$, $—NHC(O)NH_2$, $—NHC(S)NH_2$, $—NHS(O)_2NH_2$, $—C(NH)NH_2$, —OR', —SR', —OC(O)R', —OC(S)R', —C(O)R', —C(S)R', —C(O)OR', —C(S)OR', —S(O)R', $—S(O)_2R'$, —C(O)NHR', —C(S)NHR', —C(O)NR'R", —C(S)NR'R", $—S(O)_2NHR'$, $—S(O)_2NR'R"$, —C(NH)NHR', —C(NH)NR'R", —NHC(O)R', —NHC(S)R', —NR"C(O)R', —NR'C(S)R", $—NHS(O)_2R'$, —NR'S$(O)_2R"$, —NHC(O)NHR', —NHC(S)NHR', —NR'C(O)$NH_2$, $—NR'C(S)NH_2$, —NR'C(O)NHR", —NR'C(S)NHR", —NHC(O)NR'R", —NHC(S)NR'R", —NR'C(O)NR"R'", —NR'"C(S)NR'R", $—NHS(O)_2NHR'$, $—NR'S(O)_2NH_2$, $—NR'S(O)_2NHR"$, $—NHS(O)_2NR'R"$, $—NR'S(O)_2NR"R'"$, —NHR', and —NR'R" in a number ranging from zero to (2m'+1), where m' is the total number of carbon atoms in such group. R', R" and R'" each independently refer to hydrogen, $C_{1-8}$ alkyl, heterocycloalkyl, aryl, heteroaryl, arylalkyl, heteroarylalkyl, aryl substituted with 1-3 halogens, $C_{1-8}$ alkoxy, haloalkyl, haloalkoxy or $C_{1-8}$ thioalkoxy groups, or unsubstituted aryl-$C_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. R', R" and R'" can be further substituted with $R^{a1}$, halogen, —OH, $—NH_2$, $—NO_2$, —CN, —C(O)OH, —C(S)OH, $—C(O)NH_2$, $—C(S)NH_2$, $—S(O)_2NH_2$, $—NHC(O)NH_2$, $—NHC(S)NH_2$, $—NHS(O)_2NH_2$, $—C(NH)NH_2$, $—OR^{a1}$, $—SR^{a1}$, —OC(O)$R^{a1}$, $—OC(S)R^{a1}$, $—C(O)R^{a1}$, $—C(S)R^{a1}$, $—C(O)OR^{a1}$, $—C(S)OR^{a1}$, $—S(O)R^{a1}$, $—S(O)_2R^{a1}$, $—C(O)NHR^{a1}$, $—C(S)NHR^{a1}$, $—C(O)NR^{a1}R^{a2}$, $—C(S)NR^{a1}R^{a2}$, $—S(O)_2NHR^{a1}$, $—S(O)_2NR^{a1}R^{a2}$, $—C(NH)NHR^{a1}$, $—C(NH)NR^{a1}R^{a2}$, $—NHC(O)R^{a1}$, $—NHC(S)R^{a1}$, $—NR^{a2}C(O)R^{a1}$, $—NR^{a1}C(S)R^{a2}$, $—NHS(O)_2R^{a1}$, —NR$^{a1}$S(O)$_2$R$^{a2}$, —NHC(O)NHR$^{a1}$, —NHC(S)NHR$^{a1}$, —NR$^{a1}$C(O)NH$_2$, —NR$^{a1}$C(S)NH$_2$, —NR$^{a1}$C(O)NHR$^{a2}$, —NR$^{a1}$C(S)NHR$^{a2}$, —NHC(O)NR$^{a1}$R$^{a2}$, —NHC(S)NR$^{a1}$R$^{a2}$, —NR$^{a1}$C(O)NR$^{a2}$R$^{a3}$, —NR$^{a3}$C(S)NR$^{a1}$R$^{a2}$, —NHS(O)$_2$NHR$^{a1}$, —NR$^{a1}$S(O)$_2$NH$_2$, —NR$^{a1}$S(O)$_2$NHR$^{a2}$, —NHS(O)$_2$NR$^{a1}$R$^{a2}$, —NR$^{a1}$S(O)$_2$NR$^{a2}$R$^{a3}$, —NHR$^{a1}$, and —NR$^{a1}$R$^{a2}$ in a number ranging from zero to (2n'+1), where n' is the total number of carbon atoms in such group. R$^{a1}$, R$^{a2}$ and R$^{a3}$ each independently refer to hydrogen, C$_{1-8}$ alkyl, heterocycloalkyl, aryl, heteroaryl, arylalkyl, heteroarylalkyl, aryl substituted with 1-3 halogens, C$_{1-8}$ alkoxy, haloalkyl, haloalkoxy or C$_{1-8}$ thioalkoxy groups, or unsubstituted aryl-C$_{1-4}$ alkyl groups. R$^{a1}$, R$^{a2}$ and R$^{a3}$ can be further substituted with R$^{b1}$, halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^{b1}$, —SR$^{b1}$, —OC(O)R$^{b1}$, —OC(S)R$^{b1}$, —C(O)R$^{b1}$, —C(S)R$^{b1}$, —C(O)OR$^{b1}$, —C(S)OR$^{b1}$, —S(O)R$^{b1}$, —S(O)$_2$R$^{b1}$, —C(O)NHR$^{b1}$, —C(S)NHR$^{b1}$, —C(O)NR$^{b1}$R$^{b2}$, —C(S)NR$^{b1}$R$^{b2}$, —S(O)$_2$NHR$^{b1}$, —S(O)$_2$NR$^{b1}$R$^{b2}$, —C(NH)NHR$^{b1}$, —C(NH)NR$^{b1}$R$^{b2}$, —NHC(O)R$^{b1}$, —NHC(S)R$^{b1}$, —NR$^{b2}$C(O)R$^{b1}$, —NR$^{b1}$C(S)R$^{b2}$, —NHS(O)$_2$R$^{b1}$, —NR$^{b1}$S(O)$_2$R$^{b2}$, —NHC(O)NHR$^{b1}$, —NHC(S)NHR$^{b1}$, —NR$^{b1}$C(O)NH$_2$, —NR$^{b1}$C(S)NH$_2$, —NR$^{b1}$C(O)NHR$^{b2}$, —NR$^{b1}$C(S)NHR$^{b2}$, —NHC(O)NR$^{b1}$R$^{b2}$, —NHC(S)NR$^{b1}$R$^{b2}$, —NR$^{b1}$C(O)NR$^{b2}$R$^{b3}$, —NR$^{b3}$C(S)NR$^{b1}$R$^{b2}$, —NHS(O)$_2$NHR$^{b1}$, —NR$^{b1}$S(O)$_2$NH$_2$, —NR$^{b1}$S(O)$_2$NHR$^{b2}$, —NHS(O)$_2$NR$^{b1}$R$^{b2}$, —NR$^{b1}$S(O)$_2$NR$^{b2}$R$^{b3}$, —NHR$^{b1}$, and —NR$^{b1}$R$^{b2}$ in a number ranging from zero to (2p'+1), where p' is the total number of carbon atoms in such group. R$^{b1}$, R$^{b2}$ and R$^{b3}$ each independently refer to hydrogen, C$_{1-8}$ alkyl, heterocycloalkyl, aryl, heteroaryl, arylalkyl, heteroarylalkyl, aryl substituted with 1-3 halogens, C$_{1-8}$ alkoxy, haloalkyl, haloalkoxy or C$_{1-8}$ thioalkoxy groups, or unsubstituted aryl-C$_{1-4}$ alkyl groups.

Substituents for the aryl and heteroaryl groups are varied and are generally selected from: R', halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR', —SR', —OC(O)R', —OC(S)R', —C(O)R', —C(S)R', —C(O)OR', —C(S)OR', —S(O)R', —S(O)$_2$R', —C(O)NHR', —C(S)NHR', —C(O)NR'R'', —C(S)NR'R'', —S(O)$_2$NHR', —S(O)$_2$NR'R'', —C(NH)NHR', —C(NH)NR'R'', —NHC(O)R', —NHC(S)R', —NR''C(O)R', —NR'C(S)R'', —NHS(O)$_2$R', —NR'S(O)$_2$R'', —NHC(O)NHR', —NHC(S)NHR', —NR'C(O)NH$_2$, —NR'C(S)NH$_2$, —NR'C(O)NHR'', —NR'C(S)NHR'', —NHC(O)NR'R'', —NHC(S)NR'R'', —NR'C(O)NR''R''', —NR'''C(S)NR'R'', —NHS(O)$_2$NHR', —NR'S(O)$_2$NH$_2$, —NR'S(O)$_2$NHR'', —NHS(O)$_2$NR'R'', —NR'S(O)$_2$NR''R''', —NHR', —NR'R'', —N$_3$, perfluoro(C$_1$-C$_4$)alkoxy, and perfluoro(C$_1$-C$_4$)alkyl, in a number ranging from zero to the total number of open valences on the aromatic ring system; and where R', R'' and R''' are independently selected from hydrogen, haloalkyl, haloalkoxy, C$_{1-8}$ alkyl, C$_{3-6}$ cycloalkyl, cycloalkylalkyl, C$_{2-8}$ alkenyl, C$_{2-8}$ alkynyl, aryl, arylalkyl, heteroaryl, heteroarylalkyl, aryl-C$_{1-4}$ alkyl, and aryloxy-C$_{1-4}$ alkyl. Other suitable substituents include each of the above aryl substituents attached to a ring atom by an alkylene tether of from 1-4 carbon atoms. R', R'' and R''' can be further substituted with R$^{a1}$, halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^{a1}$, —SR$^{a1}$, —OC(O)R$^{a1}$, —OC(S)R$^{a1}$, —C(O)R$^{a1}$, —C(S)R$^{a1}$, —C(O)OR$^{a1}$, —C(S)OR$^{a1}$, —S(O)R$^{a1}$, —S(O)$_2$R$^{a1}$, —C(O)NHR$^{a1}$, —C(S)NHR$^{a1}$, —C(O)NR$^{a1}$R$^{a2}$, —C(S)NR$^{a1}$R$^{a2}$, —S(O)$_2$NHR$^{a1}$, —S(O)$_2$NR$^{a1}$R$^{a2}$, —C(NH)NHR$^{a1}$, —C(NH)NR$^{a1}$R$^{a2}$, —NHC(O)R$^{a1}$, —NHC(S)R$^{a1}$, —NR$^{a2}$C(O)R$^{a1}$, —NR$^{a1}$C(S)R$^{a2}$, —NHS(O)$_2$R$^{a1}$, —NR$^{a1}$S(O)$_2$R$^{a2}$, —NHC(O)NHR$^{a1}$, —NHC(S)NHR$^{a1}$, —NR$^{a1}$C(O)NH$_2$, —NR$^{a1}$C(S)NH$_2$, —NR$^{a1}$C(O)NHR$^{a2}$, —NR$^{a1}$C(S)NHR$^{a2}$, —NHC(O)NR$^{a1}$R$^{a2}$, —NHC(S)NR$^{a1}$R$^{a2}$, —NR$^{a1}$C(O)NR$^{a2}$R$^{a3}$, —NR$^{a3}$C(S)NR$^{a1}$R$^{a2}$, —NHS(O)$_2$NHR$^{a1}$, —NR$^{a1}$S(O)$_2$NH$_2$, —NR$^{a1}$S(O)$_2$NHR$^{a2}$, —NHS(O)$_2$NR$^{a1}$R$^{a2}$, —NR$^{a1}$S(O)$_2$NR$^{a2}$R$^{a3}$, —NHR$^{a1}$, —NR$^{a1}$R$^{a2}$, —N$_3$, perfluoro(C$_1$-C$_4$)alkoxy, and perfluoro(C$_1$-C$_4$)alkyl, in a number ranging from zero to the total number of open valences on the aromatic ring system; and where R$^{a1}$, R$^{a2}$ and R$^{a3}$ are each independently selected from hydrogen, haloalkyl, haloalkoxy, C$_{1-8}$ alkyl, C$_{3-6}$ cycloalkyl, cycloalkylalkyl, C$_{2-8}$ alkenyl, C$_{2-8}$ alkynyl, aryl, arylalkyl, heteroaryl, heteroarylalkyl, aryl-C$_{1-4}$ alkyl, or aryloxy-C$_{1-4}$ alkyl. Other suitable substituents include each of the above aryl substituents attached to a ring atom by an alkylene tether of from 1-4 carbon atoms.

When two substituents are present on adjacent atoms of a substituted aryl or a substituted heteroaryl ring, such substituents may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, when two substituents are present on adjacent atoms of a substituted aryl or a substituted heteroaryl ring, such substituents may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, when two substituents are present on adjacent atoms of a substituted aryl or a substituted heteroaryl ring, such substituents may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

"Protecting group" refers to a grouping of atoms that when attached to a reactive group in a molecule masks, reduces or prevents that reactivity. Examples of protecting groups can be found in T.W. Greene and P.G. Wuts, PROTECTIVE GROUPS IN ORGANIC CHEMISTRY, (Wiley, 4th ed. 2006), Beaucage and Iyer, Tetrahedron 48:2223-2311 (1992), and Harrison and Harrison et al., COMPENDIUM OF SYNTHETIC ORGANIC METHODS, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), tri-isopropylsilyl (TIPS), phenylsulphonyl and the like (see also, Boyle, A. L. (Editor), carbamates, amides, N-sulfonyl derivatives, groups of formula —C(O)OR, wherein R is, for example, methyl, ethyl, t-butyl, benzyl, phenylethyl, CH$_2$=CHCH$_2$—, and the like, groups of the formula —C(O)R', wherein R' is, for example, methyl, phenyl, trifluoromethyl, and the like, groups of the formula —SO$_2$R'', wherein R'' is, for example, tolyl, phenyl, trifluoromethyl, 2,2,5,7,8-pentamethylchroman-6-yl, 2,3,6-trimethyl-4-methoxyphenyl, and the like, and silanyl containing groups, such as 2-trimethylsilylethoxymethyl, t-butyldimethylsilyl, triisopropylsilyl, and the like, CURRENT PROTOCOLS IN NUCLEIC ACID CHEMISTRY, John Wiley and Sons, New York, Volume 1, 2000).

The term "Labile protecting group" refers to those protecting groups that are removable under mild conditions that do not significantly impact other protecting groups or the remainder of the molecule.

The term "Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

Compounds

In one aspect, the present invention provides a compound of formula (I):

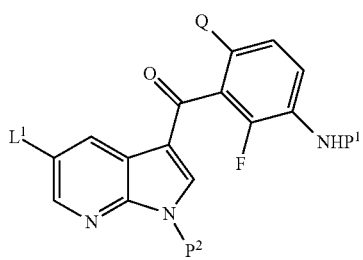

(I)

wherein the substituents $P^1$, $P^2$, $L^1$ and Q are as defined in the Summary of the Invention. In one embodiment, $P^1$ is H. The compounds of formula (I) are useful intermediates for the synthesis of various biologically active molecules, for example, compounds of formula (III):

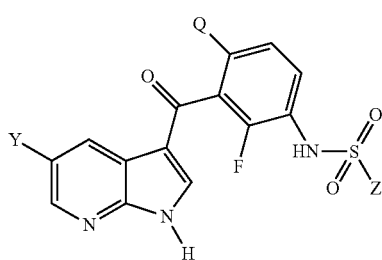

(III)

wherein Y is optionally substituted aryl or optionally substituted heteroaryl; Z is optionally substituted $C_{1-6}$alkyl, optionally substituted alkylamino, optionally substituted dialkylamino, optionally substituted cycloalkylamino, optionally substituted arylamino, optionally substituted heteroarylamino or $NH_2$. Q is H or F. In one embodiment, Q is F.

In certain embodiments of compounds of formula (I), $P^1$ can be selectively removed in the presence of the $P^2$ group. Selective cleavage of $P^1$ can be accomplished by adjusting the reaction conditions, such as temperature, pH, reaction time and so forth. In some embodiments, $P^1$ is a labile amino protecting group. Exemplary labile protecting group includes 9-fluorenylmethoxycarbonyl, t-butoxycarbonyl, trimethylsilyl or t-butyldiphenylsilyl. In a preferred embodiment, $P^1$ is H.

In certain embodiments of compounds of formula (I), $P^2$ is an amino protecting group, which is capable of forming a carbamate or an amide linkage with the amino group to which it is attached. In some embodiments, $P^2$ is an amino protecting group selected from $R^3$—C(O)— or $R^4$O—C(O)—, wherein $R^3$ and $R^4$ are each independently selected from $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted. In certain instances, $R^3$ and $R^4$ are each independently selected from $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted with 1-3 $R^a$ groups independently selected from halogen, $C_{1-6}$alkyl, $C_{1-6}$haloalkyl, $C_{1-6}$haloalkoxy, fluoro substituted $C_{1-6}$alkyl, fluoro substituted $C_{1-6}$alkoxy, aryl, heteroaryl, $C_{1-6}$alkoxy, —CN, —$NO_2$, —OH, $C_{1-6}$alkyl-OC(O)—, $C_{1-6}$alkyl-C(O)O— or —$SiMe_3$, wherein the aliphatic or aromatic portion of $R^a$ is further optionally substituted with from 1-3 $R^b$ groups independently selected from halogen, $C_{1-6}$alkyl, $C_{1-6}$alkoxy, —CN, —$NO_2$ or —OH. In other instances, $R^3$ and $R^4$ are each independently methyl, ethyl, phenyl, 2,2,2-trichloroethyl, $(CH_3)_2$CHC≡C—, 2-trimethylsilylethyl, 1-methyl-1-phenylethyl, cyclobutyl, cyclopropyl, allyl, vinyl, 1-adamantyl, benzyl or diphenylmethyl, each of which is optionally substituted with from 1-3 $R^a$ groups. In some embodiments, $R^a$ is F, Cl, Br, I, —$CH_3$, Phenyl, t-butyl, MeO—, —$NO_2$, —CN, —$CF_3$, $CF_3$O—, —OH or —CH═$CH_2$. In one embodiment, $P^2$ is 2,6-dichlorophenylcarbonyl. In another embodiment, $P^2$ is 2,5-dichlorophenylcarbonyl, 2,3-dichlorophenylcarbonyl or 2,4-dichlorophenylcarbonyl. In certain embodiments, $P^2$ is phenylcarbonyl optionally substituted with from 1-2 groups independently selected from F, Cl, Br, CN or $NO_2$. In some embodiments of compounds of formula (I), $P^2$ is H. All the other variables $L^1$, $P^1$ and Q are as defined in any of the embodiments described herein.

In some embodiments of compounds of formula (I), $L^1$ is Br, Cl, I, tosyl-O—, mesyl-O—, trifluoromethanesulfonyl-O—, $R^1$—$SO_2$O— or $R^2$C(O)O, wherein $R^1$ and $R^2$ are each independently selected from aryl, aryl-$C_{1-4}$alkyl or $C_{1-6}$alkyl, each of which is optionally substituted with from 1-3 $R^c$ substituents selected from halogen, —CH═$CH_2$, —CN, —OH, —$NH_2$, —$NO_2$, —C(O)OH, —C(O)$NH_2$, —S(O)$_2$$NH_2$, —NHC(O)$NH_2$, —NHC(S)$NH_2$, —NHS(O)$_2$$NH_2$, —C(NH)$NH_2$, —$OR^d$, —$SR^d$, —OC(O)$R^d$, —C(O)$R^d$, —C(O)$OR^d$, —C(S)$OR^d$, —S(O)$R^d$, —S(O)$_2$$R^d$, —C(O)$NHR^d$, —C(O)$NR^dR^d$, —S(O)$_2$$NHR^d$, —S(O)$_2$$NR^dR^d$, —C(NH)$NHR^d$, —C(NH)$NR^dR^d$, —NHC(O)$R^d$, —$NR^d$C(O)$R^d$, —NHS(O)$_2$$R^d$, —$NR^d$S(O)$_2$$R^d$, —NHC(O)$NHR^d$, —$NHR^d$ or —$NR^dR^d$, wherein each $R^d$ is independently selected from $C_{1-6}$alkyl or aryl. In some instances, $R^d$ is —$CH_3$, ethyl or phenyl. In some embodiments, $L^1$ is Br, Cl, I, tosyl-O—, mesyl-O—, trifluoromethanesulfonyl-O—, $CF_3$C(O)O— or $CH_3$C(O)O—. In one embodiment, $L^1$ is Br or Cl. All the other variables, $P^1$, $P^2$ and Q are as defined in any of the embodiments described herein.

In one embodiment of compounds of formula (I), $P^1$ is H; and Q is F. In another embodiment, $P^1$ and Q are H. In yet another embodiment, $P^1$ is H; $L^1$ is Br or Cl; and Q is F. In a preferred embodiment of compounds of formula (I), $L^1$ is Br or Cl; $P^1$ is H; and $P^2$ is 2,6-dichlorophenylcarbonyl.

Methods

In another aspect, the present invention provide a method for preparing a compound of formulas (I) and (Ia). The method comprises contacting/reacting a compound of formula (II):

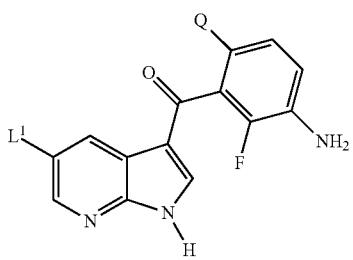

(II)

with an agent of the formula: $P^2$—$X^1$ under conditions sufficient to form the compound of formula (Ia):

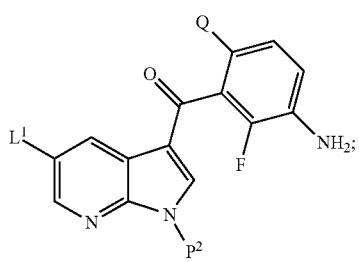

(Ia)

and
contacting/reacting a compound of formula (Ia) with an agent of the formula: $P^1$—$X^3$ under conditions sufficient to form the compound of formula (I). Alternatively, compound of formula (I) can also be prepared by first reacting a compound of formula (II) with an agent of the formula: $P^1$—$X^3$ to form an intermediate product, followed by reacting the intermediate product with an agent of the formula: $P^2$—$X^1$. $X^1$ is selected from Br, Cl, I, tosyl-O—, mesyl-O—, trifluoromethanesulfonyl-O—, $CF_3C(O)O$— or $CH_3C(O)O$—. $X^3$ is a leaving group. In one embodiment, $X^3$ is Cl, Br, I, tosyl-O—, mesyl-O, $CF_3S(O)_2O$—, $CF_3C(O)O$— or $CH_3C(O)O$—. $P^1$ is a labile protecting group. In one embodiment, $P^1$ is 9-fluorenylmethoxycarbonyl, t-butoxycarbonyl, trimethylsilyl or t-butyldiphenylsilyl. In one embodiment, $P^2$ is H. In another embodiment, $P^2$ is an amino protecting group as found in T.W. Greene and P.G. Wuts, PROTECTIVE GROUPS IN ORGANIC CHEMISTRY, (Wiley, 4th ed. 2006) or as defined in any of the embodiments described herein. Q is H or F. $L^1$ is Br, Cl, I, $R^1$—$SO_2O$— or $R^2C(O)O$, wherein $R^1$ and $R^2$ are each independently optionally substituted aryl or optionally substituted $C_{1-6}$alkyl. In some embodiments, $R^1$ and $R^2$ are each independently selected from aryl, aryl-$C_{1-4}$alkyl or $C_{1-6}$alkyl, each of which is optionally substituted with from 1-3 $R^c$ substituents, wherein each $R^d$ is independently selected from $C_{1-6}$alkyl or aryl. In some instances, $R^d$ is $CH_3$, ethyl or phenyl. In some embodiments, $L^1$ is Br, Cl, I, tosyl-O—, mesyl-O—, trifluoromethanesulfonyl-O—, $CF_3C(O)O$— or $CH_3C(O)O$—. In a preferred embodiment, $L^1$ is Br or Cl.

In some embodiments, the reactions for preparing compounds of formulas (I) or (Ia) can be carried out in the presence of a base dissolved in an organic solvent. Some preferred bases include dimethylaminopyridine (DMAP), triethylamine (TEA), N,N-diisopropylethylamine (DIPEA) and combinations thereof. DMAP is generally present in a catalytic amount of about 0.05, 0.07, 0.08, 0.1, 0.2, 0.3, 0.4 or 0.5 equivalents. TEA or DIPEA can range from about 1-5 equivalents, for example, 1.0, 2.0, 3.0, 4.0 or 5.0 equivalents. The organic solvents used include, but are not limiting to, tetrahydrofuran (THF), 2-methyl-THF, acetonitrile, dichloromethane and benzene. A preferred solvent is 2-methyl-THF. The solvents can be present in various volumes, e.g., 0.5, 1, 2, 3, 4, 5, 6, 7, 8, 9, 10, 11, 12, 13, 14, or 12 volumes.

Compounds of formula (II) can be prepared by contacting a compound of formula (V):

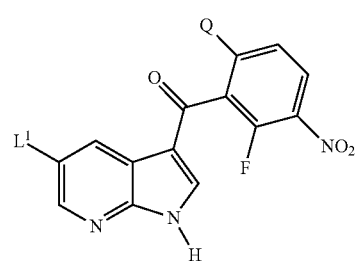

(V)

with a reducing agent under conditions sufficient to form the compounds of formula (II). The variables, $L^1$ and Q are as defined in any of the embodiments described herein. In one embodiment, $L^1$ is Br and Q is F. The reducing agent may be, but is not limited to, tin chloride dihydrate ($SnCl_2.2H_2O$). Typically, 1-5 equivalents (e.g., 1, 2, 3, 4 or 5 eqs) of the reducing agent are used. The reaction can be carried out at a temperature of about 40-90° C., preferably about 50-70° C., more preferably about 60° C. The solvents for the reaction can be 2-methyl-THF or a mixture of 1:1 ethyl acetate/THF. The volumes of the solvents can be from about 5 to 100 or about 7 to 80. In one embodiment, a compound of formula (V) is treated with 3 or 4 equivalents of $SnCl_2$ in 80 volumes of 1;1 ethyl acetate/THF or 7 volumes of 2-methyl THF at 60° C.

Compounds of formula (V) can be prepared by reacting a compound of formula (VI):

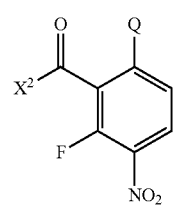

(VI)

with a compound of formula (VII):

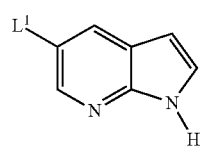

(VII)

in the presence of a metal halide, such as $AlCl_3$ under conditions sufficient to form the compounds of formula (V). $X^2$ is selected from Br, Cl, I, tosyl-O—, mesyl-O—, trifluoromethanesulfonyl-O—, $CF_3C(O)O$— or $CH_3C(O)O$—. The variables, $L^1$ and Q are as defined in any of the embodiments described herein. In a preferred embodiment, $X^2$ is Br or Cl. In one embodiment, Q is F, $L^1$ is Br and $X^2$ is Cl. The solvents used in the reaction include, but are not limited to, $CH_3NO_2$, acetonitrile, dichloromethane, dichloroethane, benzene, toluene and combinations thereof. In one embodiment, the solvent is dichloroethane.

In another aspect, the present invention provides a method for preparing a compound of formula (III):

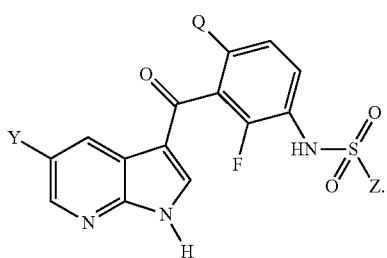

(III)

In one embodiment, the method comprises coupling, sulfonylation and deprotection steps. For example, the method comprises:
(i) contacting a compound of formulas (I) or (Ia) with an agent of the formula: $Y-B(OR^5)_2$ (i.e., formula IVb) or the formula: $Y-Sn(Bu)_3$ (i.e., formula IVc) and a palladium or a nickel complex under conditions sufficient to form a compound of formula (IV):

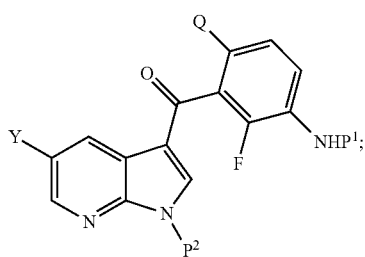

(IV)

(ii) reacting a compound of formula (IV) with an agent of the formula: $A^1-S(O)_2-Z$ (i.e., formula IVa) under conditions sufficient to form a compound of formula (IX):

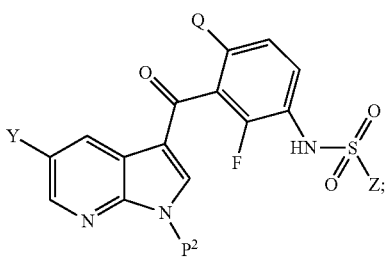

(IX)

and
(iii) removing the protecting group $P^2$ under conditions sufficient to form the compound of formula (III).

Alternatively, the compounds of formula (III) can be prepared by carrying out sulfonylation reaction first, followed by Suzuki coupling and removing of the protecting group $P^2$. For example, the method comprises:

(i) contacting a compound of formula (I) with an agent of the formula: $A^1-S(O)_2-Z$ (i.e., formula IVa) under conditions sufficient to form a compound of formula (VIII):

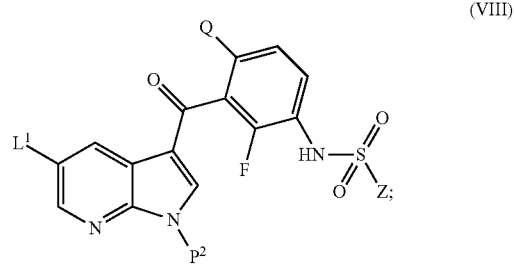

(VIII)

(ii) reacting a compound of formula (VIII) with an agent of the formula (IVb): $Y-B(OR^5)_2$ or formula (IVc): $Y-Sn(Bu)_3$ and a palladium or a nickel complex under conditions sufficient to form a compound of formula (IX); and
(iii) removing the protecting group $P^2$ under conditions sufficient to form the compound of formula (III), wherein:
Q is H or F;
$P^1$ and $P^2$ are as defined in any of the embodiments as described herein;
$R^5$ is $-OH$, $C_{1-6}$alkyl or two $-OR^5$ substituents together with the boron atom to which they are attached form an optionally substituted 5 or 6-membered ring;
$A^1$ is a leaving group;
Y is optionally substituted aryl or optionally substituted heteroaryl; and
Z is $-N(R^6)(R^7)$ or $-C(R^8)(R^9)(R^{10})$; wherein:
$R^6$ and $R^7$ are each independently selected from the group consisting of H, optionally substituted $C_{1-6}$alkyl, optionally substituted $C_{3-8}$cycloalkyl, optionally substituted $C_{3-8}$cycloalkylalkyl, optionally substituted heterocycloalkyl, optionally substituted heterocycloalkylalkyl, optionally substituted aryl, optionally substituted arylalkyl, optionally substituted heteroaryl and optionally substituted heteroarylalkyl; or $R^6$ and $R^7$ taken together with the nitrogen atom to which they are attached form a four to eight-membered ring having from 0-2 additional heteroatoms as ring members selected from N, O or S, wherein the four to eight-membered ring is optionally substituted; and
$R^8$, $R^9$ and $R^{10}$ are each independently H, optionally substituted $C_{1-6}$alkyl, optionally substituted, $C_{1-6}$haloalkyl, optionally substituted $C_{1-6}$haloalkoxy, optionally substituted $C_{3-8}$cycloalkyl, optionally substituted $C_{3-8}$cycloalkylalkyl, optionally substituted aryl, optionally substituted arylalkyl, optionally substituted heterocycloalkyl, optionally substituted heterocycloalkylalkyl, optionally substituted heteroaryl, optionally substituted heteroarylalkyl or $-X^2R^{11}$, wherein $X^2$ is $-NR^{12}$, O or S; $R^{12}$ is H, $C_{1-6}$alkyl or aryl; and $R^{11}$ is H, $C_{1-6}$alkyl, $C_{1-6}$haloalkyl, $C_{1-6}$haloalkoxy, $C_{3-8}$cycloalkyl, $C_{3-8}$cycloalkylalkyl, aryl, arylalkyl, heteroaryl or heteroarylalkyl, wherein $R^{11}$ is optionally substituted with from 1 to 3 $R^e$ substituents selected from halogen, $-CN$, $-CH=CH_2$, $-OH$, $-NH_2$, $-NO_2$, $-C(O)OH$, $-C(S)OH$, $-C(O)NH_2$, $-C(S)NH_2$, $-S(O)_2NH_2$, $-NHC(O)NH_2$, $-NHC(S)NH_2$, $-NHS(O)_2NH_2$, $-C(NH)NH_2$, $-OR^f$, $-SR^f$, $-OC(O)R^f$, $-OC(S)R^f$, $-C(O)R^f$, $-C(S)$ $R^f$, —C(O)O$R^f$, —C(S)O$R^f$, —S(O)$R^f$, —S(O)$_2R^f$, —C(O)NH$R^f$, —C(S)NH$R^f$, —C(O)N$R^fR^f$, —C(S)N$R^fR^f$, —S(O)$_2$NH$R^f$, —S(O)$_2$N$R^fR^f$, —C(NH)NH$R^f$, —C(NH)N$R^fR^f$, —NHC(O)$R^f$, —NHC(S)$R^f$, —N$R^f$C(O)$R^f$, —N$R^f$C(S)$R^f$, —NHS(O)$_2R^f$, —N$R^f$S(O)$_2R^f$, —NHC(O)NH$R^f$, —NHC(S)NH$R^f$, —N$R^f$C(O)NH$R^f$, —N$R^f$C(S)NH$R^f$, —N$R^f$C(O)NH$_2$, —N$R^f$C(S)NH$_2$, —N$R^f$C(O)NH$R^f$, —N$R^f$C(S)NH$R^f$, —NHC(O)N$R^fR^f$, —NHC(S)N$R^fR^f$, —N$R^f$C(O)N$R^fR^f$, —N$R^f$C(S)N$R^fR^f$, —NHS(O)$_2$NH$R^f$, —N$R^f$S(O)$_2$NH$_2$, —N$R^f$S(O)$_2$NH$R^f$, —NHS(O)$_2$N$R^fR^f$, —N$R^f$S(O)$_2$N$R^fR^f$, —NH$R^f$, —N$R^fR^f$ and $R^f$, wherein $R^f$ is $C_{1-6}$alkyl, $C_{3-6}$cycloalkyl, heterocycloalkyl, heteroaryl or aryl, wherein $R^f$ is optionally substituted with from 1-3 $R^g$ substituents selected from —CN, —CH=CH$_2$, —OH, —NH$_2$, —NO$_2$, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —O$R^h$, —S$R^h$, —OC(O)$R^h$, —OC(S)$R^h$, —C(O)$R^h$, —C(S)$R^h$, —C(O)O$R^h$, —C(S)O$R^h$, —S(O)$R^h$, —S(O)$_2R^h$, —C(O)NH$R^h$ or $R^h$, wherein $R^h$ is $C_{1-6}$alkyl; or any two of the $R^8$, $R^9$ and $R^{10}$ groups taken together with the carbon atom to which they are attached form a 3 to 8-membered optionally substituted non-aromatic ring having from 0 to 2 heteroatoms selected from N, O or S. In some instances, at each occurrence, at least two of the $R^8$, $R^9$ and $R^{10}$ groups are not simultaneously hydrogen. In one embodiment, Q is F. In another embodiment, Q is H. In yet another embodiment, Y is 4-chlorophenyl; Z is propyl; Q is F; $R^5$ is —OH; $P^1$ is H; and $P^2$ is 2,6-dichlorophenylcarbonyl.

The agents Y—B(O$R^5$)$_2$ (i.e., formula IVb) or Y—Sn(Bu)$_3$ (i.e., formula IVc) are either commercially available or can be readily prepared in accordance with the procedures described in the literature. In some embodiments, —B(O$R^5$)$_2$ is:

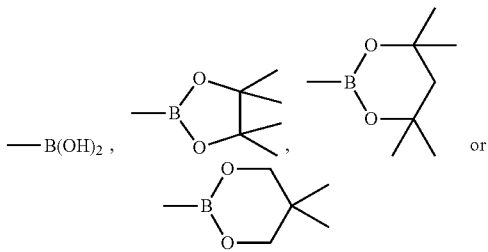

In one embodiment, Y—B(O$R^5$)$_2$ is Y—B(OH)$_2$. Y is as defined in any of the embodiments as described herein.

The agent $A^1$-S(O)$_2$—Z (i.e., formula IVa) is either commercially available or can be readily prepared in accordance with the procedures described in the literature. The leaving group $A^1$ can be Cl, Br, I, tosyl-O—, mesyl-O, CF$_3$S(O)$_2$O—, CF$_3$C(O)O— or CH$_3$C(O)O—. In one embodiment, $A^1$ is Cl.

In some embodiments of compounds of formula (III), Y is selected from phenyl, 2-pyridyl, 3-pyridyl, 4-pyridyl, 2-pyrazinyl, 3-pyridazinyl, 4-pyridazinyl, 2-pyrimidinyl, 4-pyrimidinyl, 5-pyrimidinyl, 1-pyrrolyl, 2-pyrrolyl, 3-pyrrolyl, 2-imidazolyl, 4-imidazolyl, 1-pyrazolyl, 2-pyrazolyl, 3-pyrazolyl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl or 5-isothiazolyl, each of which is optionally substituted with from 1-3 $R^e$ groups; or 1-3 $R^f$ groups; or 1-3 $R^g$ groups; or 1-3 $R^h$ groups. In certain instances, $R^e$ is F, Cl, Br, I, —CN, —OH, —CF$_3$, NH$_2$, CF$_3$O—, CH$_3$—, ethyl, CH$_3$O, EtO—, —NO$_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, 1-cyclopropylethyl, 2-cyclopropylethyl, 1-cyclopropylethylamino, 2-cyclopropylethylamino, 1-hydroxy-1-methylethyl, methylcarbamoyl, 1-carboxycyclopropyl, 1-carbamoylcyclopropyl, 1-methoxycarbonylcyclopropyl, 1-cyanoisopropyl, 1-hydroxycyclopropyl, 1-hydoxyisopropyl, cyclobutoxy, cyclopentoxy, cyclohexyloxy, 4-morpholino, 4-hydroxypiperidinyl, 1-piperidinyl, piperazinyl, 4-methylpiperazinyl, 4-t-butoxycarbonylpiperazinyl, azetidinyl, pyrrolidinyl, cyclopropylcarbamoyl, 5-methyl-1,2,4-oxadiazol-3-yl, 5-methyl-1,3,4-oxadiazol-2yl, 5-dimethylamino-1,3,4-oxadiazol-2yl or 5-methylamino-1,3,4-thiadiazol-2-yl. The other variables Q and Z are as defined in any of the embodiments as described herein.

In some embodiments of compounds of formula (III), Y is phenyl, 1-naphthyl or 2-naphthyl, each of which is optionally substituted with from 1-3 substituents selected from F, Cl, Br, I, —CN, —OH, —CF$_3$, NH$_2$, CF$_3$O—, CH$_3$—, CH$_3$O, —NO$_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, 1-cyclopropylethyl, 2-cyclopropylethyl, 1-cyclopropylethylamino, 2-cyclopropylethylamino or 1-hydroxy-1-methylethyl or methylcarbamoyl. The other variables Q and Z are as defined in any of the embodiments as described herein.

In some embodiments of compounds of formula (III), Y is selected from 4-pyrimidinyl, 5-pyrimidinyl, 2-pyrazinyl, 2-thiazolyl, 4-thiazolyl, 5-thiazolyl, 2-thiophenyl, 3-thiophenyl, 2-amino-quinazolin-5-yl, 2-amino-quinazolin-6-yl, 2-amino-quinazolin-6-yl, 2-amino-quinazolin-7-yl, 2-amino-quinazolin-8-yl, 2-oxo-6-indolinyl, 2-oxo-4-indolinyl, 2-oxo-5-indolinyl, 2-oxo-7-indolinyl, 2-pyridyl, 3-pyridyl, 4-pyridyl, 1H-indazol-4-yl, 1H-indazol-5-yl, 1H-indazol-6-yl or 1H-indazol-7-yl, each of which is substituted with from 1 to 2 substituents independently selected from F, Cl, Br, I, —CN, —OH, —CF$_3$, NH$_2$, CF$_3$O—, CH$_3$—, CH$_3$O, C$_2$H$_5$O—, —NO$_2$, cyclopropyl, cyclopropylmethyl, cyclopropylamino, cyclopropylmethylamino, 1-cyanocyclopropyl, 1-carboxycyclopropyl, 1-carbamoylcyclopropyl, 1-methoxycarbonylcyclopropyl, 1-cyanoisopropyl, 1-hydroxycyclopropyl, 1-hydoxyisopropyl, cyclobutoxy, cyclopentoxy, cyclohexyloxy, 4-morpholino, 4-hydroxypiperidinyl, 1-piperidinyl, piperazinyl, 4-methylpiperazinyl, 4-t-butoxycarbonylpiperazinyl, azetidinyl, pyrrolidinyl, cyclopropylcarbamoyl, 5-methyl-1,2,4-oxadiazol-3-yl, 5-methyl-1,3,4-oxadiazol-2yl, 5-dimethylamino-1,3,4-oxadiazol-2yl, 5-methylamino-1,3,4-thiadiazol-2-yl, methylamino, dimethylamino, methylthio, acetoxy, acetyl, methoxycarbonyl, acetamido, methylcarbamoyl, isopropyl, 1-pyrrolidinyl, 1-cyclopropylethyl, 2-cyclopropylethyl, 1-cyclopropylethylamino, 2-cyclopropylethylamino or 1-hydroxy-1-methylethyl. In certain instances, Y is 4-chlorophenyl. In other instances, Y is 4-pyrimidinyl or 5-pyrimidinyl, each of which optionally substituted with from 1, 2, or 3 substituents independently selected from F, Cl, Br, I, —CN, —OH, —CF$_3$, NH$_2$, CF$_3$O—, CH$_3$—, CH$_3$O, —NO$_2$, cyclopropyl, 1-cyanocyclopropyl, cyclopropylmethyl, cyclopropylamino, cyclopropylmethylamino, methylamino, dimethylamino, methylthio, acetoxy, acetyl, methoxycarbonyl, acetamido, methylcarbamoyl, isopropyl, 1-pyrrolidinyl, 1-cyclopropylethyl, 2-cyclopropylethyl, 1-cyclopropylethylamino, 2-cyclopropylethylamino or 1-hydroxy-1-methylethyl. The other variables Q and Z are as defined in any of the embodiments as described herein.

In some embodiments of compounds of formula (III), Z is 1-azetindinyl, 1-pyrrolidinyl, 1-piperidinyl, 4-morpholinyl, 4-thiomorpholinyl, 3-oxazolidinyl, 3-thiazolidinyl, 2-isoxazolidinyl, 2-isothiazolidinyl, 1-pyrazolidinyl, 1-piperazinyl, 1-hexahydropyrimidinyl or 1-hexahydropyridazinyl, each of which is optionally substituted with from 1-3 $R^e$ groups. In certain instances, $R^e$ is F, $CH_3$, methoxycarbonyl, ethoxycarbonyl, —$CH_3$, $CH_3(CO)NH$—, vinyl, propen-3-yl or $CH_3(CO)(CH_3)N$—. The other variables Q and Y are as defined in any of the embodiments as described herein.

In some embodiments of compounds of formula (III), Z is selected from 1-azetindinyl, 1-pyrrolidinyl, 1-piperidinyl, 4-morpholinyl, 4-thiomorpholinyl, 3-oxazolidinyl, 3-thiazolidinyl, 2-isoxazolidinyl, 2-isothiazolidinyl, 1-pyrazolidinyl, 1-piperazinyl, 1-hexahydropyrimidinyl or 1-hexahydropyridazinyl, each of which is optionally substituted with from 1-2 $R^i$ substituents selected from F, Cl, Br, I, —CN, —OH, —$CF_3$, $NH_2$, $CF_3O$—, $CH_3$—, $CH_3O$, —$NO_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. In certain instances, $R^i$ is F, $CH_3$, methoxycarbonyl, ethoxycarbonyl, —$CH_3$, $CH_3(CO)NH$—, vinyl, propen-3-yl or $CH_3(CO)(CH_3)N$—. The other variables Q and Y are as defined in any of the embodiments as described herein.

In some embodiments of compounds of formula (III), Z is $C_{1-6}$alkyl, cyclopropyl, cyclobutyl, cyclohexyl, cyclopentyl, cycloheptyl or cyclooctyl, each of which is optionally substituted with from 1-3 RJ groups selected from F, —CN, —OH, —$CF_3$, $NH_2$, $CF_3O$—, $CH_3$—, $CH_3O$, —$NO_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. In one embodiment, Z is propyl. The other variables Q and Y are defined in any of the embodiments as described herein.

In some embodiments of compounds of formula (III), Z is selected from the group consisting of cyclopropyl, cyclobutyl, cyclohexyl, cyclopentyl, cycloheptyl, cyclooctyl, 1-azetindinyl, 1-pyrrolidinyl, 1-piperidinyl, 4-morpholinyl, 4-thiomorpholinyl 3-oxazolidinyl, 3-thiazolidinyl, 2-isoxazolidinyl, 2-isothiazolidinyl, 1-pyrazolidinyl, 1-piperazinyl, 1-hexahydropyrimidinyl, 1-hexahydropyridazinyl, $(CH_3)(CF_3CH_2)N$—, cycloproylmethylamino, sec-butyl, pentan-2-yl and pentan-3-yl, each of which is optionally substituted with from 1-2 $R^k$ groups selected from F, Cl, Br, I, —CN, —OH, —$CF_3$, $NH_2$, $CF_3O$—, $CH_3$—, $CH_3O$, —$NO_2$, cyclopropyl, cyclopropylmethyl, cyclopropylamino, cyclopropylmethylamino, 1-cyanocyclopropyl, methylamino, dimethylamino, methylthio, acetoxy, acetyl, methoxycarbonyl, acetamido, methylcarbamoyl, 2-pyridyl, 3-pyridyl, 4-pyridyl, 2-pyridylmethyl, 3-pyridylmethyl, 4-pyridylmethyl, 2-oxetanyl, 3-oxetanyl, 2-oxetanylmethyl, 3-oxetanylmethyl, 2-tetrahydrofuranyl, 3-tetrahydrofuranyl, 2-tetrahydrofuranylmethyl, 3-tetrahydrofuranylmethyl, 1-pyrrolidinyl, 2-pyrrolidinyl, 3-pyrrolidinyl, 2-tetrahydrothiophenyl, 3-tetrahydrothiophenyl, 4-morpholinyl, 2-morpholinyl or 3-morpholinyl. In one instance, $R^k$ is —F, methoxycarbonyl, ethoxycarbonyl, —$CH_3$, $CH_3(CO)NH$—, vinyl, propen-3-yl or $CH_3(CO)(CH_3)N$—. In another instance, $R^k$ is —F, methoxycarbonyl, ethoxycarbonyl, —$CH_3$, $CH_3(CO)NH$— or $CH_3(CO)(CH_3)N$—. In yet another instance, $R^k$ is vinyl or propen-3-yl. The other variables Q and Y are as defined in any of the embodiments as described herein.

Various palladium or nickel complexes can be used for the preparation of compounds of formula (III). Preferably, palladium phosphine complexes are used in the reaction. The palladium complexes include, but are not limited to, $Pd(PPh_3)_4$, $PdCl_2(PPh_3)_2$, bis[1,2-bis(diphenylphosphino)ethane]palladium, bis(tri-t-butylphosphine)palladium, diacetobis(triphenylphosphine)palladium, tris(dibenzylideneacetone)dipalladium ($Pd_2(dba)2$), $Pd(OAc)_2$, dichloro[1,1'-bis(diphenylphosphino)ferrocene]palladium(II), and dichloro [1,1'-bis(di-i-propyl-phosphino)ferrocene]palladium (II). In one embodiment, the palladium complex is $PdCl_2(PPh_3)_2$. The palladium complexes can be present between 0.01 and 0.1 equivalents, e.g., about 0.01, 0.02, 0.025, 0.03, 0.04, 0.05, 0.06, 0.07, 0.08, 0.09 or 0.1 equivalents. Exemplary nickel complexes include, but are not limited to, $NiCl_2$ (dppf), bis(tricyclohexylphosphine) nickel(II) chloride ($NiCl_2(PCy_3)_2$) and $NiCl_2(PPh_3)_2$.

The Suzuki coupling reaction can be carried out in various solvents, including, but not limiting to, toluene, dioxane, THF, 2-methyl-THF, water or a mixture thereof. In one embodiment, the reaction is carried out in dioxane or 2-methyl-THF. The reaction can be performed at a temperature between 50-100° C., 60-90° C. or 70-85° C. In one embodiment, the reaction is carried out using 0.025-0.05 eq of $PdCl_2(PPh_3)_2$, 2-3 eq of $K_2CO_3$ or $NaHCO_3$, 1 eq of compound of formula (I), 1.5-2 eq of compound of formula (IVb), 10 volumes of dioxane and 5 volumes of water.

The sulfonylation reaction can be carried out in various solvents including, but not limiting to, pyridine, dichloromethane, THF, acetonitrile, toluene, dioxane, 2-methyl-THF or a mixture thereof. Excess solvents can be used during the reaction, for example, the solvents can be from 1-5 equivalents, such as 1, 1.5, 2, 2.5, 3, or 4 equivalents. The temperature for the reaction can be maintained from about 50-110° C., e.g., 50, 55, 60, 65, 70, 80, 85, 90, 95, 100, 105 or 110° C. In one embodiment, the reaction is carried out in a mixed solvents of pyridine and 10 volumes of dioxane at about 100° C.

The deprotection reaction can be conducted by reacting a compound of formula (IX) with $NH_3$ dissolved in an organic solvent at a temperature from about 50-110° C., e.g., 50, 55, 60, 65, 70, 80, 85, 90, 95, 100, 105 or 110° C. The solvents used include, but are not limited to, methanol (MeOH), ethanol (EtOH), dimethylformamide (DMF), dimethylacetamide (DMA), THF, dimethylsulfoxide (DMSO), dioxane, isopropanol (IPA) or combinations thereof. In one embodiment, the reaction can be conducted at 55° C. in the presence of $NH_3$ (5 eq), MeOH (5 eq, 10 volumes) and DMA (5 volumes). In another embodiment, the reaction can be conducted at 100° C. in the presence of THF (5 volumes) and $NH_3$/IPA (12 eq).

EXAMPLES

The following examples are offered to illustrate, but not to limit the claimed invention.

Certain molecules claimed in this patent can exist in different enantiomeric and diastereomeric forms and all such variants of these compounds are claimed.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1

Preparation of (5-bromo-1H-pyrrolo[2,3-b]pyridin-3-yl)-(2,6-difluoro-3-nitro-phenyl)methanone (3)

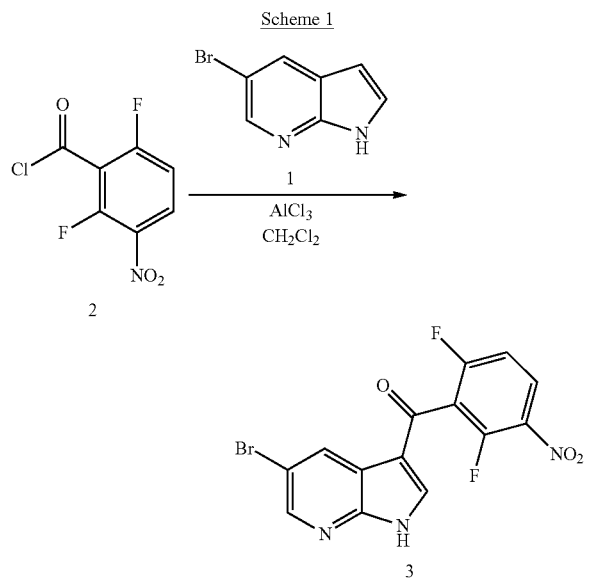

To an 50-liter flask was added 1,2-dichloroethane (DCE, 20 L), followed by 5-bromoazaindole (1) (2 kg, 10.152 mol) to result an orange slurry. Aluminum Chloride (5.421 kg, 40.608 mol) was slowly added to the flask. The first 1.5 kg of the addition was exothermic resulting a dark solution. The rest of the AlCl₃ was added to give a reaction mixture. To the reaction mixture was added 2,6-difluoro-3-nitrobenzoyl chloride 2 (2.25 kg, 10.125 mol) via an addition funnel over a period of 1.5 h. During the addition, the reaction temperature was maintained at or below 45° C. After the addition, the reaction mixture was stirred at 50° C. overnight, cooled to room temperature (~22° C.) and transferred into two separate 20 L flasks. Water (25 L) and acetonitrile (12 L) were added to a 50-liter flask and cooled to 0° C. The reaction mixture was quenched by adding water/acetonitrile solution while keeping the temperature at or below 40° C. The mixture obtained was filtered, and the filtrate was washed with acetonitrile:water (1:1, 2×4 L), water (4 L) and acetonitrile (4 L), followed by drying in vacuum. Compound 3 (2.948 kg, 73.4% yield) was obtained. MS (ESI): M+H⁺=382.9 and 383.9. ¹H NMR (DMSO-d⁶, δ ppm): 7.55 (1H, m), 8.47 (2H, m), 8.53 (1H, d, J=2.2 Hz), 8.65 (1H, d, J=2.2 Hz), 13.25 (1H, s).

Example 2

Preparation of (3-amino-2,6-difluoro-phenyl)-(5-bromo-1H-pyrrolo[2,3-b]pyridin-3-yl)methanone (4)

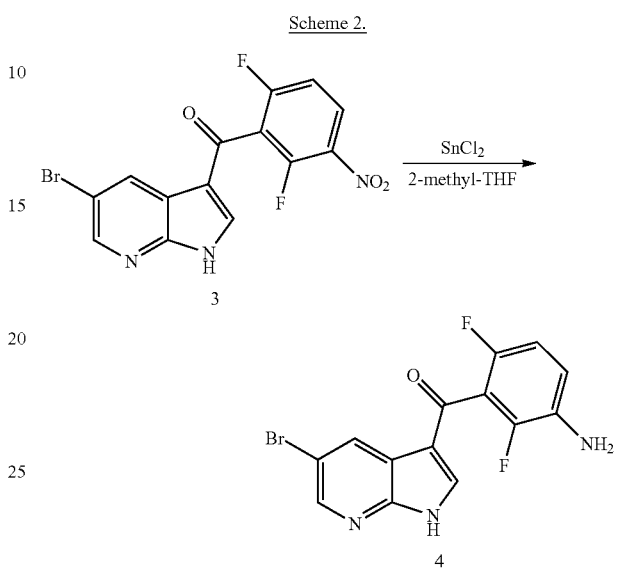

A 50-liter flask was added 2-methyl-tetrahydrofuran (2-methyl-THF) (36 L), compound 3 (2.85 kg, 7.455 mol) and tin(II) chloride (5.03 kg, 22.365 mol). The mixture was heated to 60° C. Upon completion, the reaction was quenched with an aqueous potassium carbonate solution (20%). The resulting mixture was filtered with celite and the solid residue was washed with 2-methyl-THF and tetrahydrofuran (THF). The filtrate was washed with an aqueous NaCl solution (15 L, 10%) and the organic layer was separated. The organic layer was further washed with an aqueous NaCl solution (15 L, 20%) and concentrated on a rotovap to yield compound 4 (2.536 kg, 96.65% yield). MS (ESI): M+H⁺=353 and 354. ¹H NMR (DMSO-d⁶, δ ppm): 5.22 (2H, s), 6.93 (2H, m), 8.12 (1H, s), 8.47 (1H, d J=2.3 Hz), 8.54 (1H, d J-1.6 Hz), 13.2 (1H, s).

Example 3

Preparation of (3-amino-2,6-difluoro-phenyl)-[5-bromo-1-(2,6-dichlorobenzoyl)pyrrolo[2,3-b]pyridin-3-yl]methanone (5)

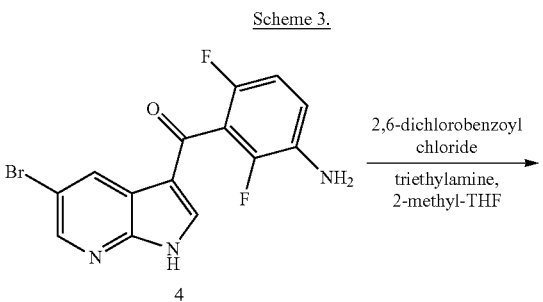

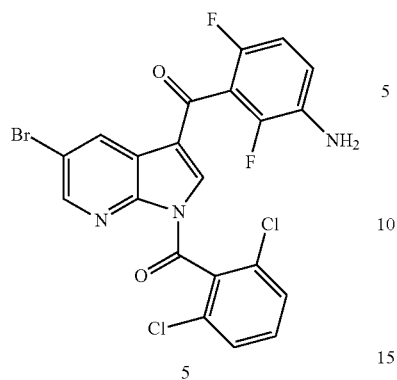

5

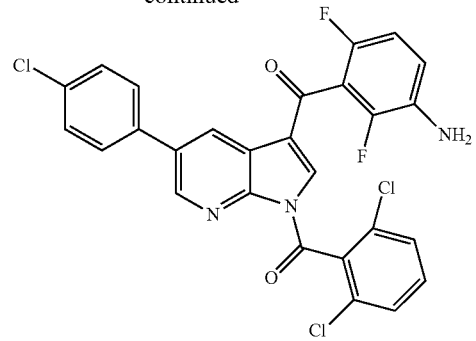

7

Under a nitrogen atmosphere, a 50-liter flask is charged with compound 5 (1.735 kg, 3.304 mol) prepared from Example 3 in 2-methyl-THF, boronic acid 6 (0.877 kg, 5.617 mol), PdCl$_2$(PPh$_3$)$_2$ (0.116 kg, 0.165 mol) and an aqueous sodium bicarbonate (0.833 kg, 9.912 mol) solution (8.7 L). The reaction mixture is degassed and heated to reflux for 7 hrs and stirred at room temperature overnight. Compound 6 (129.0 g) and PdCl$_2$(PPh$_3$)$_2$ (6.6 g) are added again and the reaction mixture is heated to reflux for another 5 hrs. Celite (1.735 kg) is added and the mixture is stirred for 30 minutes and then filtered through a pad of celite. The residue is washed with 2-methyl-THF. The organic layer is separated, washed with a 10% NaCl aqueous solution (4 L) for three times, further washed with a 20% NaCl aqueous solution, filtered, and dried over Na$_2$SO$_4$. The filtrate is concentrated by removing about 80-85% of solvent, added ethyl acetate (3.5 L) and stirred overnight. The mixture is filtered and washed with ethyl acetate (2×3.5 L) twice. Compound 7, is isolated after removing the solvents and drying at 45° C. for 48 hrs (2.765 kg, 74% yield).

Compound 4 (2.5 kg, 7.114 mol) obtained from Example 2 was added into a 50-liter flask and cooled to 9.3° C. To compound 4 in the 50-liter flask was added triethylamine (0.864 kg, 8.537 mol), followed by 4-dimethylaminopyridine (DMAP) (0.087 kg, 0.7114 mol) and 2,6-dichlorobenzoyl chloride (1.34 kg, 6.40 mol) in 2-methyl-THF (25 L) over a period of 2 hrs. The reaction was quenched with methanol (0.30 L at room temperature and added an aqueous NaCl solution (12.5 L, 15%) and celite (0.5 kg). The mixture was stirred and filtered through celite. The filtrate was concentrated and added 5 volumes of heptanes. The resulting solution was stirred for about 1 hr and dried with sodium sulfate (1 kg) and filtered. Compound 5 was isolated by removing the solvents under vacuum (3.47 kg, 92.93% yield). MS (ESI): M+H$^+$=524, 525.8, 527.8. $^1$H NMR (DMSO-d$^6$, δ ppm): 5.36 (2H, s), 7.01 (2H, m), 7.68 (3H, s), 8.34 (1H, brs), 8.61 (1H, brs), 8.72 (1H, d J=2.3 Hz).

Example 5

Preparation of N-[3-[5-(4-chlorophenyl)-1-(2,6-dichlorobenzoyl)pyrrolo[2,3-b]pyridine-3-carbonyl]-2,4-difluoro-phenyl]propane-1-sulfonamide (9)

Example 4

Preparation of (3-amino-2,6-difluoro-phenyl)-[5-(4-chlorophenyl)-1-(2,6-dichlorobenzoyl)pyrrolo[2,3-b]pyridin-3-yl]methanone (7)

Scheme 5.

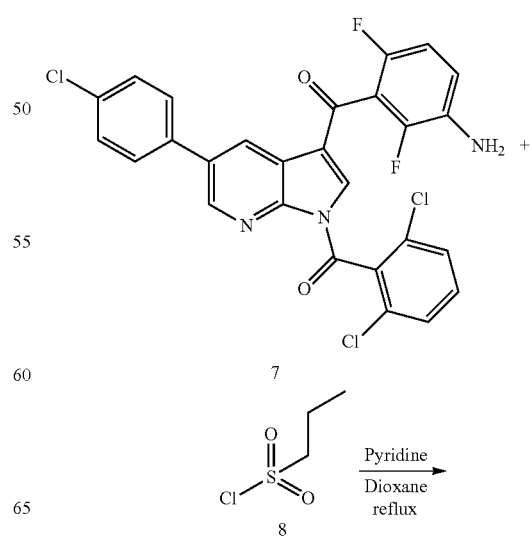

Scheme 4.

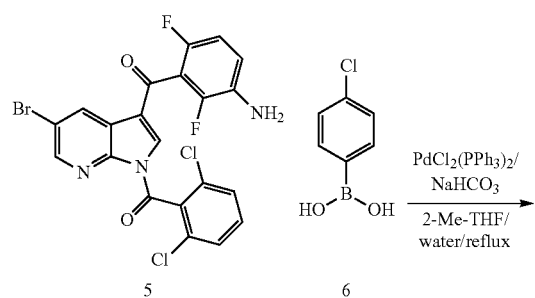

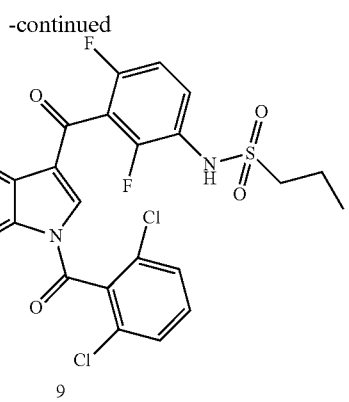

9

To a compound 7 (2.76 kg, 4.961 mol) in dioxane (25 L) is added pyridine (3.92 kg, 49.6 mol), followed by compound 8 (2.42 kg, 16.99 mol). The reaction mixture is heated to reflux and stirred overnight. The dioxane solvent is removed by distillation and the reaction is quenched by adding a mixture of ethyl acetate (16 L) and water (14 L). The reaction mixture is filtered and the filtrate is separated into an organic and an aqueous layer. The organic layer is washed with a 10% NaCl aqueous solution (20 L) followed by a 20% NaCl aqueous solution (20 L). The organic layer is separated, stirred in the presence of activated carbon (350 g) and filtered through celite. Compound 9 is isolated by removing the solvents under vacuum (1.81 kg, 52% yield).

Example 6

Preparation of N-[3-[5-(4-chlorophenyl)-1H-pyrrolo[2,3-b]pyridine-3-carbonyl]-2,4-difluoro-phenyl]propane-1-sulfonamide (10)

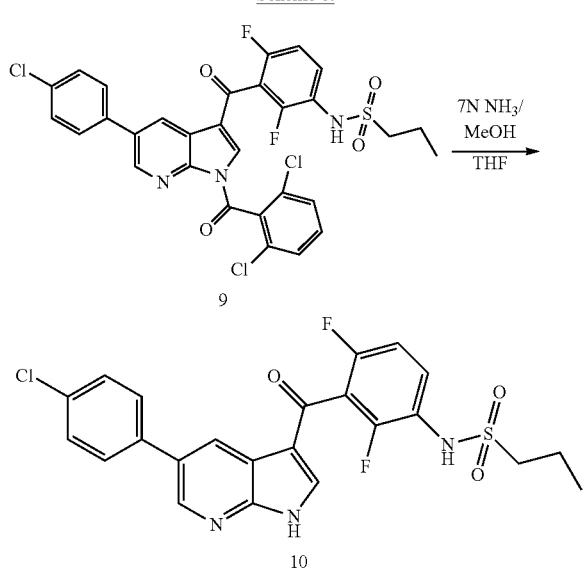

To a high pressure vessel is added compound 9 (1.70 kg, 2.567 mol) in THF (5 L), followed by an ammonia/isopropyl alcohol solution (30.80 mol of ammonia in 12 L of isopropyl alcohol). The mixture is heated to 100° C. overnight. When the reaction is completed, the solvents are removed in vacuum and the residue is dissolved in isopropanol. Compound 10 is isolated and further purified by recrystallization using a mixture of THF (7 L) and isopropanol (14 L). Yield: 0.763 kg (60.7%).

Example 7

Preparation of (3-amino-2,6-difluoro-phenyl)-[5-(4-chlorophenyl)-1-(2,6-dichlorobenzoyl)pyrrolo[2,3-b]pyridin-3-yl]methanone (7)

Scheme 7.

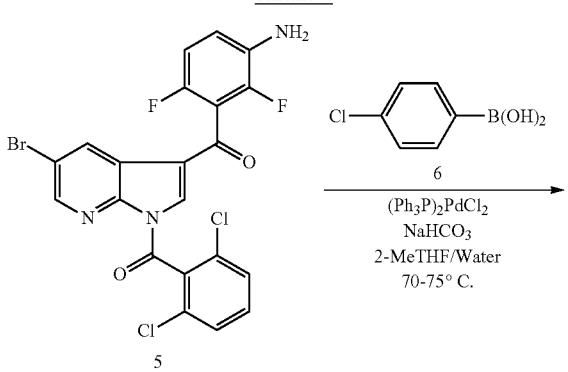

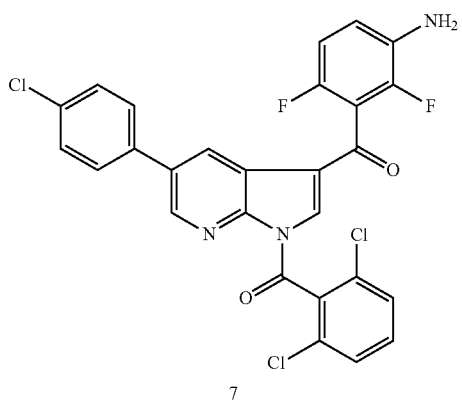

7

Compound 5 (900 g; 1.7 mol) compound 6 (375.8 g; 1.4 mol), sodium bicarbonate (302.6 g; 2.1 mol) followed by 3-methyl-THF (9 L) and water (4.5 L) were added to the 20 L reactor and the mixture was purged with nitrogen at least for 1 h. Bis-triphenylphospino-palladium (II) chloride (60.8 g; 0.086 mol) was added and the reaction mixture was heated to 70-75° C. and stirred for 2 h. The reaction mixture was cooled and filtered over celite pad. The organic layer of the filtrate was separated, washed with water, and concentrated under vacuum. The precipitated solid was isolated by filtration and dried to provide compound 7 (953.9 g) as a brown solid (Purity=95.1%; Yield=100%). $^1$H NMR (DMSO-d6): δ (ppm) 8.75-8.76 (d, J=2.2 Hz, 1H), 8.59 (m, 1H), 8.52 (s, 1H), 7.80-7.82 (d, J=8.6 Hz, 1H), 7.69-7.71 (m, 3H), 7.54-7.56 (d, J=8.6 Hz, 2H), 6.99-7.07 (m, 2H), and 5.36 (s, 2H). MS (ESI) [M+H$^+$]$^+$=556.1 and 558.1.

Example 8

Preparation of N-[3-[5-(4-chlorophenyl)-1-(2,6-dichlorobenzoyl)pyrrolo[2,3-b]pyridine-3-carbonyl]-2,4-difluoro-phenyl]propane-1-sulfonamide (9)

Example 9

Preparation of N-[3-[5-(4-chlorophenyl)-1H-pyrrolo[2,3-b]pyridine-3-carbonyl]-2,4-difluoro-phenyl]propane-1-sulfonamide (10)

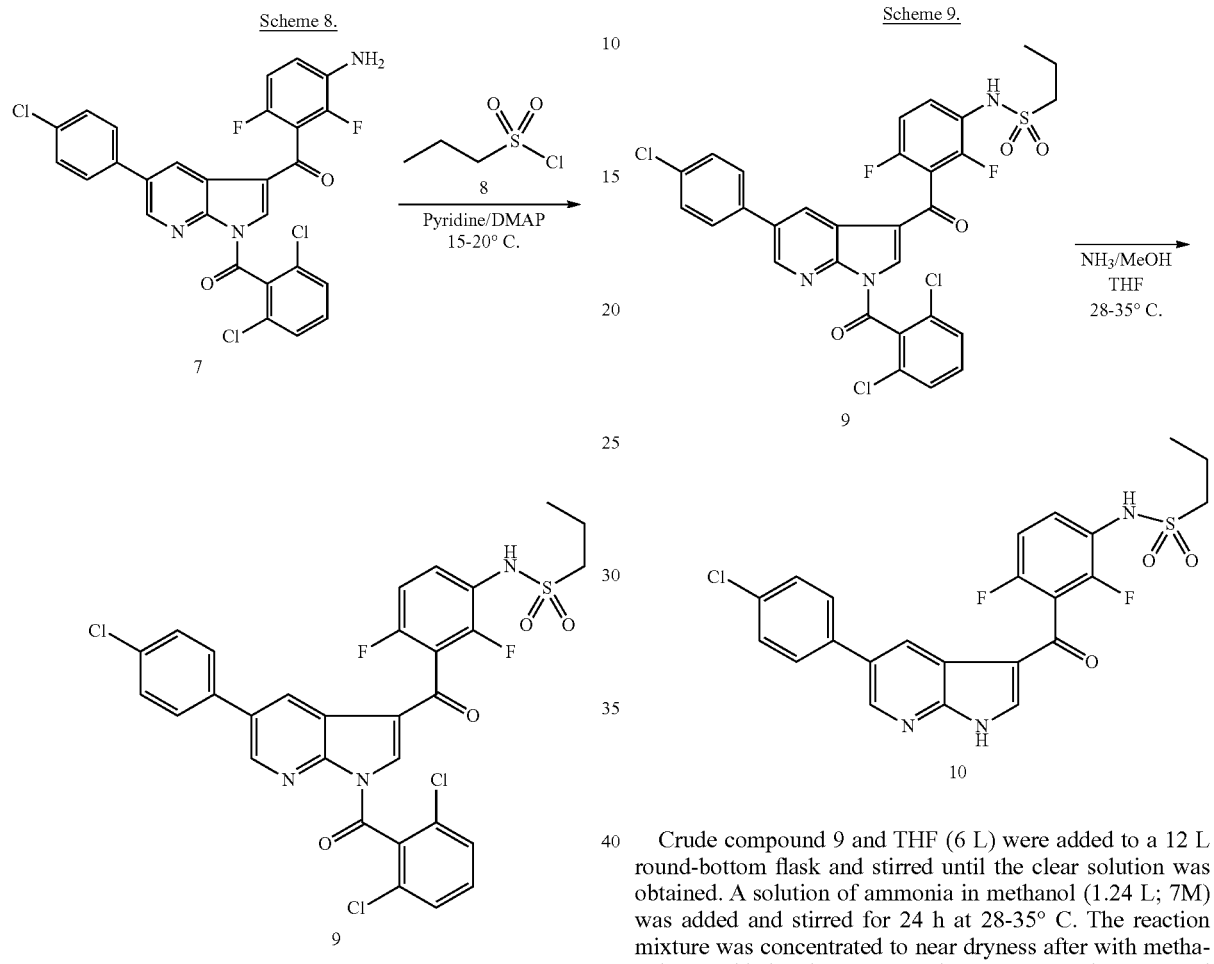

Compound 7 (800 g; 1.44 mol) and dimethylamino pyridine (7.2 g; 0.059 mol), under nitrogen, were added to a 5 L three-necked-round bottom flask cooled in an ice water bath. Anhydrous pyridine (1.8 L) was charged and the mixture was stirred at 10-15° C. until a homogeneous solution was obtained. Propane-1-sulfonyl chloride (308 g; 2.16 mol) was added drop-wise from an addition funnel while keeping the reaction temperature <20° C. and the reaction mixture was stirred at 20-25° C. for 3 h. The reaction mixture was added to a mixture of 2-methyl-THF (7 L) and water (10 L) in a flask and the organic layer was separated, washed with 1N HCl (2 L) followed by brine (2 L), and dried. The residue was azeotroped with toluene to remove the residual water to provide crude compound 9 (1116.4 g) which was used in the next step without purification.

Crude compound 9 and THF (6 L) were added to a 12 L round-bottom flask and stirred until the clear solution was obtained. A solution of ammonia in methanol (1.24 L; 7M) was added and stirred for 24 h at 28-35° C. The reaction mixture was concentrated to near dryness after with methanol was added and concentrated at 45-50° C. The separated solid was filtered and dried at 45-50° C. under vacuum to obtain crude compound 10 (601.7 g; Purity=>95%; Yield=85.4%). Recrystallization of the crude in acetone/methanol (2:1) provided compound 10 in 74% yield with a purity of 98.5%. $^1$H NMR (DMSO-d6): δ (ppm) 9.78 (s, 1H), 8.72-8.73 (d, J=2.2 Hz, 1H), 8.65 (brs, 1H), 8.26 (s, 1H), 7.79-7.82 (d, J=8.5 Hz, 2H), 7.57-7.61 (m, 3H), 7.28-7.32 (t, J=8.3 Hz, 1H), 2.50-2.52 (m, 2H), 1.73-1.78 (m, 2H), and 0.96-0.98 (t, 3H). MS (ESI) [M+H$^+$]$^+$=490.1 and 492.1.

All patents, patent applications and other references cited in the specification are indicative of the level of skill of those skilled in the art to which the invention pertains, and are incorporated by reference in their entireties, including any tables and figures, to the same extent as if each reference had been incorporated by reference in its entirety individually.

One skilled in the art would readily appreciate that the present invention is well adapted to obtain the ends and advantages mentioned, as well as those inherent therein. The methods, variances, and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims While this invention has been disclosed with reference to specific embodiments, it is apparent that other embodiments and variations of this invention may be devised by others skilled in the art without departing from the true spirit and scope of the invention In addition, where features or aspects of the invention are described in terms of Markush groups or other grouping of alternatives, those skilled in the art will recognize that the invention is also thereby described in terms of any individual member or subgroup of members of the Markush group or other group.

Also, unless indicated to the contrary, where various numerical values are provided for embodiments, additional embodiments are described by taking any two different values as the endpoints of a range. Such ranges are also within the scope of the described invention.

What is claimed is:

1. A compound of formula (I):

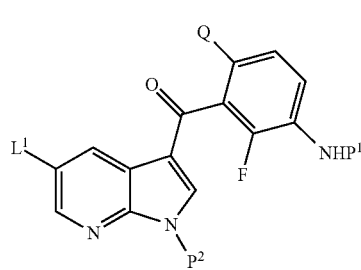
(I)

wherein:
Q is F or H;
$P^1$ is H, 9-fluorenylmethoxycarbonyl, t-butoxycarbonyl, trimethylsilyl or t-butyldiphenylsilyl;
$P^2$ is $R^3$—C(O)— or $R^4$O—C(O)—, wherein $R^3$ and $R^4$ are each $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl, allyl, or vinyl, each of which is optionally substituted; and
$L^1$ is Br, Cl, I, $R^1$—$SO_2O$— or $R^2C(O)O$—; wherein $R^1$ and $R^2$ are each optionally substituted aryl, optionally substituted aryl-$C_{1-4}$alkyl, or optionally substituted $C_{1-6}$alkyl.

2. The compound of claim 1, wherein $P^1$ is H.

3. The compound of claim 1, wherein $R^3$ or $R^4$ is optionally substituted with 1-3 $R^a$ groups, wherein each $R^a$ group is independently halogen, $C_{1-6}$alkyl, fluoro substituted $C_{1-6}$alkyl, fluoro substituted $C_{1-6}$ alkoxy, aryl, heteroaryl, $C_{1-6}$ alkoxy, —CN, —$NO_2$, —OH, $C_{1-6}$ alkyl-OC(O)—, $C_{1-6}$alkyl-C(O)O—, —CH=$CH_2$, or —Si(CH_3)_3, wherein the aliphatic or aromatic portion of $R^a$ is further optionally substituted with from 1-3 $R^b$ groups, wherein each $R^b$ group is halogen, $C_{1-6}$alkyl, $C_{1-6}$alkoxy, —CN, —$NO_2$ or —OH.

4. The compound of claim 3, wherein each $R^a$ group is independently F, Cl, Br, I, —$CH_3$, phenyl, t-butyl, —$OCH_3$, —$NO_2$, —CN, —$CF_3$, —$OCF_3$, —OH or —CH=$CH_2$.

5. The compound of claim 1, wherein $R^3$ and $R^4$ are each methyl, ethyl, phenyl, 2,2,2-trichloroethyl, $(CH_3)_2$CHC≡C—, 2-trimethylsilylethyl, 1-methyl-1-phenylethyl, cyclobutyl, cyclopropyl, allyl, vinyl, 1-adamantyl, benzyl or diphenylmethyl.

6. The compound of claim 1, wherein $L^1$ is Br, Cl, I, tosyl-O—, mesyl-O—, trifluoromethanesulfonyl-O—, $R^1$—$SO_2O$— or $R^2C(O)O$—, wherein $R^1$ and $R^2$ are each aryl, aryl-$C_{1-4}$alkyl or $C_{1-6}$alkyl, each of which is optionally substituted with from 1-3$R^c$ substituents, wherein each $R^c$ is independently halogen, —CH=$CH_2$, —CN, —OH, —$NH_2$, $NO_2$, —C(O)OH, —C(O)$NH_2$, —$S(O)_2NH_2$, —NHC(O)$NH_2$, —NHC(S)$NH_2$, —$NHS(O)_2NH_2$, —C(NH)$NH_2$, —$OR^d$, —$SR^d$, —OC(O)$R^d$, —C(O)$R^d$, —C(O)$OR^d$, —C(S)$OR^d$, —S(O)$R^d$, —$S(O)_2R^d$, —C(O)$NHR^d$, —C(O)$NR^dR^d$, —$S(O)_2NHR^d$, —$S(O)_2NR^dR^d$, —C(NH)$NHR^d$, —C(NH)$NR^dR^d$, —NHC(O)$R^d$, —$NR^dC(O)R^d$, —$NHS(O)_2R^d$, —$NR^dS(O)_2R^d$, —NHC(O)$NHR^d$, —$NHR^d$ or —$NR^dR^d$, wherein each $R^d$ substituent is independently $C_{1-6}$alkyl or aryl.

7. The compound of claim 6, wherein $L^1$ is Br, Cl, I, tosyl-O—, mesyl-O—, trifluoromethanesulfonyl-O—, $CF_3C(O)O$— or $CH_3C(O)O$—.

8. The compound of claim 1, wherein $P^1$ is H; $P^2$ is $R^3$—C(O)—; and $L^1$ is Br.

9. The compound of claim 1, wherein $P^1$ is H; $P^2$ is $R^4O$—C(O)—; and $L^1$ is Br.

10. A method for preparing a compound of formula (I)

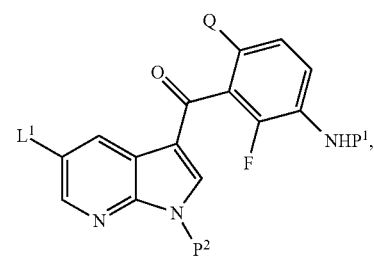
(I)

said method comprising:
contacting a compound of formula (II):

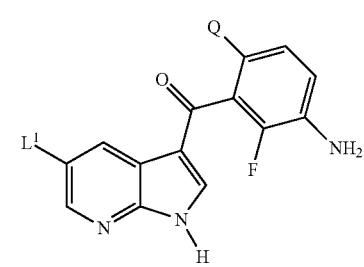
(II)

with an agent of formula: $P^2$—$X^1$ under conditions sufficient to form the compound of formula (Ia):

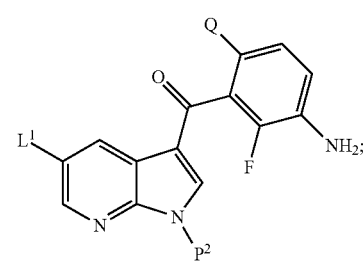
(Ia)

and
reacting a compound of formula (Ia) with an agent of formula: $P^1$—$X^3$ under conditions sufficient to form the compound of formula (I);

wherein:
$X^1$ is Br, Cl, I, tosyl-O—, mesyl-O—, trifluoromethanesulfonyl-O—, $CF_3C(O)O$— or $CH_3C(O)O$—;

$X^3$ is a leaving group;

$P^1$ is 9-fluorenylmethoxycarbonyl, t-butoxycarbonyl, trimethylsilyl or t-butyldiphenylsilyl;

$P^2$ is $R^3$—C(O)— or $R^4$O—C(O)—, wherein $R^3$ and $R^4$ are each $C_{1-6}$alkyl, aryl, heteroaryl, aryl-$C_{1-2}$alkyl, heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted;

Q is H or F; and $L^1$ is Br, Cl, I, $R^1$—$SO_2O$— or $R^2C(O)O$—; wherein $R^1$ and $R^2$ are each optionally substituted aryl or optionally substituted $C_{1-6}$alkyl.

11. The method of claim 10, wherein said contacting is carried out in the presence of triethylamine and 4-dimethylaminopyridine.

12. The method of claim 10, wherein $L^1$ is Br.

13. The method of claim 10, wherein $P^2$ is 2,6-dichlorophenylcarbonyl; and $L^1$ is Br.

14. The method of claim 10, wherein Q is F.

15. The method of claim 10, wherein $R^3$ or $R^4$ is optionally substituted with 1-3 $R^a$ groups, wherein each $R^a$ group is independently halogen, $C_{1-6}$alkyl, fluoro substituted $C_{1-6}$alkyl, fluoro substituted $C_{1-6}$alkoxy, aryl, heteroaryl, $C_{1-6}$alkoxy, —CN, —$NO_2$, —OH, $C_{1-6}$alkyl-OC(O)—, $C_{1-6}$alkyl-C(O)O—, —CH=$CH_2$, or —Si($CH_3$)$_3$, wherein the aliphatic or aromatic portion of $R^a$ is further optionally substituted with from 1-3 $R^b$ groups, wherein each $R^b$ group is independently halogen, $C_{1-6}$alkyl, $C_{1-6}$alkoxy, —CN, —$NO_2$ or —OH.

16. The method of claim 15, wherein $R^a$ is F, Cl, Br, I, —$CH_3$, phenyl, t-butyl, —$OCH_3$, —$NO_2$, —CN, —$CF_3$, —$OCF_3$, —OH or —CH=$CH_2$.

17. A method for preparing a compound of formula (Ia):

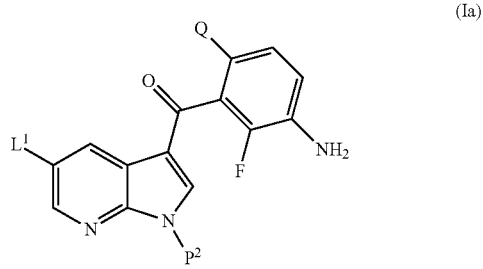

(Ia)

said method comprising:
contacting a compound of formula (II):

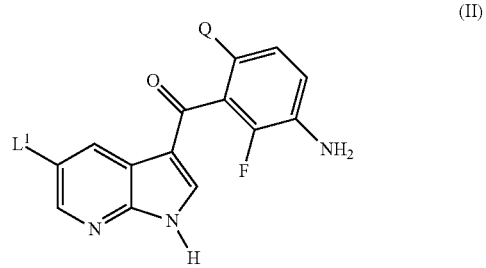

(II)

with an agent of formula: $P^2$—$X^1$ under conditions sufficient to form the compound of formula (Ia), wherein:

$X^1$ is Br, Cl, I, tosyl-O—, mesyl-O—, trifluoromethanesulfonyl-O—, $CF_3C(O)O$— or $CH_3C(O)O$—;

$P^2$ is $R^3$—C(O)— or $R^4$O—C(O)—, wherein $R^3$ and $R^4$ are each $C_{1-6}$alkyl, aryl, heteroaryl, aryl-$C_{1-2}$alkyl heteroaryl-$C_{1-2}$alkyl, $C_{3-10}$cycloalkyl, $C_{3-10}$cycloalkyl-$C_{1-2}$alkyl, ethynyl or vinyl, each of which is optionally substituted;

Q is H or F; and $L^1$ is Br, Cl, I, $R^1$—$SO_2O$— or $R^2C(O)O$—; wherein $R^1$ and $R^2$ are each optionally substituted aryl or optionally substituted $C_{1-6}$alkyl.

18. The method of claim 17, wherein $P^2$ is 2,6-dichlorophenylcarbonyl; and $L^1$ is Br.

19. The method of claim 17, wherein Q is F.

20. The method of claim 17, wherein $R^3$ or $R^4$ is optionally substituted with 1-3 $R^a$ groups, wherein each $R^a$ group is independently halogen, $C_{1-6}$alkyl, fluoro substituted $C_{1-6}$alkyl, fluoro substituted $C_{1-6}$alkoxy, aryl, heteroaryl, $C_{1-6}$alkoxy, —CN, —$NO_2$, —OH, $C_{1-6}$alkyl-OC(O)—, $C_{1-6}$alkyl-C(O)O—, —CH=$CH_2$, or —Si($CH_3$)$_3$, wherein the aliphatic or aromatic portion of $R^a$ is further optionally substituted with from 1-3 $R^b$ groups, wherein each $R^b$ group is independently halogen, $C_{1-6}$alkyl, $C_{1-6}$alkoxy, —CN, —$NO_2$ or —OH.

* * * * *